United States Patent
Straub et al.

(10) Patent No.: US 10,435,472 B2
(45) Date of Patent: Oct. 8, 2019

(54) METHOD OF TREATING BONE METASTASIS DISEASES, MEDICAMENTS THEREFORE, AND A METHOD OF PREDICTING THE CLINICAL OUTCOME OF TREATING BONE METASTASIS DISEASES

(71) Applicant: Merck Patent GmbH, Darmstadt (DE)

(72) Inventors: Josef Straub, Seeheim-Jugenheim (DE); Eike Staub, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/511,959

(22) PCT Filed: Aug. 18, 2015

(86) PCT No.: PCT/EP2015/001701
§ 371 (c)(1),
(2) Date: Mar. 16, 2017

(87) PCT Pub. No.: WO2016/041616
PCT Pub. Date: Mar. 24, 2016

(65) Prior Publication Data
US 2017/0298133 A1 Oct. 19, 2017

Related U.S. Application Data

(60) Provisional application No. 62/051,525, filed on Sep. 17, 2014.

(51) Int. Cl.
| | |
|---|---|
| *A61K 38/09* | (2006.01) |
| *C07K 16/28* | (2006.01) |
| *A61K 39/395* | (2006.01) |
| *G01N 33/574* | (2006.01) |
| *A61K 45/06* | (2006.01) |
| *A61K 39/00* | (2006.01) |

(52) U.S. Cl.
CPC .......... *C07K 16/2848* (2013.01); *A61K 38/09* (2013.01); *A61K 39/39558* (2013.01); *A61K 45/06* (2013.01); *G01N 33/57484* (2013.01); *G01N 33/57488* (2013.01); *A61K 2039/505* (2013.01); *A61K 2039/545* (2013.01); *C07K 2317/24* (2013.01); *C07K 2317/94* (2013.01); *G01N 2800/52* (2013.01)

(58) Field of Classification Search
CPC ................................................... A61K 38/09
USPC ........................................................ 435/6.1
See application file for complete search history.

(56) References Cited

U.S. PATENT DOCUMENTS

| | | | |
|---|---|---|---|
| 5,985,278 A | 11/1999 | Mitjans et al. | |
| 7,163,681 B2 | 1/2007 | Giles-Komar et al. | |
| 2007/0117164 A1* | 5/2007 | Raskov ............ | G01N 33/57419 435/7.23 |

FOREIGN PATENT DOCUMENTS

| | | |
|---|---|---|
| EP | 0719859 B1 | 7/2003 |
| EP | 0531472 B1 | 8/2003 |
| WO | 2002/012501 A2 | 2/2002 |
| WO | 2009/010290 A2 | 1/2009 |
| WO | 2010/096627 A1 | 8/2010 |
| WO | 2012/024612 A1 | 2/2012 |
| WO | 2012/107211 A1 | 8/2012 |
| WO | 2012/167028 A2 | 12/2012 |
| WO | 2013/152313 A1 | 10/2013 |

OTHER PUBLICATIONS

Trikha et al (Int J Cancer, 2004, 110(3): Abstract).*
Garcia-Cordero et al (Lab Chip, 14(15): 2642-2650).*
Kuku et al (Mediators Inflamm, 2005, 3: 171-174).*
Morgans et al (Urol Clin North Am, 2012, 39(4): 533-546).*
Garcia-Cordero et al (Lab Chip, 2014, 14(15): 2642-2650).*
Stephen F. Altschul, et al., J. Mol. Biol., 215, 403-410 (1990).
John S. Munger and Dean Sheppard, Cold Spring Harb. Perspect. Biol, 3:a00517 [1-17] (2011).
Coleman RE, Clin. Cancer Res. 12 (20 Pt 2): 6243s-6249s (2006).
Guise T., Semin. Oncol. 37 (Suppl 2): S2-14 (2010).
Jimenez-Andrade JM, et. al., Annals of the New York Academy of Sciences 1198: 173-81 (2010).
K. R. Aigner, Isolated liver perfusion. In: Morris DL, McArdle CS, Onik GM, eds. Hepatic Metastases. Oxford: Butterworth Heinemann, 101-107 (1996).
Zheng et al., Cancer Research; 59, 1655-1664 (1999).
Azure, J. et al., Molecular and Cellular Biology; 27, 4444-4453 (2007).
Bisanz et al., Molecular Therapy; 12(4), 634-643 (2005).
McCabe et al., Oncogene; 26(42), 6238-6243 (2007).
Legate KR, et al. Nat Rev Mol Cell Biol;7(1):20-31; Clin (2006).
Guise TA, et al., Clin. Cancer Res, 12:6213s-16s (2006).
Mitjans F, et al. J Cell Sci; 108:2825-38 (1995).
Monnier Y, et al., Cancer Res; 68(18):7323-31 (2008).
Wirth M, et al., Eur Urol;65(5):897-904 (2014).
Huiqing, Liu et al., Genes Chromosomes & Cancer, 53(4) 349-357 (2014).
Reardon D.A. et al., Genes and Cancer, 2(12) 1159-1165 (2011).
Elez E. et al., Annals of Oncology, 25 Suppl. 2, ii107-ii108 (2014).

* cited by examiner

*Primary Examiner* — Sean E Aeder
(74) *Attorney, Agent, or Firm* — Grüneberg and Myers PLLC

(57) ABSTRACT

The instant invention provides for a new method of treating bone metastasis diseases in subjects, wherein said method preferably depends on whether the subject shows certain specific proteins levels in one or more body fluids prior to or during treatment, wherein said treatment comprises the administration of at least one pan αv integrin inhibitor to a subject, a medicament for use in said new methods, and a method of predicting the outcome of a treatment with at least one pan αv integrin inhibitor based on said specific protein levels in one or more body fluids of the subject.

23 Claims, 24 Drawing Sheets

Specification includes a Sequence Listing.

METHOD OF TREATING BONE METASTASIS DISEASES, MEDICAMENTS THEREFORE, AND A METHOD OF PREDICTING THE CLINICAL OUTCOME OF TREATING BONE METASTASIS DISEASES

RELATED APPLICATIONS

This application is a U.S. national stage application of PCT international application PCT/ EP2015/001701, filed on Aug. 18, 2015, which claims the benefit of U.S. provisional application Ser. No.: 62/051,525, filed on Sep. 17, 2014. The entire contents of the aforementioned applications are, hereby, incorporated by reference.

SEQUENCE LISTING

The instant application contains a Sequence Listing which has been submitted electronically in ASCII format and is hereby incorporated by reference in its entirety. Said ASCII copy, created on Mar. 15, 2017, is named P14169 DO sequence listing ST25.txt and is 94,208 bytes in size.

BACKGROUND OF THE INVENTION

Field of the Invention

The instant invention provides for a new method of treating bone metastasis diseases in subjects, wherein said method preferably depends on whether the subject shows certain specific proteins levels in one or more body fluids prior to or during treatment, wherein said treatment comprises the administration of at least one pan αv integrin inhibitor to a subject, a medicament for use in said new methods, and a method of predicting the outcome of a treatment with at least one pan αv integrin inhibitor based on said specific protein levels in one or more body fluids of the subject.

More specifically, the instant invention provides for a new method of treating of treating bone metastasis diseases, preferably bone metastasis disease is derived from prostate cancer, breast cancer and/or cancer in subjects with at least one pan αv integrin inhibitor, preferably including the pan αv integrin inhibitor abituzumab or Intetumumab, wherein said subjects show certain specific protein levels in one or more body fluids prior to or during treatment.

Discussion of the Background

Bone metastases, or metastatic bone disease, is a class of cancer metastases that results from primary tumor invasion to bone. Bone is one of the most common locations for metastasis. [Coleman R E (October 2006). "Clinical features of metastatic bone disease and risk of skeletal morbidity". Clin. Cancer Res. 12 (20 Pt 2): 6243s-9s.] While any type of cancer is capable of forming metastatic tumors within bone, the microenvironment of the marrow tends to favor particular types of cancer, including prostate, breast, and lung cancers. [Guise T (October 2010). "Examining the metastatic niche: targeting the microenvironment". Semin. Oncol. 37 (Suppl 2): S2-14.] Particularly in prostate cancer, bone metastases tend to be the only site of metastasis.[ Jimenez-Andrade J M, Mantyh W G, Bloom A P, Ferng A S, Geffre C P, Mantyh P W (June 2010). "Bone cancer pain". Annals of the New York Academy of Sciences 1198: 173-81.]

Lung cancer, also known as carcinoma of the lung or pulmonary carcinoma, is a malignant lung tumor characterized by uncontrolled cell growth in tissues of the lung. If left untreated, this growth can spread beyond the lung by process of metastasis into nearby tissue or other parts of the body, including the liver, brain and bone. Most cancers that start in the lung, known as primary lung cancers, are carcinomas that derive from epithelial cells. The main primary types are small-cell lung carcinoma (SCLC), and non-small-cell lung carcinoma (NSCLC). Non-small-cell lung carcinoma (NSCLC) is any type of epithelial lung cancer other than small cell lung carcinoma (SCLC). As a class, NSCLCs and metastases thereof are relatively insensitive to chemotherapy, compared to small cell carcinoma. A wide variety of chemotherapies are used in metastatic NSCLC, unfortunately with little effect to date. Small-cell carcinoma or small-cell lung cancer (SCLC) is a type of highly malignant cancer that most commonly arises within the lung, although it can occasionally arise in other body sites, such as the cervix, prostate, and gastrointesinal tract. SCLC usually metastasizes widely very early on in the natural history of the tumor. Also in this case, the metastasis affects predominantely the bone, liver and brain.

Breast cancer develops from breast tissue. It most commonly develops in cells from the lining of milk ducts and the lobules that supply the ducts with milk. Cancers developing from the ducts are known as ductal carcinomas, while those developing from lobules are known as lobular carcinomas. In addition, there are more than 18 other sub-types of breast cancer. The diagnosis of breast cancer is regularily confirmed by taking a biopsy of the concerning lump. Once the diagnosis is made, further tests are done to determine if the cancer has spread beyond the breast and which treatments it may respond to. If the cancer has spread beyond the breast, the breast cancer presents as metastatic disease. The symptoms caused by metastatic breast cancer will depend on the location of metastasis. Common sites of metastasis include bone, liver, lung and brain.

The metastatic process is a multistep event and represents the most dreadful aspect of cancer. At the moment of diagnosis, cancers are frequently far advanced in their natural history, and the presence of metastases is a common event. In fact, approximately 30% of patients have detectable metastases at the moment of clinical diagnosis and a further 30% of patients have occult metastases. Metastases can be disseminated and they can infest different organs at the same time, or localize to a specific organ. In the case of localized disease, surgery is the treatment of choice; however recurrence and prognosis depend on many criteria such as: resectability, patient's clinical situation, and number of metastases.

After resection, recurrence is common, suggesting that micrometastatic foci are present at the moment of diagnosis. Systemic chemotherapy is an ideal setting but only few patients are cured by it, and in the majority systemic chemotherapy fails. Many physiological barriers and pharmacokinetic parameters contribute to decrease its efficacy. Liver, lungs and lymph nodes are filtration organs and therefore inclined to metastasization. The poor chemosensitivity of metastases, peculiarly those of colorectal origin has forced many researchers to use methods for increasing the time and the concentration of drugs. The need for decreasing or limiting the side effects for this important and delicate organ led to the development of the technique of liver isolation for perfusion of antineoplastic agents. (K. R. Aigner, Isolated liver perfusion. In: Morris D L, McArdle C S, Onik G M, eds. Hepatic Metastases. Oxford: Butterworth Heinemann, 1996. 101-107). Since 1981, modifications and technical improvements have been continuously introduced. Liver metastases may be of different origin and their chemosensitivity may vary according to the histological type and their response in presence of heat. There still exists a growing need in the art in order to develop new therapeutic strategies for treating cancer, especially metastases, systemically.

The object of the present invention therefore was to develop such a new strategy. It should be applicable to systemic treatment, and it should lower the dose and/or increase the efficiency of the cancer therapeutical agents to be applied. A further object was to normalize tumor vasculature to increase delivery of systemic therapeutics of tumor, i.e. to reset the tumor vasculature to the functionality of the vasculature of non-tumor tissue.

Thus, it is a preferred objective of the instant invention to provide a more effective, better tolerated treatment for humans, especially human cancer patients suffering from bone metastases, preferably bone metastases independent from their origin, thus preferably leading to enhanced overall survival (OS), progression-free survival (PFS), quality of life (QOL) and/or increased median survival.

Prostate cancer is the most commonly occurring cancer aside skin cancer in the US, and is the second most common cause of male cancer deaths. Prostate cancer is classified in four stages: Stage I prostate cancer is found in the prostate only and cannot be felt during a digital rectal exam nor is it visible by imaging. In stage II prostate cancer, the tumor has grown inside the prostate but has not extended beyond it, whereas in stage III, the cancer has spread outside the prostate, but to a minimal extent only. Often, prostate cancer in stage III will have spread only to nearby tissues, such as the seminal vesicles. Finally, in stage IV, the cancer has spread outside the prostate to other tissues, such as the lymph nodes, bones, liver, and/or lungs or brain.

The spectrum of prostate cancers that are progressing despite castrate levels of testosterone includes tumors that have shown varying degrees and durations of response to primary hormone treatment, and clinical manifestations that range from a rising prostate-specific antigen (PSA) alone, a rising PSA with osseous and/or soft-tissue spread, or a predominantly visceral disease pattern.

Currently approved treatment of prostrate cancer includes surgical castration, chemical castration, or a combination of surgical and chemical castration. Removal of the testes, the primary testosterone producing organ, reduces the levels of circulating androgens, to less than 5% of normal levels. This reduction in androgen levels inhibits prostate tumor growth. Although the anti-tumor effects of surgical castration are direct, the anti-tumor effects can be temporary. Surgical castration often leads to clonal selection of androgen-independent prostate tumor cells. This results in re-growth of the prostate tumor in a form that proliferates without testosterone or DHT Stimulation. Chemical castration (also called medical castration) is often substituted for surgical castration, as an initial treatment. Despite its high prevalence, treatment options for men having prostate cancer remain relatively limited and typically depend on the stage of the cancer.

Treatment options include surgical treatments such as radical prostatectomy, in which the prostate is completely removed and radiation, applied through an external beam that directs the dose to the prostate from outside the body or via low-dose radioactive seeds that are implanted within the prostate to kill cancer cells locally. Anti-androgen hormone therapy also is used in the treatment of prostate cancer, either alone or in conjunction with surgery or radiation. Hormone therapy typically aims at blocking the pituitary from producing hormones that stimulate testosterone production by use of castration or administration of hormone analogs and requires that patients have injections of these hormone analogs for protracted periods. Finally, chemotherapeutic approaches have been used to treat advanced prostate cancer, usually as a last resort when other approaches have failed. Since a couple of years, the combination of docetaxel and prednisone was established as the new standard of care for patients who have progressed on androgen deprivation. None of the treatments described above are curative and prostate cancer being androgen dependent at first, often will progress despite surgical and hormonal-based therapies, and become resistant over time, leading to a cancer type which is called "hormone refractory cancer" or "castration resistant cancer" (CRPC).

Clinical disease manifestations of CRPC are commonly related to bone metastases and may include pain, pathologic fractures, and spinal cord compression, with local recurrences that may be associated with pelvic discomfort, renal dysfunction due to ureteral compression, bladder outlet obstruction, and sexual dysfunction. Further, while bone cancer is the predominant result of CRPC, patients may develop soft-tissue metastases (lymph node(s)) and visceral metastasis in liver, lung, brain, and other organs. Patients with CRPC are minimally responsive to chemotherapy and the majority of patients die due to progressive prostate cancer within 20 months of initiating treatment. Bisphosphonates are commonly used in patients with castrate-resistant prostate cancer who have bone metastases.

It has been shown that prostate tumors remain dormant and clinically undetectable until they begin to secrete angiogenic factors and down-regulate the expression of angiogenic inhibitors. In general, it can be stated that angiogenesis is critical to the genesis of prostate tumors. Therefore, it was not completely surprising that anti-angiogenic agents may inhibit prostate cancer cell growth.

In prostate cancer, tumor cells express an abnormal integrin repertoire and are surrounded by a markedly aberrant extracellular matrix (ECM). These changes have profound consequences, given the ability of each integrin to regulate specific cell functions. Expression of $\beta3$ and $\beta1$ subunits activates specific signaling pathways and support distinct cancer cell functions. $\beta3$ is uniquely required in cancer cells for increasing cdc2 levels as well as cdc2 kinase activity. These effects are specific for $\beta3$ and are not observed for $\beta6$. Up-regulation of $\beta3$ and $\beta6$ integrin variants has been described. Zheng et al. (Cancer Research 1999; 59, 1655-1664) used human prostate cancer cells isolated from sixteen surgical specimens, to show that these cells express $\alpha v\beta3$, whereas normal prostate epithelial cells do not. Similarly, $\alpha v\beta6$ was found to be expressed in adenocarcinoma (Azare et al.; Molecular and Cellular Biology 2007; 27, 4444).

The use of integrin inhibitors is likely to affect both cancer cell survival and angiogenesis since integrins are expressed by tumor cells as well as by endothelial cells. Although it is hard to discriminate between an effect on tumor growth and an effect on angiogenesis, a maximal response of these inhibitors can be predicted when the targeted integrin is expressed by both tumor and endothelial cells.

Bone is the most frequent metastatic site for prostate cancer. Bisanz et al. (Molecular Therapy 2005; 12, 634-643) illustrate a positive role for alpha-v integrins on prostate tumor survival in the bone. Analysis of human prostate cancer bone xenografts shows that intratumoral administration of liposome encapsulated human alpha-v siRNAs significantly inhibits the growth of PC3 tumors in bone and increases apoptosis of prostate tumor cells. Further studies (McCabe et al., Oncogene 2007; 26, 6238-6243) demonstrate that αvβ3 integrin activation on tumor cells is essential for the recognition of key bone specific matrix proteins. These data suggest that the αvβ3 integrin modulates prostate cancer growth in distant metastasis. Since integrins mediate the interactions between tumor cells and bone microenvironment and facilitate growth in bone, a potential application of the use of integrin inhibitors is to prevent prostate cancer bone lesions.

These lesions are osteoblastic and/or osteolytic and are frequently detected in prostate cancer patients (over 80% of prostate cancer patients have established bone metastasis at autopsy).

A recent study has shown that the αvβ3 integrin promotes bone gain mediated by prostate cancer cells that metastasize to the bone and point to αvβ3 as a potential therapeutic target to block prostate cancer osteoblastic lesions. Immunohistochemical analysis has demonstrated the presence of αv integrin in a large proportion of human prostate cancer tissues samples.

These and other results suggest that anti-integrin agents may have both direct and indirect antitumor activity. But there are only few clinical trials reporting that peptide or non-peptide integrin inhibitors are effective agents in prostate cancer therapy.

Therefore, there is a need to provide a method of treatment of bone metastases, preferably bone metastases of breast cancer, lung cancer and/or prostate cancer. Moreover, there is a especially high need to provide a method for the treatment of prostate cancer bone metatases, especially castration-resistant prostate cancer bone metastases.

Therefore, there is a also a need to provide a method of treatment of bone metastases from metastatic androgen independent prostate cancer (mAIPCa) and/or bone metastases from metastatic androgen dependent prostate cancer (mADPCa).

SUMMARY OF THE INVENTION

According to an aspect of the invention there is provided a method for identifying bone metastasis in a subject, preferably a human subject, that is susceptible to treatment with at least one pan αv integrin inhibitor, preferably Abituzumab, comprising determining said certain proteins levels in one or more body fluids, whereby a high level of one or more proteins selected from a first group of said specific proteins and/or a low level of one or more proteins from a second group of said specific proteins indicates the tumor is susceptible to said treatment.

Body fluids are preferably the liquids originating from inside the bodies of living subjects, preferably living human subjects. They include fluids that are excreted or secreted from the body as well as body water that normally is not excreted or secreted.

The body fluids can preferably specified by type, such as intracellular fluids, extracellular fluids, intravascular fluids (e.g. whole blood, blood and blood plasma), interstitial fluids, lymphatic fluids (sometimes regarded as a subtype of interstitial fluids), and transcellular fluids.

Preferred body fluids are selected from the group consisting of whole blood (preferably also referred to as "blood"), blood serum (preferably also referred to as "serum"), blood plasma (preferably also referred to as "plasma"), exudate, lymph, mucus, peritoneal fluid, saliva, sputum, tears and urine. Especially preferred body fluids selected from the group consisting of Preferred body fluids are selected from the group consisting of whole blood (preferably also referred to as "blood"), blood serum (preferably also referred to as "serum"), and blood plasma (preferably also referred to as "plasma"). Especially preferred is blood plasma (preferably also referred to as "plasma"). Alternatively preferred is blood serum (preferably also referred to as "serum"), and whole blood (preferably also referred to as "blood").

The threshold for categorization of patients into "low level" or "high level" for each of said specific proteins is preferably determined by listing of all available levels for that respective specific protein in the respective body fluid, then determining the median from this listing of said specific protein level values in said body fluid, and taking this median value as the threshold.

This threshold is preferably also referred to herein as median threshold. Preferably, said threshold or median threshold is determined in the population of subjects suffering from the respective bone metastasis disease as described herein. More preferably, said threshold or median threshold for the respective specific protein is determined from the body fluid of a plurality of subjects being part of a diseased subject population suffering from the respective bone metastasis disease.

For example, for determining said median threshold for one or more said specific proteins, body fluid samples (here: blood samples) are taken from 150 human subjects suffering from metastatic castrate-resistant prostate cancer (mCRPC) in order to obtain about 500 µL offer a preferred body fluid (here: blood plasma). The levels of the contained specific proteins of interest, e.g. STX1A are determined using an aptamer based protein detection system, e.g. the SomaLogic Proteomic Affinity Assay Method described in detail in the Experimental Section, whereby results for each protein of interest are represented by relative fluorescence readouts reported by the detection system. In an optional next step, the obtained raw data set can be simplified by removing the data of proteins not of interest, e.g. proteins that are known to be derived or affected by inadequate sample handling during plasma protein, such as platelet activation or cell lysis which may occur during the plasma preparation process. The thus obtained data set is then preferably subjected to steps such as data normalization procedures in order to obtain robust signals of the proteins of interest and estimates of the median protein levels across the study population of patients. Preferably, this data analysis process includes a cut-of optimisation. This procedure thus provides a median threshold of one or more specific proteins of interest, e.g. the median threshold for the protein STX1A. Taking this obtained median threshold, both said 150 human subjects suffering from metastatic castrate-resistant prostate cancer (mCRPC), as well as future human subjects suffering from mCRPC, can then be readily characterised as having a high level or a low level, respectively, of one or more specific proteins of interest, e.g. STX1A, with the predicted specific impact on the clinical outcome of the treatment with at least one pan αv integrin inhibitor, optionally in combination with one or more chemotherapeutic agents.

Preferably, the body fluid sampling and/or the evaluation of the median value for the respective specific protein is performed prior to treatment of the respective bone metastasis disease with said at least one pan αv integrin inhibitor. Preferably, patients are classified as "high level" if their respective specific protein level in said body fluid is higher than the median threshold. Accordingly, patients are preferably classified as "low level" if their respective specific protein level in said body fluid is lower than or equal to said median threshold.

More preferably, the threshold for categorization of patients into "low level" or "high level" for each of said specific proteins is preferably determined by listing of all available levels for that respective specific protein in the blood plasma, then determining the median from this listing of said specific protein level values in said blood plasma, and taking this median value as the threshold. This threshold is preferably also referred to herein as median threshold. Preferably, the blood plasma sampling and/or the evaluation of the median value for the respective specific protein is performed prior to treatment of the respective bone metastasis disease with said at least one pan αv integrin inhibitor. Preferably, patients are classified as "high level" if their respective specific protein level in said blood plasma is higher than the median threshold. Accordingly, patients are preferably classified as "low level" if their respective specific protein level in said blood plasma is lower than or equal to said median threshold.

Preferably, the respective bone metastasis disease in this regard is metastatic prostate cancer, more preferably metastatic castration-resistant prostate cancer (mCRPC). Preferably, the at least one pan αv integrin inhibitor comprises Abituzumab or Intetumumab). More preferably, the at least one pan αv integrin inhibitor is Abituzumab or Intetumumab. Especially preferred, the at least one pan αv integrin inhibitor is Abituzumab.

More preferably, the threshold for categorization of patients into "low level" or "high level" for each of said specific proteins is preferably determined by listing of all available levels for that respective specific protein in the blood plasma, then determining the median from this listing of said specific protein level values in said blood plasma, and taking this median value as the threshold. This threshold is preferably also referred to herein as median threshold. Preferably, the blood plasma sampling and/or the evaluation of the median value for the respective specific protein is performed prior to treatment of the respective bone metastasis disease with said at least one pan αv integrin inhibitor. Preferably, patients are classified as "high level" if their respective specific protein level in said blood plasma is higher than the median threshold. Accordingly, patients are preferably classified as "low level" if their respective specific protein level in said blood plasma is lower than or equal to said median threshold. Preferably, the respective bone metastasis disease in this regard is metastatic prostate cancer, more preferably metastatic castration-resistant prostate cancer (mCRPC). Preferably, the at least one pan αv integrin inhibitor comprises Abituzumab or Intetumumab). More preferably, the at least one pan αv integrin inhibitor is Abituzumab or Intetumumab. Especially preferred, the at least one pan αv integrin inhibitor is Abituzumab.

Methods to determine said threshold level and especially said median threshold level are known in the art. Examples of suitable technologies include, but are not limited to the SomaLogic technology, preferably the SomaLogic Proteomic Affinity Assay technology, SomaLogic SOMAscan™/V3/Version 10.5.1.1, ELISA (Enzyme-Linked Immuno-Sorbent Assays) technologies and variants thereof, including the RIA (Radio Immuno Assay) technology as high sensitivity variant, the 2D SDS-Polyacryamid electrophorese (SDS-PAGE) Mass Spectrometry technology, and Proximity Ligation Assay (PLA) technologies.

More specifically, the threshold for classification of patients into the 'high' and 'low' groups on the basis of plasma levels of the mentioned proteins is preferably the median plasma level across the patient population. The threshold may show a slight, but irrelevant dependency from the actual technology employed.

Preferably, protein plasma levels of samples that are to be classified are measured using the SomaLogic technology, preferably the SomaLogic Proteomic Affinity Assay technology (Somalogic, Inc., 2945 Wilderness Pl, Boulder, Colo. 80301, USA, software package and version number as described herein) as described herein. The median plasma levels that are accordingly identified can be used as threshold for classification into 'low' and 'high' categories, preferably after the new SomaLogic patient profile is processed with data normalization steps, such as it has been performed in the analysis described herein. For example, the patient's pre-treatment proteomic profiles on 888 plasma protein levels -as it is prepared by the SomaLogic system-can advantageously be combined with existing pre-treatment data set for all samples, variance stabilization as implemented in the vsn2 package which was applied. Finally, the normalized patient's pre-treatment level for the specific protein of interest (median thresholds for predicitivity for radiologic PFS—MAPK11: 9.46, STX1A: 9.06, MAP2K2: 11.9, TNFRSF17: 12.5, RGMB: 11.0, LEPR:11.2, IL1B: 11.1, ICAM3:10.4, F5:15.7, ANG:12.5, PIGR:12.6, TEK: 11.3; all median thresholds are given as protein level units on a log2 scale as measured by Somalogic technology and after variance-stabilizing normalization of the data set) as received from the clinical study described herein (PERSEUS study). In case no prior data set is available, or the technology to measure the plasma protein levels is not the SomaLogic technology, the median population plasma level—as it comes from the new technology or the new patient population (that preferably comprises at least 120 patients for the respective indication) is preferably termed first, then classification can be readily done on the basis of the new population median.

Especially preferably, patients are classified as "high level" if their respective specific protein level in said blood plasma is at least 2% higher, more preferably at least 5% higher, even more preferably at least 10% higher and especially at least 25% higher than said median threshold for the respective specific protein.

Especially preferably, patients are classified as "low level" if their respective specific protein level in said blood plasma is at least 2% lower, more preferably at least 5% lower, even more preferably at least 10% lower and especially at least 25% lower than said median threshold for the respective specific protein.

Preferably, said specific proteins according to the invention comprise a) one or more proteins, selected from the group consisting of
  DCN (Somamer ID: SL004081; UniProt ID: P07585),
  F5 (Somamer ID: SL000622; UniProt ID: P12259),
  ICAM3 (Somamer ID: SL003178; UniProt ID: P32942),
  PIGR (Somamer ID: SL005797; UniProt ID: P01833),
  STK17B (Somamer ID: SL016566; UniProt ID: O94768),
  STX1A (Somamer ID: SL004304; UniProt ID: Q16623), and
  TEK (Somamer ID: SL003200; UniProt ID: Q02763),
  and/or
b) one or more proteins, selected from the group consisting of
  ANG (Somamer ID: SL000003; UniProt ID: P03950),
  IL1B (Somamer ID: SL001795; UniProt ID: P01584),
  LEPR (Somamer ID: SL003184; UniProt ID: P48357),
  MAP2K2 (Somamer ID: SL010501; UniProt ID: P36507), MAPK11 (Somamer ID: SL007453; UniProt ID: Q15759),
RGMB (Somamer ID: SL010468; UniProt ID: Q6NW40), and
TNFRSF17 (Somamer ID: SL004672; UniProt ID: Q02223)
and/or preferably also proteins having at least 80%, more preferably at least 90%, even more preferably at least 95% and especially at least 99% sequence homology to said specific proteins.

More preferably, said specific proteins according to the invention comprise a) one or more proteins, selected from the group consisting of
F5 (Somamer ID: SL000622; UniProt ID: P12259),
ICAM3 (Somamer ID: SL003178; UniProt ID: P32942),
PIGR (Somamer ID: SL005797; UniProt ID: P01833),
STX1A (Somamer ID: SL004304; UniProt ID: Q16623), and
TEK (Somamer ID: SL003200; UniProt ID: Q02763), and/or b) one or more proteins, selected from the group consisting of
ANG (Somamer ID: SL000003; UniProt ID: P03950),
ID B (Somamer ID: SL001795; UniProt ID: P01584),
LEPR (Somamer ID: SL003184; UniProt ID: P48357),
MAP2K2 (Somamer ID: SL010501; UniProt ID: P36507),
MAPK11 (Somamer ID: SL007453; UniProt ID: Q15759),
RGMB (Somamer ID: SL010468; UniProt ID: Q6NW40), and
TNFRSF17 (Somamer ID: SL004672; UniProt ID: Q02223)
and/or preferably also proteins having at least 80%, more preferably at least 90%, even more preferably at least 95% and especially at least 99% sequence homology to said specific proteins.

More preferably, a high level as defined herein for one or more specific proteins in the respective body fluid, preferably in the blood plasma, of the patient is advantageous with respect to the clinical outcome, if said high level of said one or more specific proteins in said body fluid comprises one or more of the proteins selected from the group consisting of
DCN (Somamer ID: SL004081; UniProt ID: P07585),
F5 (Somamer ID: SL000622; UniProt ID: P12259),
ICAM3 (Somamer ID: SL003178; UniProt ID: P32942),
PIGR (Somamer ID: SL005797; UniProt ID: P01833),
STK17B (Somamer ID: SL016566; UniProt ID: Q94768),
STX1A (Somamer ID: SL004304; UniProt ID: Q16623), and
TEK (Somamer ID: SL003200; UniProt ID: Q02763),
even more preferably one or more of the proteins selected from the group consisting of
F5 (Somamer ID: SL000622; UniProt ID: P12259),
ICAM3 (Somamer ID: SL003178; UniProt ID: P32942),
PIGR (Somamer ID: SL005797; UniProt ID: P01833),
STX1A (Somamer ID: SL004304; UniProt ID: Q16623), and
TEK (Somamer ID: SL003200; UniProt ID: Q02763),
and/or preferably also proteins having at least 80%, more preferably at least 90%, even more preferably at least 95% and especially at least 99% sequence homology to said specific proteins.

More preferably, a low level as defined herein for one or more specific proteins in the respective body fluid, preferably in the blood plasma, of the patient is advantageous with respect to the clinical outcome of the treatment of the respective bone metastasis disease with the at least one pan αv integrin inhibitor, if said low level of said one or more specific proteins in said body fluid comprises one or more of the proteins selected from the group consisting of
ANG (Somamer ID: SL000003; UniProt ID: P03950),
IL1B (Somamer ID: SL001795; UniProt ID: P01584),
LEPR (Somamer ID: SL003184; UniProt ID: P48357),
MAP2K2 (Somamer ID: SL010501; UniProt ID: P36507),
MAPK11 (Somamer ID: SL007453; UniProt ID: Q15759),
RGMB (Somamer ID: SL010468; UniProt ID: Q6NW40), and
TNFRSF17 (Somamer ID: SL004672; UniProt ID: Q02223)
and/or preferably also proteins having at least 80%, more preferably at least 90%, even more preferably at least 95% and especially at least 99% sequence homology to said specific proteins.

DETAILED DESCRIPTION OF THE INVENTION

Figure 1:
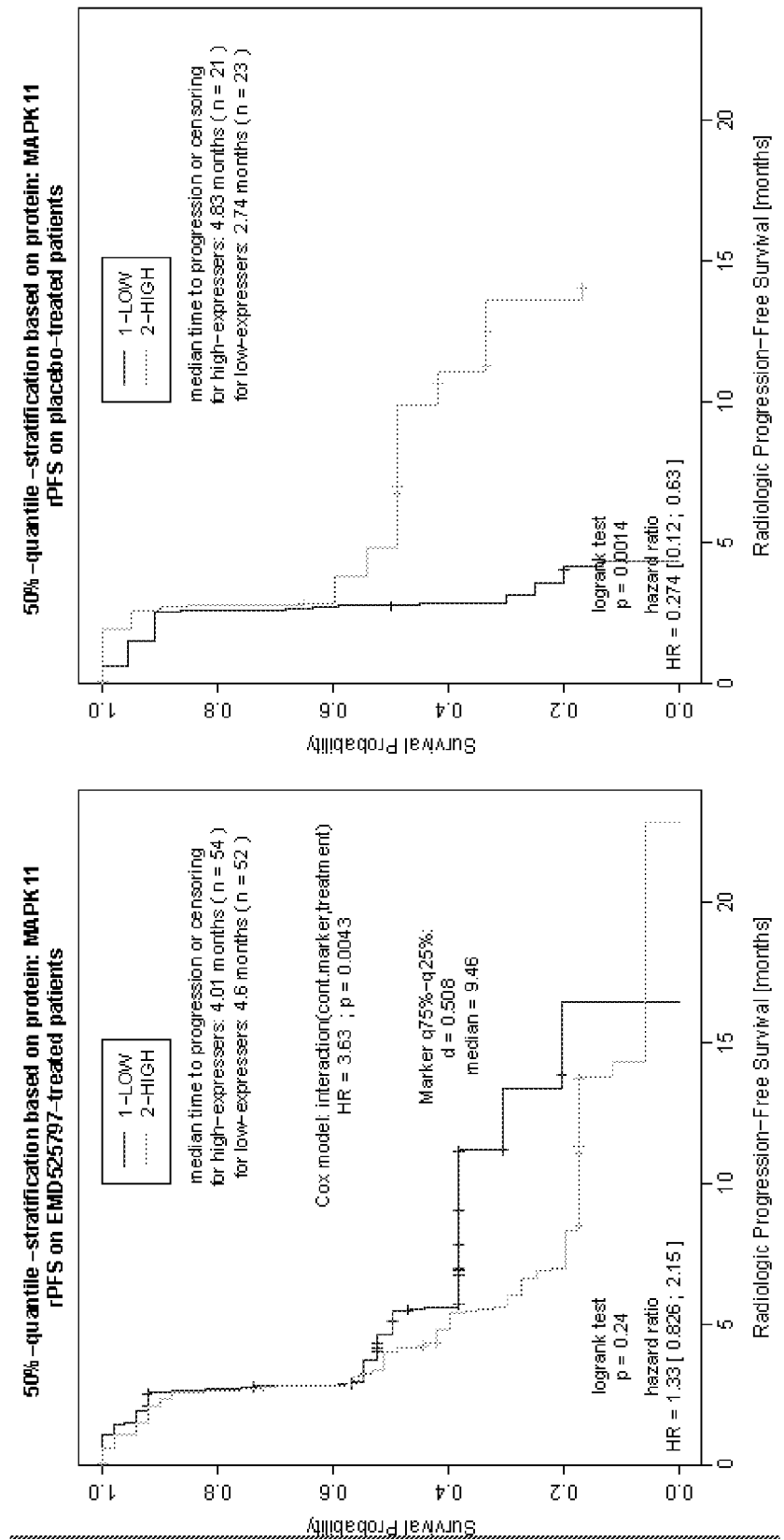
FIG. 1 displays rPFS of patients with high and low expressions of MAPK11 for EMD 525797-treated patients and placebo-treated patients.

Said specific proteins are preferably characterised by the following sequences and /or sequence IDs (Amino acid sequences of protein listed in Table 1 as identified by UniProt IDs in FASTA format):

```
ANG:
>sp|P03950|ANGI_HUMAN Angiogenin OS = Homo sapiens
GN = ANG PE = 1 SV = 1
MVMGLGVLLLVFVLGLGLTPPTLAQDNSRYTHFLTQHYDAKPQGRDDRYC

ESIMRRRGLTSPCKDINTFIHGNKRSIKAICENKNGNPHRENLRISKSSF

QVTTCKLHGGSPWPPCQYRATAGFRNVVVACENGLPVHLDQSIFRRP

DCN:
>sp|P07585|PGS2_HUMAN Decorin OS = Homo sapiens
GN = DCN PE = 1 SV = 1
MKATIILLLLAQVSWAGPFQQRGLFDFMLEDEASGIGPEVPDDRDFEPSL

GPVCPFRCQCHLRVVQCSDLGLDKVPKDLPPDTTLLDLQNNKITEIKDGD

FKNLKNLHALILVNNKISKVSPGAFTPLVKLERLYLSKNQLKELPEKMPK

TLQELRAHENEITKVRKVTFNGLNQMIVIELGTNPLKSSGIENGAFQGMK

KLSYIRIADTNITSIPQGLPPSLTELHLDGNKISRVDAASLKGLNNLAKL

GLSFNSISAVDNGSLANTPHLRELHLDNNKLTRVPGGLAEHKYIQVVYLH

NNNISVVGSSDFCPPGHNTKKASYSGVSLFSNPVQYWEIQPSTFRCVYVR

SAIQLGNYK

F5:
>sp|P12259|FA5_HUMAN Coagulation factor V
OS = Homo sapiens GN = F5 PE = 1 SV = 4
MFPGCPRLWVLVVLGTSVGWGSQGTEAAQLRQFYVAAQGISWSYRPEPT

NSSLNLSVTSFKKIVYREYEPYFKKEKPQSTISGLLGPTLYAEVGDIIKV
```

```
-continued
HFKNKADKPLSIHPQGIRYSKLSEGASYLDHTFPAEKMDDAVAPGREYTY

EWSISEDSGPTHDDPPCLTHIYYSHENLIEDFNSGLIGPLLICKKGTLTE

GGTQKTFDKQIVLLFAVFDESKSWSQSSSLMYTVNGYVNGTMPDITVCAH

DHISWHLLGMSSGPELFSIHFNGQVLEQNHHKVSAITLVSATSTTANMTV

GPEGKWIISSLTPKHLQAGMQAYIDIKNCPKKTRNLKKITREQRRHMKRW

EYFIAAEEVIWDYAPVIPANMDKKYRSQHLDNFSNQIGKHYKKVMYTQYE

DESFTKHTVNPNMKEDGILGPIIRAQVRDTLKIVFKNMASRPYSIYPHGV

TFSPYEDEVNSSFTSGRNNTMIRAVQPGETYTYKWNILEFDEPTENDAQC

LTRPYYSDVDIMRDIASGLIGLLLICKSRSLDRRGIQRAADIEQQAVFAV

FDENKSWYLEDNINKFCENPDEVKRDDPKFYESNIMSTINGYVPESITTL

GFCFDDTVQWHFCSVGTQNEILTIHFTGHSFIYGKRHEDTLTLFPMRGES

VTVTMDNVGTWMLTSMNSSPRSKKLRLKFRDVKCIPDDDEDSYEIFEPPE

STVMATRKMHDRLEPEDEESDADYDYQNRLAAALGIRSFRNSSLNQEEEE

FNLTALALENGTEFVSSNTDIIVGSNYSSPSNISKFTVNNLAEPQKAPSH

QQATTAGSPLRHLIGKNSVLNSSTAEHSSPYSEDPIEDPLQPDVTGIRLL

SLGAGEFKSQEHAKHKGPKVERDQAAKHRFSWMKLLAHKVGRHLSQDTGS

PSGMRPWEDLPSQDTGSPSRMRPWKDPPSDLLLLKQSNSSKILVGRWHLA

SEKGSYEIIQDTDEDTAVNNWLISPQNASRAWGESTPLANKPGKQSGHPK

FPRVRHKSLQVRQDGGKSRLKKSQFLIKTRKKKKEKHTHHAPLSPRTFHP

LRSEAYNTFSERRLKHSLVLHKSNETSLPTDLNQTLPSMDFGWIASLPDH

NQNSSNDTGQASCPPGLYQTVPPEEHYQTFPIQDPDQMHSTSDPSHRSSS

PELSEMLEYDRSHKSFPTDISQMSPSSEHEVWQTVISPDLSQVTLSPELS

QTNLSPDLSHTTLSPELIQRNLSPALGQMPISPDLSHTTLSPDLSHTTLS

LDLSQTNLSPELSQTNLSPALGQMPLSPDLSHTTLSLDFSQTNLSPELSH

MTLSPELSQTNLSPALGQMPISPDLSHTTLSLDFSQTNLSPELSQTNLSP

ALGQMPLSPDPSHTTLSLDLSQTNLSPELSQTNLSPDLSEMPLFADLSQI

PLTPDLDQMTLSPDLGETDLSPNFGQMSLSPDLSQVTLSPDISDTTLLPD

LSQISPPPDLDQIFYPSESSQSLLLQEFNESFPYPDLGQMPSPSSPTLND

TFLSKEFNPLVIVGLSKDGTDYIEIIPKEEVQSSEDDYAEIDYVPYDDPY

KTDVRTNINSSRDPDNIAAWYLRSNNGNRRNYYIAAEEISWDYSEFVQRE

TDIEDSDDIPEDTTYKKVVFRKYLDSTFTKRDPRGEYEEHLGILGPIIRA

EVDDVIQVRFKNLASRPYSLHAHGLSYEKSSEGKTYEDDSPEWFKEDNAV

QPNSSYTYVWHATERSGPESPGSACRAWAYYSAVNPEKDIHSGLIGPLLI

CQKGILHKDSNMPMDMREFVLLFMTFDEKKSWYYEKKSRSSWRLTSSEMK

KSHEFHAINGMIYSLPGLKMYEQEWVRLHLLNIGGSQDIHVVHFHGQTLL

ENGNKQHQLGVWPLLPGSFKTLEMKASKPGWWLLNTEVGENQRAGMQTPF

LIMDRDCRMPMGLSTGIISDSQIKASEFLGYWEPRLARLNNGGSYNAWSV

EKLAAEFASKPWIQVDMQKEVIITGIQTQGAKHYLKSCYTTEFYVAYSSN

QINWQIFKGNSTRNVMYFNGNSDASTIKENQFDPPIVARYIRISPTRAYN

RPTLRLELQGCEVNGCSTPLGMENGKIENKQITASSFKKSWWGDYWEPFR

ARLNAQGRVNAWQAKANNNKQWLEIDLLKIKKITAIITQGCKSLSSEMYV
```

```
KSYTIHYSEQGVEWKPYRLKSSMVDKIFEGNTNTKGHVKNFFNPPIISRF

IRVIPKTWNQSIALRLELFGCDIY

ICAM3:
>sp|P32942|ICAM3_HUMAN Intercellular adhesion
molecule 3 OS = Homo sapiens GN = ICAM3 PE = 1
SV = 2
MATMVPSVLWPRACWTLLVCCLLTPGVQGQEFLLRVEPQNPVLSAGGSLF

VNCSTDCPSSEKIALETSLSKELVASGMGWAAFNLSNVTGNSRILCSVYC

NGSQITGSSNITVYRLPERVELAPLPPWQPVGQNFTLRCQVEDGSPRTSL

TVVVLLRWEEELSRQPAVEEPAEVTATVLASRDDHGAPFSCRTELDMQPQG

LGLFVNTSAPRQLRTFVLPVTPPRLVAPRFLEVETSWPVDCTLDGLFPAS

EAQVYLALGDQMLNATVMNHGDTLTATATATARADQEGAREIVCNVTLGG

ERREARENLTVFSFLGPIVNLSEPTAHEGSTVTVSCMAGARVQVTLDGVP

AAAPGQPAQLQLNATESDDGRSFFCSATLEVDGEFLHRNSSVQLRVLYGP

KIDRATCPQHLKWKDKTRHVLQCQARGNPYPELRCLKEGSSREVPVGIPF

FVNVTHNGTYQCQASSSRGKYTLVVVMDIEAGSSHFVPVFVAVLLTLGVV

TIVLALMYVFREHQRSGSYHVREESTYLPLTSMQPTEAMGEEPSRAE

IL1B:
>sp|P01584|IL1B_HUMAN Interleukin-1 beta OS = Homo
sapiens GN = IL1B PE = 1 SV = 2
MAEVPELASEMMAYYSGNEDDLFFEADGPKQMKCSFQDLDLCPLDGGIQL

RISDHHYSKGFRQAASVVVAMDKLRKMLVPCPQTFQENDLSTFFPFIFEE

EPIFFDTWDNEAYVHDAPVRSLNCTLRDSQQKSLVMSGPYELKALHLQGQ

DMEQQVVFSMSFVQGEESNDKIPVALGLKEKNLYLSCVLKDDKPTLQLES

VDPKNYPKKKMEKRFVFNKIEINNKLEFESAQFPNWYISTSQAENMPVFL

GGTKGGQDITDFTMQFVSS

LEPR:
>sp|P48357|LEPR_HUMAN Leptin receptor OS = Homo
sapiens GN = LEPR PE = 1 SV = 2
MICQKFCVVLLHWEFIYVITAFNLSYPITPWRFKLSCMPPNSTYDYFLLP

AGLSKNTSNSNGHYETAVEPKFNSSGTHFSNLSKTTFHCCFRSEQDRNCS

LCADNIEGKTFVSTVNSLVFQQIDANWNIQCWLKGDLKLFICYVESLFKN

LFRNYNYKVHLLYVLPEVLEDSPLVPQKGSFQMVHCNCSVHECCECLVPV

PTAKLNDTLLMCLKITSGGVIFQSPLMSVQPINMVKPDPPLGLHMEITDD

GNLKISWSSPPLVPFPLQYQVKYSENSTTVIREADKIVSATSLLVDSILP

GSSYEVQVRGKRLDGPGIWSDWSTPRVFTTQDVIYFPPKILTSVGSNVSF

HCIYKKENKIVPSKEIVWWMNLAEKIPQSQYDVVSDHVSKVTFFNLNETK

PRGKFTYDAVYCCNEHECHHRYAELYVIDVNINISCETDGYLTKMTCRWS

TSTIQSLAESTLQLRYHRSSLYCSDIPSIHPISEPKDCYLQSDGFYECIF

QPIFLLSGYTMWIRINHSLGSLDSPPTCVLPDSVVKPLPPSSVKAEITIN

IGLLKISWEKPVFPENNLQFQIRYGLSGKEVQWKMYEVYDAKSKSVSLPV

PDLCAVYAVQVRCKRLDGLGYWSNWSNPAYTVVMDIKVPMRGPEFWRIIN

GDTMKKEKNVTLLWKPLMKNDSLCSVQRYVINHHTSCNGTWSEDVGNHTK

FTFLWTEQAHTVTVLAINSIGASVANFNLTFSWPMSKVNIVQSLSAYPLN

SSCVIVSWILSPSDYKLMYFIIEWKNLNEDGEIKWLRISSSVKKYYIHDH

FIPIEKYQFSLYPIFMEGVGKPKIINSFTQDDIEKHQSDAGLYVIVPVII
```

```
SSSILLLGTLLISHQRMKKLFWEDVPNPKNCSWAQGLNFQKPETFEHLFI

KHTASVTCGPLLLEPETISEDISVDTSWKNKDEMMPTTVVSLLSTTDLEK

GSVCISDQFNSVNFSEAEGTEVTYEDESQRQPFVKYATLISNSKPSETGE

EQGLINSSVTKCFSSKNSPLKDSFSNSSWEIEAQAFFILSDQHPNIISPH

LTFSEGLDELLKLEGNFPEENNDKKSIYYLGVTSIKKRESGVLLTDKSRV

SCPFPAPCLFTDIRVLQDSCSHFVENNINLGTSSKKTFASYMPQFQTCST

QTHKIMENKMCDLTV

MAP2K2
>sp|P36507|MP2K2_HUMAN Dual specificity mitogen-
activated protein kinase kinase 2 OS = Homo
sapiens GN = MAP2K2 PE = 1 SV = 1
MLARRKPVLPALTINPTIAEGPSPTSEGASEANLVDLQKKLEELELDEQQ

KKRLEAFLTQKAKVGELKDDDFERISELGAGNGGVVTKVQHRPSGLIMAR

KLIHLEIKPAIRNQIIRELQVLHECNSPYIVGFYGAFYSDGEISICMEHM

DGGSLDQVLKEAKRIPEEILGKVSIAVLRGLAYLREKHQIMHRDVKPSNI

LVNSRGEIKLCDFGVSGQLIDSMANSFVGTRSYMAPERLQGTHYSVQSDI

WSMGLSLVELAVGRYPIPPPDAKELEAIFGRPVVDGEEGEPHSISPRPRP

PGRPVSGHGMDSRPAMAIFELLDYIVNEPPPKLPNGVFTPDFQEFVNKCL

IKNPAERADLKMLTNHTFIKRSEVEEVDFAGWLCKTLRLNQPGTPTRTAV

MAPK11
>sp|Q15759|MK11_HUMAN Mitogen-activated protein
kinase 11 OS = Homo sapiens GN = MAPK11 PE = 1
SV = 2
MSGPRAGFYRQELNKTVWEVPQRLQGLRPVGSGAYGSVCSAYDARLRQKV

AVKKLSRPFQSLIHARRTYRELRLLKHLKHENVIGLLDVFTPATSIEDFS

EVYLVTTLMGADLNNIVKCQALSDEHVQFLVYQLLRGLKYIHSAGIIHRD

LKPSNVAVNEDCELRILDFGLARQADEEMTGYVATRWYRAPEIMLNWMHY

NQTVDIWSVGCIMAELLQGKALFPGSDYIDQLKRIMEVVGTPSPEVLAKI

SSEHARTYIQSLPPMPQKDLSSIFRGANPLAIDLLGRMLVLDSDQRVSAA

EALAHAYFSQYHDPEDEPEAEPYDESVEAKERTLEEWKELTYQEVLSFKP

PEPPKPPGSLEIEQ

PIGR:
>sp|P01833|PIGR_HUMAN Polymeric immunoglobulin
receptor OS = Homo sapiens GN = PIGR PE = 1 SV = 4
MLLFVLTCLLAVFPAISTKSPIFGPEEVNSVEGNSVSITCYYPPTSVNRH

TRKYWCROGARGGCITLISSEGYVSSKYAGRANLTNFPENGTFVVNIAQL

SQDDSGRYKCGLGINSRGLSFDVSLEVSQGPGLLNDTKVYTVDLGRTVTI

NCPFKTENAQKRKSLYKOIGLYPVLVIDSSGYVNPNYTGRIRLDIQGTGQ

LLFSVVINQLRLSDAGQYLCOAGDDSNSNKKNADLQVLKPEPELVYEDLR

GSVTFHCALGPEVANVAKFLCRQSSGENCDVVVNTLGKRAPAFEGRILLN

PQDKDGSFSVVITGLRKEDAGRYLCGAHSDGQLQEGSPIQAWQLFVNEES

TIPRSPTVVKGVAGGSVAVLCPYNRKESKSIKYWCLWEGAQNGRCPLLVD

SEGWVKAQYEGRLSLLEEPGNGTFTVILNQLTSRDAGFYWCLTNGDTLWR

TTVEIKIIEGEPNLKVPGNVTAVLGETLKVPCHFPCKFSSYEKYWCKWNN

TGCQALPSQDEGPSKAFVNCDENSRLVSLTLNLVTRADEGWYWCGVKQGH

FYGETAAVYVAVEERKAAGSRDVSLAKADAAPDEKVLDSGFREIENKAIQ
```

-continued
DPRLFAEEKAVADTRDQADGSRASVDSGSSEEQGGSSRALVSTLVPLGLV

LAVGAVAVGVARARHRKNVDRVSIRSYRTDISMSDFENSREFGANDNMGA

SSITQETSLGGKEEFVATTESTTETKEPKKAKRSSKEEAEMAYKDFLLQS

STVAAEAQDGPQEA

RGMB:
>sp|Q6NW40|RGMB_HUMAN RGM domain family member B
OS = Homo sapiens GN = RGMB PE = 1 SV = 3
MGLRAAPSSAAAAAAEVEQRRSPGLCPPPLELLLLLLFSLGLLHAGDCQQ

PAQCRIQKCTTDFVSLTSHLNSAVDGFDSEFCKALRAYAGCTQRTSKACR

GNLVYHSAVLGISDLMSQRNCSKDGPTSSTNPEVTHDPCNYHSHAGAREH

RRGDONPPSYLFCGLFGDPHLRTFKDNFQTCKVEGAWPLIDNNYLSVQVT

NVPVVPGSSATATNKITIIFKAHHECTDQKVYQAVTDDLPAAFVDGTTSG

GDSDAKSLRIVERESGHYVEMHARYIGTTVFVRQVGRYLTLAIRMPEDLA

MSYEESQDLQLCVNGCPLSERIDDGQGQVSAILGHSLPRTSLVQAWPGYT

LETANTQCHEKMPVKDIYFQSCVFDLLTTGDANFTAAAHSALEDVEALHP

RKERWHIFPSSGNGTPRGGSDLSVSLGLTCLILIVFL

STK17B:
>sp|O94768|ST17B_HUMAN Serine/threonine-protein
kinase 17B OS = Homo sapiens GN = STK17B PE = 1
SV = 1
MSRRRFDCRSISGLLTTTPQIPIKMENFNNFYILTSKELGRGKFAVVRQC

ISKSTGQEYAAKFLKKRRRGQDCRAEILHEIAVLELAKSCPRVINLHEVY

ENTSEIILILEYAAGGEIFSLCLPELAEMVSENDVIRLIKQILEGVYYLH

QNNIVHLDLKPQNILLSSIYPLGDIKIVDFGMSRKIGHACELREIMGTPE

YLAPEILNYDPITTATDMWNIGIIAYMLLTHTSPFVGEDNQETYLNISQV

NVDYSEETFSSVSQLATDFIQSLLVKNPEKRPTAEICLSHSWLQQWDFEN

LFHPEETSSSSQTQDHSVRSSEDKTSKSSCNGTCGDREDKENIPEDSSMV

SKRFRFDDSLPNPHELVSDLLC

STX1A:
>sp|Q16623|STX1A_HUMAN Syntaxin-1A OS = Homo
sapiens GN = STX1A PE = 1 SV = 1
MKDRTQELRTAKDSDDDDDVAVTVDRDRFMDEFFEQVEEIRGFIDKIAEN

VEEVKRKHSAILASPNPDEKTKEELEELMSDIKKTANKVRSKLKSIEQSI

EQEEGLNRSSADLRIRKTQHSTLSRKFVEVMSEYNATQSDYRERCKGRIQ

RQLEITGRTTTSEELEDMLESGNPAIFASGIIMDSSISKQALSEIETRHS

EIIKLENSIRELHDMFMDMAMLVESQGEMIDRIEYNVEHAVDYVERAVSD

TKKAVKYQSKARRKKIMIIICCVILGIVIASTVGGIFA

TEK:
>sp|Q02763|TIE2_HUMAN Angiopoietin-1 receptor
OS = Homo sapiens GN = TEK PE = 1 SV = 2
MDSLASLVLCGVSLLLSGTVEGAMDLILINSLPLVSDAETSLTCIASGWR

PHEPITIGRDFEALMNQHQDPLEVTQDVTREWAKKVVWKREKASKINGAY

FCEGRVRGEAIRIRTMKMRQQASFLPATLTMTVDKGDNVNISFKKVLIKE

EDAVIYKNGSFIHSVPRHEVPDILEVHLPHAQPQDAGVYSARYIGGNLFT

SAFTRLIVRRCEAQKWGPECNHLCTACMNNGVCHEDTGECICPPGFMGRT

CEKACELHTFGRTCKERCSGQEGCKSYVFCLPDPYGCSCATGWKGLQCNE

ACHPGFYGPDCKLRCSCNNGEMCDRFQGCLCSPGWQGLQCEREGIQRMTP

-continued
KIVDLPDHIEVNSGKFNPICKASGWPLPTNEEMTLVKPDGTVLHPKDFNH

TDHFSVAIFTIHRILPPDSGVWVCSVNTVAGMVEKPFNISVKVLPKPLNA

PNVIDTGHNFAVINISSEPYFGDGPIKSKKLLYKPVNHYEAWQHIQVTNE

IVTLNYLEPRTEYELCVQLVRRGEGGEGHPGPVRRFTTASIGLPPPRGLN

LLPKSQTTLNLTWQPIFPSSEDDFYVEVERRSVQKSDQQNIKVPGNLTSV

LLNNLHPREQYVVRARVNTKAQGEWSEDLTAWTLSDILPPQPENIKISNI

THSSAVISWTILDGYSISSITIRYKVQGKNEDQHVDVKIKNATITQYQLK

GLEPETAYQVDIFAENNIGSSNPAFSHELVTLPESQAPADLGGGKMLLIA

ILGSAGMTCLTVLLAFLIILQLKRANVQRRMAQAFQNVREEPAVQFNSGT

LALNRKVKNNPDPTIYPVLDWNDIKFQDVIGEGNFGQVLKARIKKDGLRM

DAAIKRMKEYASKDDHRDFAGELEVLCKLGHHPNIINLLGACEHRGYLYL

AIEYAPHGNLLDFLRKSRVLETDPAFAIANSTASTLSSQQLLHFAADVAR

GMDYLSQKQFIHRDLAARNILVGENYVAKIADFGLSRGQEVYVKKTMGRL

PVRWMAIESLNYSVYTTNSDVWSYGVLLWEIVSLGGTPYCGMTCAELYEK

LPQGYRLEKPLNCDDEVYDLMRQCWREKPYERPSFAQILVSLNRMLEERK

TYVNTTLYEKFTYAGIDCSAEEAA

TNFRSF17:
>sp|Q02223|TNR17_HUMAN Tumor necrosis factor
receptor superfamily member 17 OS = Homo sapiens
GN = TNFRSF17 PE = 1 SV = 2
MLQMAGQCSQNEYFDSLLHACIPCQLRCSSNTPPLTCQRYCNASVTNSVK

GTNAILWTCLGLSLIISLAVFVLMFLLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKSISAR

Specific proteins according to the invention are preferably also proteins having at least 80%, more preferably at least 90%, even more preferably at least 95% and especially at least 99% sequence homology to the afore described sequences.

As further described herein, a high level of one or more proteins of a first group of said specific proteins and/or a low level of one or more proteins from a second group of specific proteins is predictive for improved clinical benefit, preferably clinical benefit as described herein, under treatment with at least one pan αv integrin inhibitor, preferably including or consisting of Abituzumab, for subjects suffering from a bone metastasis disease, including but not limited to metastatic prostate cancer, and metastatic castration-resistant prostate cancer (mCRPC). Preferably, a high level of one or more proteins of a first group of said specific proteins and/or a low level of one or more proteins from a second group of specific proteins is predictive for improved overall survival and/or improved progression free survival, under treatment with at least one pan αv integrin inhibitor, preferably including or consisting of Abituzumab, for subjects suffering from a bone metastasis disease, including but not limited to metastatic prostate cancer, and metastatic castration-resistant prostate cancer (mCRPC).

In an alternatively preferred embodiment, Intetumumab (CNTO-95) can be employed as the at least one pan αv integrin inhibitor in the method according to the invention, instead of Abituzumab.

Said protein levels for said specific proteins are preferably at the same time negative prognostic indicating that the biologically addressed by the markers plays a role both for disease prognosis (summarized in Table 2).

TABLE 1

Clinical outcome dependent on the respective specific protein level under Abituzumab treatment:

| Gene symbol (Somamer ID) | UniProt ID | Patients with benefit have High(er) or Low(er) plasma levels compared to median | Hazard Ratio (HR) of progression-free survival (PFS) [CI 95%] | Logrank test p-value |
|---|---|---|---|---|
| ANG (SL000003) | P03950 | Low | 0.500 [0.272-0.916] | 0.03 |
| DCN (SL004081) | P07585 | High | 0.443 [0.235-0.832] | 0.015 |
| F5 (SL000622) | P12259 | High | 0.416 [0.219-0.790] | 0.01 |
| ICAM3 (SL003178) | P32942 | High | 0.427 [0.239-0.766] | 0.0059 |
| IL1B (SL001795) | P01584 | Low | 0.498 [0.279-0.891] | 0.022 |
| LEPR (SL003184) | P48357 | Low | 0.389 [0.211-0.717] | 0.0033 |
| MAP2K2 (SL010501) | P36507 | Low | 0.397 [0.224-0.702] | 0.0023 |
| MAPK11 (SL007453) | Q15759 | Low | 0.321 [0.171-0.603] | 0.00058 |
| PIGR (SL005797) | P01833 | High | 0.311 [0.166-0.582] | 0.00046 |
| RGMB (SL010468) | Q6NW40 | Low | 0.457 [0.256-0.813] | 0.0093 |
| STK17B (SL016566) | O94768 | High | 0.380 [0.193-0.747] | 0.0078 |
| STX1A (SL004304) | Q16623 | High | 0.250 [0.131-0.476] | 0.000032 |
| TEK (SL003200) | Q02763 | High | 0.508 [0.280-0.920] | 0.03 |
| TNFRSF17 (SL004672) | Q02223 | Low | 0.471 [0.265-0.836] | 0.012 |

TABLE 2

Clinical outcome, preferably determined by radiologic PFS (rPFS) dependent on the respective specific protein level under SoC treatment:

| Gene symbol (Somamer ID) | UniProt ID | High levels indicate (g)ood, or (p)oor prognosis under SOC [HR] |
|---|---|---|
| ANG (SL000003) | P03950 | Good [0.698] |
| DCN (SL004081) | P07585 | Poor [1.5] |
| F5 (SL000622) | P12259 | Poor [2.11] |
| ICAM3 (SL003178) | P32942 | Poor [2.60] |
| IL1B (SL001795) | P01584 | Good [0.43] |
| LEPR (SL003184) | P48357 | Good [0.419] |
| MAP2K2 (SL010501) | P36507 | Good [0.346] |
| MAPK11 (SL007453) | Q15759 | Good [0.274] |
| PIGR (SL005797) | P01833 | Poor [3.44] |
| RGMB (SL010468) | Q6NW40 | Good [0.393] |
| STK17B (SL016566) | O94768 | Poor [4.40] |
| STX1A (SL004304) | Q16623 | Poor [3.77] |
| TEK (SL003200) | Q02763 | Poor [1.95] |
| TNFRSF17 (SL004672) | Q02223 | Good [0.425] |

The clinical outcome of patients having tumors and/or metastases (both preferably also referred to as tumour lesions or lesions) is preferably analysed according to response (complete and partial), benefit (response and stable disease), and progressive disease. Lesions are preferably evaluated using Response Evaluation Criteria in Solid Tumors (i.e. RECIST criteria) whereby "complete response" (CR) is preferably defined as the disappearance of the target lesions; "partial response" (PR) is preferably defined as at least a 30% decrease in the sum of the longest iron metre of target lesions, preferably taking as reference the baseline sum longest diameter; "progressive disease" (PD) is preferably defined as at least a 20% increase in the sum of the longest diameter of target lesions, preferably taking as reference the smallest sum longest diameter recorded since the treatment started or the appearance of one or more new lesions; and "stable disease" (SD) is preferably defined as neither sufficient shrinkage to qualify for partial response nor sufficient increased to qualify for progressive disease, preferably taking as reference the smallest sum longest diameter since the treatment started.

Preferably, the at least one pan αv integrin inhibitor, preferably Abituzumab or Intetumumab (CNTO-95), is administered to said subject in combination with one or more chemotherapeutic agents.

Treatment of prostate cancer and/or metastases thereof may involve surgery (e.g. radical prostatectomy), radiation therapy including brachytherapy (prostate brachytherapy) and external beam radiation therapy, high-intensity focused ultrasound (HIFU), chemotherapy, oral chemotherapeutic drugs (Temozolomide/TMZ), cryosurgery, hormonal therapy, or combinations thereof.

Most hormone dependent cancers become refractory after one to three years and resume growth despite hormone therapy. Previously considered "hormone-refractory prostate cancer" or "androgen-independent prostate cancer", the term castration-resistant has replaced "hormone refractory" because while they are no longer responsive to castration treatment (reduction of available androgen/testosterone/DHT by chemical or surgical means), these cancers still show reliance upon hormones for androgen receptor activation. However, there are now several chemotherapeutic treatments available to treat CRPC that improve survival.

Chemotherapeutics in this respect preferably include, but are not limited to docetaxel, cabazitaxel, bevacizumab, docetaxel, thalidomide and prednisone, and combinations thereof. E.g., a combination of bevacizumab, docetaxel, thalidomide and prednisone has shown clinical benefits.

Chemotherapeutics in this respect preferably also include, but are not limited to, cetuximab, Panitumumab, irinotecan, vinorelbine, capecitabine, leucovorine, oxaliplatin, cisplatin, carboplatin, 5-fluorouracil (5-FU), bevacizumab, aflibercept and regorafenib.

More preferably, one or more chemotherapeutic agents, even more preferably two or more and especially one, two or three chemotherapeutic agents a) selected from the group consisting of leuproreline acetate, bicalutamide, nilutamide, triptoreline, gosereline, flutamide, cyproterone, busereline and degarelix, b) selected from the group consisting of Zoledronic acid, Pamidronic acid, Clodronate disodium, Alendronic acid and Ibandronic acid, and/or c) selected from the group consisting of Abiraterone, Abiraterone acetate, Prednisone, Enzalutamide, Radium Ra 223 dichloride, Docetaxel, Sipuleucel-T, Cabazitaxel and Mitoxantrone, are employed. This is preferred for subjects suffering from a bone metastasis disease, more preferred for subjects suffering from metastatic prostate cancer, and especially for subjects suffering from metastatic castration-resistant prostate cancer (mCRPC).

A subset of subjects appears to respond to androgen signaling blocking drugs, including, but not limited to Luteinizing hormone-releasing hormone (LH-RH) agonists and/or antagonists as well as gonadotropin-releasing hormone (GnRH) agonists and/or antagonists. Luteinizing hormone-releasing hormone (LH-RH) as well as gonadotropin-releasing hormone (GnRH) are hormone therapy drugs that lower the production of testosterone in a man's body. This drop in testosterone usually slows or stops the growth of prostate cancer for a period of time. Thus, it is in many cases preferred to administer this class of compounds in connection with treatment with Abituzumab or Intetumumab (CNTO-95).

Further agents that are preferably regarded as chemotherapeutics in the context of the instant invention include sipuleucel-T, abiraterone and Enzalutamide.

Pain is common in metastatic cancers and especially in case of bone metastases thereof. This is also true with prostate cancer, and cancer pain related to bone metastases can be treated with bisphosphonates, medications such as opioids, and palliative radiation therapy to known metastases. Spinal cord compression can occur with metastases to the spine, and can be treated with steroids, surgery, or radiation therapy.

The traditional treatments for cancer are Radiotherapy and chemotherapy, usually in combination with one another. Scientists and pharmaceutical companies are researching drugs to target different types of cancer, including metastatic bone disease.

High-intensity focused ultrasound (HIFU) has CE approval for palliative care for bone metastasis. As an entirely side-effect free and non-invasive treatment, HIFU has been successfully applied in the treatment of cancer to destroy tumours of the bone, brain, breast, liver, pancreas, rectum, kidney, testes, and prostate.

One treatment option for bone metastases that has to be considered is treatment with bisphosphonates, often in combination of other chemotherapeutics and/or (anti-)hormonal treatment. Bisphosphonates have shown great promise in reducing bone cancer pain, bone destruction, and tumor growth.

Monthly injections of radium-223 chloride (as Xofigo, formerly called Alpharadin) have been approved by the FDA in May 2013 for castration-resistant prostate cancer (CRPC) with bone metastases.

Especially preferably, the at least one pan αv integrin inhibitor, preferably Abituzumab or Intetumumab (CNTO-95), more preferably Abituzumab, is administered to said subject in combination with two or more chemotherapeutic agents, preferably referred to as standards of care (SoC).

Preferred standards of care (SoC) include, but are not limited to:

a) at least one LHRH agonist/antagonist, preferably selected from the group consisting of Leuproreline, Leuproreline acetate, bicalutamid, nilutamide, triptoreline, gosereline, flutamide, cyproterone, busereline and degarelix, and/or b) at least one bisphosphonate, preferably selected from the group consisting of Zoledronic acid, Pamidronic acid, Clodronate disodium, Alendronic acid and Ibandronic acid.

More preferred standards of care (SoC) include, but are not limited to:

a) at least one LHRH agonist/antagonist, preferably selected from the group consisting of Leuproreline, Leuproreline acetate, bicalutamid, nilutamide, triptoreline, gosereline, flutamide, cyproterone, busereline and degarelix, and/or the pharmaceutically acceptable derivatives and/or salts thereof; in combination with b) at least one bisphosphonate, preferably selected from the group consisting of Zoledronic acid, Pamidronic acid, Clodronate disodium, Alendronic acid and Ibandronic acid, and/or the pharmaceutically acceptable derivatives and/or salts thereof.

The most preferred standard of care (SoC) includes:

a) Leuproreline, Leuproreline acetate and/or pharmaceutically acceptable derivatives and/or salts thereof, in combination with b) Zoledronic acid and/or pharmaceutically acceptable derivatives and/or salts thereof.

αv integrins are cell adhesion molecules involved in cell survival, proliferation, migration, and angiogenesis; they are deregulated in various cancer types, including prostate cancer (Legate K R, et al. Nat Rev Mol Cell Biol 2006;7:20-31; Guise TA, et al. Clin Cancer Res 2006;12:62135-16s). Abituzumab, a humanized monoclonal IgG2 antibody, inhibits αv-integrins expressed on castrate-resistant prostate cancer (CRPC) cells, tumor vessels, and osteoclasts involved in bone metastasis (Mitjans F, et al. J Cell Sci 1995;108:2825-38; Monnier Y, et al. Cancer Res 2008;68: 7323-31). Abituzumab demonstrated antitumor activity in in vivo CRPC models and was well tolerated in a phase I study in mCRPC patients previously treated with docetaxel (Wirth M, et al. Eur Urol 2014;65:897-904).

In an randomized, double-blind, placebo-controlled, phase II trial, a total of 180 patients were randomized 1:1:1 to receive a) standard of care (SoC), e.g. continuous treatment with a luteinizing hormone-releasing hormone agonist and bisphosphonate treatment, e.g. with Leuproreline or Leuproreline acetate and Zoledronic acid (and/or pharmaceutically acceptable derivatives and/or salts thereof) plus placebo, b) SoC as described under a) plus abituzumab 750 mg, or c) SoC as described under a) plus abituzumab 1,500 mg.

Patients were treated until rPD in bone or soft tissue lesions, skeletal event, death, or unacceptable toxicity; Patients in the placebo arm who had asymptomatic or mildly symptomatic rPD on treatment could crossover to abituzumab 1,500 mg (open-label).

Median PFS with abituzumab 1,500 mg was modestly longer than with abituzumab 750 mg or placebo: 4.3 (95% CI: 2.8-6.6) vs 3.4 (95% CI: 2.8-5.6) and 3.3 (95% CI:

2.8-4.8) months; HR abituzumab 1,500 mg vs placebo: 0.81 (95% CI: 0.52-1.26). Patients receiving abituzumab experienced bone progression less frequently than those receiving placebo (23% of patients receiving abituzumab had bone progression, vs 42% of those receiving SoC).

Blood sampling for plasma protein analyses was scheduled pre-treatment. Plasma protein analyses (based on highly protein-specific aptamers [SomaLogic system]) were performed on samples taken from 150 patients prior to treatment in cycle 1.

The original set of simultaneously determined 1,129 plasma protein levels was restricted to 888 proteins on the data level to avoid potential bias due to cell lysis or platelet activation during plasma preparation. Nine global biomarker search analyses were carried out using different normalization procedures, data sets and biomarker dichotomization thresholds, with the aim of filtering specific proteins that are predictive biomarkers for Abituzumab therapy success. The judgement whether a distinct protein is a predictive biomarker was based on an assessment of outcome (OS or PFS) in dependence of treatment (SoC or Abituzumab) and biomarker levels (continuous levels, and dichotomized categories "high" and "low" using the median of the investigated patient population as a threshold). Statistical tests were carried out per protein to identify those proteins that can be considered as predictive. The statistical tests are prior art and comprised. Among other criteria, logrank tests on selected populations, as for example the biomarker "high" and biomarker "low" populations, for detection of differences in outcome (here OS and/or PFS) for different treatment groups (Abituzumab and SOC; threshold p<=0.05), and Cox regression models investigating dependence of outcome on the interaction effect between treatment and continuous marker levels (interaction term p<=0.05). Further, the prognosticity of the marker levels was assessed on the basis of the patient group receiving SOC therapy using logrank tests (threshold p<=0.05) for the "high" and "low" subgroups.

Said specific proteins include decorin (DCN), a protein known to have a role in TGF-β biology, as do some of the αv integrins inhibited by abituzumab (Munger J S, Sheppard D. Cold Spring Harb Perspect Biol 2011;3:a005017).

Furthermore, analysis of the biological context of other markers indicated that markers related to known molecular interactions of abituzumab (bone metabolism modulation and angiogenesis) appear to predict OS and/or PFS with abituzumab therapy.

Thus, plasma levels of each of the identified biomarker plasma proteins were surprisingly found to be prognostic of poor survival and predicted increased survival and/or progression free survival with abituzumab compared to SoC alone.

Thus, the clinical study delivered data on the pharmacokinetics and immunogenicity of abituzumab, as well as enabled analyses in search of predictive biomarkers, and surprisingly provided specific predictive protein levels in body fluids, especially specific plasma protein levels that allow predicting the therapy outcome under treatment with at least one pan αv integrin inhibitor, preferably including the pan αv integrin inhibitor abituzumab.

Abituzumab is a monoclonal anti-alpha v antibody also designated herein as DI-17E6, DI17E6, EMR62242 and/or EMD 525797). DI17E6 is an engineered specifically tailored IgG2 hybrid monoclonal antibody directed to alpha-v integrin (receptor). Cancer therapy by means of this antibody reduces side effects associated with this type of therapy, above all immune reactions, thereby reducing immunogenicity. The antibody is described in detail in WO 2009/010290, the disclosure of which is incorporated herein in its entirety.

Its hypervariable regions (CDRs) derive from murine mAb 17E6 (EMD 73034). This parent mouse IgG1 antibody is described, for example by Mitjans et al. (1995; J. Cell Sci. 108, 2825) and patents U.S. Pat. No. 5,985,278 and EP 719 859. Mouse mAb 17E6 is produced by hybridoma cell line 272-17E6 and deposited under accession number DSM ACC2160.

Its light chain domains derive from humanized monoclonal anti-EGFR antibody 425 (matuzumab). This antibody is described in detail for example in EP 0 531 47261, and derives from its murine counterpart 425 (mouse MAb 425, ATCC HB9629). The antibody was raised against the human A431 carcinoma cell line and found to bind to a polypeptide epitope on the external domain of the human epidermal growth factor receptor (EGFR). Matuzumab has shown in clinical trials high efficacy.

Generally DI1 7E6 as used according to the invention comprises:
(i) a CDR light and a heavy chain region deriving from mouse monoclonal anti-αv integrin antibody 17E6
(ii) a light chain framework region which is taken from humanized monoclonal anti-EGFR antibody 425,
(iii) a heavy chain framework region deriving from mouse monoclonal anti-αv integrin antibody 17E6, optionally comprising one or more mutations of amino acids at specific positions, and
(iv) a heavy chain constant region deriving from human IgG2 and a human constant kappa light chain region, wherein in said IgG2 domain the IgG2 hinge region was replaced by the human IgG1 hinge domain, and; wherein optionally one or more mutations within the IgG2 has been carried out.

Specifically, DI17E6 (designated as "DI-17E6γ2h (N297Q)" or "EMD 525797") as used for the treatment as claimed and in the clinical trials as described above and below, has the following amino acid sequence:

(i) variable and constant light chain sequences
(SEQ ID No. 1):
DIQMTQSPSSLSASVGDRVTITCRASQDISNYLAWYQQKPGKAPKLLIYYT

SKIHSGVPSRFSGSGSGTDYTFTISSLQPEDIATYYCQQGNTFPYTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC and (ii) variable and constant heavy chain sequences
(SEQ ID No. 2):
QVQLQQSGGELAKPGASVKVSCKASGYTFSSFWMHWVRQAPGQGLEWIGYI

NPRSGYTEYNEIFRDKATMTTDTSTSTAYMELSSLRSEDTAVYYCASFLGR

GAMDYWGQGTTVTVSSASTKGPSVFPLAPCSRSTSESTAALGCLVKDYFPE

PVTVSWNSGALTSGVHTFPAVLQSSGLYSLSSVVTVPSSNFGTQTYTCNVD

HKPSNTKVDKTVEPKSSDKTHTCPPCPAPPVAGPSVFLFPPKPKDTLMISR

TPEVTCVVVDVSHEDPEVQFNWYVDGVEVHNAKTKPREE**QAQSTFRVVSVL

TVVHQDWLNGKEYKCKVSNKGLPAPIEKTISKTKGQPREPQVYTLPPSREE

MTKNQVSLTCLVKGFYPSDIAVEWESNGQPENNYKTTPPMLDSDGSFFLYS

KLTVDKSRWQQGNVFSCSVMHEALHNHYTQKSLSLSPGK, wherein the underlined sequences represent the variable regions with the CDRs (in bold, identical with the parent mouse antibody). The modified IgG1 hinge region is represented by EPKSSDKTHTCPPCP (SEQ ID No. 3), and AQ is a substitution within the IgG2 domain.

However, as it was shown in WO 2009/010290, also variants of DI17E6 can be used according to the teaching of this invention. Thus, DI17E6 variants comprising one or more modifications within the heavy chain framework regions FR1:
(SEQ ID No. )
QVQLQQSGAELAEPGASVKMSCKASGYTFS FR2:
(SEQ ID No. 17)
WVKQRPGQGLEWIG FR3:
(SEQ ID No. )
KATMTADTSSSTAYMQLSGLTSEDSAVYYCAS FR4:
(SEQ ID No. 19)
WGQGTSVTVSS, wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

In general, the invention as described includes also modifications and variants of the DI17E6 antibody that are functionally and/or pharmaceutically identical or similar to unmodified DI17E6, and wherein the CDR regions and heavy and light chain variable regions are at least 80%, or at least 85%, or at least 90%, or at least 95% identical in their amino acid sequence compared to the respective variable regions of DI17E6. In addition, the invention also includes modifications and variants of the DI17E6 antibody that are functionally and/or pharmaceutically identical or similar to unmodified DI17E6, and wherein the constant regions are at least 80%, or at least 85%, or at least 90%, or at least 98% identical in their amino acid sequence compared to the respective constant regions of DI17E6. Changes is the constant regions of the IgG chains of the antibody may improve specific properties like immunogenicity, ADCC, and so on.

Thus, for use according the invention, also functional derivatives, biologically active variants or modifications of DI17E6 can be employed.

Accordingly, in the context of the present invention, the terms "Abituzumab" and/or "DI17E6" preferably also comprise:

a biologically active variant or modification thereof that comprises the CDR regions and heavy and light chain variable regions, which are 80%-95% identical in amino acid sequence compared to the variable regions of Abituzumab;

a biologically active variant or modification that comprises a constant region, which is at least 80%-98% identical with the amino acid sequence compared to the constant region of Abituzumab;

an antibody that comprises one or more modifications within the heavy chain framework regions FR1:
(SEQ ID No. 16)
QVQLQQSGAELAEPGASVKMSCKASGYTFS FR2:
(SEQ ID No. 17)
WVKQRPGQGLEWIG FR3:
(SEQ ID No. 18)
KATMTADTSSSTAYMQLSGLTSEDSAVYYCAS FR4:
(SEQ ID No. 19)
WGQGTSVTVSS, wherein one or more of the bold and underlined positions are mutated and are different compared to the original respective sequence of abituzumab;

and/or a modified DI17E6 antibody comprising a human IgG1 constant region instead of human IgG2, or a human IgG2 hinge region instead of the human IgG1 hinge.

Intetumumab or CNTO-95 is a human monoclonal antibody, preferably used in the treatment of solid tumors. It is also an anti-αv integrin antibody, which is preferably comprising human heavy chain and human light chain variable regions comprising the amino acid sequences as shown in SEQ ID NO: 7 and SEQ ID NO: 8, respectively, as shown below:

```
<210> SEQ ID NO 7
<211> LENGTH: 119
<212> TYPE: PRT
<213> ORGANISM: Homo sapiens

<400> SEQUENCE: 7

Gln Val Gln Leu Val Glu Ser Gly Gly Val Val
1               5                   10

Gln Pro Gly Arg Ser Arg Arg Leu Ser Cys Ala Ala
            15                  20

Ser Gly Phe Thr Phe Ser Arg Tyr Thr Met His Trp
25                  30                      35

Val Arg Gln Ala Pro Gly Lys Gly Leu Glu Trp Val
            40                  45
```

-continued

Ala Val Ile Ser Phe Asp Gly Ser Asn Lys Tyr Tyr
 50                  55                  60

Val Asp Ser Val Lys Gly Arg Phe Thr Ile Ser Arg
             65                  70

Asp Asn Ser Glu Asn Thr Leu Tyr Leu Gln Val Asn
         75                  80

Ile Leu Arg Ala Glu Asp Thr Ala Val Tyr Tyr Cys
 85              90                      95

Ala Arg Glu Ala Arg Gly Ser Tyr Ala Phe Asp Ile
             100                 105

Trp Gly Gln Gly Thr Met Val Thr Val Ser Ser
     110                 115

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser
 1               5                   10

Leu Ser Pro Gly Glu Arg Ala Thr Leu Ser Cys Arg
             15                  20

Ala Ser Gln Ser Val Ser Ser Tyr Leu Ala Trp Tyr
 25              30                      35

Gln Gln Lys Pro Gly Gln Ala Pro Arg Leu Leu Ile
             40                  45

Tyr Asp Ala Ser Asn Arg Ala Thr Gly Ile Pro Ala
 50              55                      60

Arg Phe Ser Gly Ser Gly Ser Gly Thr Asp Phe Thr
             65                  70

Leu Thr Ile Ser Ser Leu Glu Pro Glu Asp Phe Ala
         75                  80

Val Tyr Tyr Cys Gln Gln Arg Ser Asn Trp Pro Pro
 85              90                      95

Phe Thr Phe Gly Pro Gly Thr Lys Val Asp Ile Lys
             100                 105 and/or

LOCUS       ABN29020  119 aa linear      PAT Feb. 07, 2007

DEFINITION  Sequence 7 from patent US 7163681.

ACCESSION   ABN29020

VERSION     ABN29020.1  GI:125142205

DBSOURCE    accession ABN29020.1

KEYWORDS    .

SOURCE      Unknown.

ORGANISM    Unknown.
            Unclassified.

REFERENCE   1 (residues 1 to 119)

AUTHORS     Giles-Komar,J., Snyder,L., Trikha,M. and
            Nakada,M.T.

TITLE       Anti-integrin antibodies, compositions,
            methods and uses -continued

```
JOURNAL     Patent: US 7163681-A 7 Jan. 16, 2007;
            Centocor, Inc.; Malvern, PA;
            US;

REMARK      CAMBIA Patent Lens: US 7163681

FEATURES    Location/Qualifiers
            source 1..119
            /organism = "unknown"

ORIGIN
  1         qvqlvesggg vvqpgrsrrl scaasgftfs rytmhwvrqa pgkglewvav isfdgsnkyy
 61         vdsvkgrfti srdnsently lqvnilraed tavyycarea rgsyafdiwg qgtmvtvss
//

LOCUS       ABN29021 108 aa linear      PAT Feb. 07, 2007

DEFINITION  Sequence 8 from patent US 7163681.

ACCESSION   ABN29021

VERSION     ABN29021.1 GI:125142207

DBSOURCE    accession ABN29021.1

KEYWORDS    .

SOURCE      Unknown.

ORGANISM    Unknown.
            Unclassified.

REFERENCE   1 (residues 1 to 108)

AUTHORS     Giles-Komar,J., Snyder,L., Trikha,M. and
            Nakada,M.T.

TITLE       Anti-integrin antibodies, compositions,
            methods and uses JOURNAL     Patent: US 7163681-A 8 Jan. 16, 2007;
            Centocor, Inc.; Malvern, PA;
            US;

REMARK      CAMBIA Patent Lens: US 7163681

FEATURES    Location/Qualifiers source      1..108
            /organism = "unknown"

Region      2..107
            /region name = "IgV_L_kappa"
            /note = "Immunoglobulin (Ig) light
            chain, kappa type,
            variable (V) domain; cd04980"
            /db_xref = "CDD:143181"

Region      8..100
            /region name = "IG_like"
            /note = "Immunoglobulin like;
            smart00410"
            /db_xref = "CDD:214653"

Site        order(12,104,106..107)
            /site_type = "other"
            /note = "intrachain domain
            interface"
            /db_xref = "CDD:143181"

Site        25..27
            /site_type = "other"
            /note = "L1 hypervariable region"
            /db_xref = "CDD:143181"
```

```
                          -continued
Site        order(32,49,93)
            /site_type = "other"
            /note = "antigen binding site"
            /db_xref = "CDD:143181"

Site        order(34,36,38,43,46,50,87)
            /site type = "other"
            /note = "heterodimer interface
            [polypeptide binding]"
            /db_xref = "CDD:143181"

Site        66..70
            /site_type = "other"
            /note = "L2 hypervariable region"
            /db_xref = "CDD:143181"

Site        order(92..94,96..98)
            /site_type = "other"
            /note = "L3 hypervariable region"
            /db_xref = "CDD:143181"

ORIGIN
  1         eivltqspat lslspgerat lscrasgsys sylawyqqkp gqaprlliyd asnratgipa
 61         rfsgsgsgtd ftltisslep edfavyycqq rsnwppftfg pgtkvdik
//
```

Intetumumab is further characterised in WO02/12501 and U.S. Pat. No. 7,163,681, the disclosure of which is incorporated in their entirety into this application by reference.

Preferably, also functional derivatives, biologically active variants or modifications of Intetumumab can be employed in the instant invention.

For ease of use, the one or more proteins that are preferably active as biomarkers in the context of the present invention, i.e.

DCN (Somamer ID: SL004081; UniProt ID: P07585),
F5 (Somamer ID: SL000622; UniProt ID: P12259),
ICAM3 (Somamer ID: SL003178; UniProt ID: P32942),
PIGR (Somamer ID: SL005797; UniProt ID: P01833),
STK17B (Somamer ID: SL016566; UniProt ID: O94768),
STX1A (Somamer ID: SL004304; UniProt ID: Q16623), and
TEK (Somamer ID: SL003200; UniProt ID: Q02763), and/or b) one or more proteins, selected from the group consisting of ANG (Somamer ID: SL000003; UniProt ID: P03950),
ID B (Somamer ID: SL001795; UniProt ID: P01584),
LEPR (Somamer ID: SL003184; UniProt ID: P48357),
MAP2K2 (Somamer ID: SL010501; UniProt ID: P36507),
MAPK11 (Somamer ID: SL007453; UniProt ID: Q15759),
RGMB (Somamer ID: SL010468; UniProt ID: Q6NW40), and
TNFRSF17 (Somamer ID: SL004672; UniProt ID: Q02223), are preferably also referred to collectively as "specific proteins" or "said specific proteins" of the present invention, and preferably also referred to individuality as "the specific protein" or "said specific protein".

As used herein, the term "sequence homology" is understood by the ones skilled in the art, and methods for determining sequence homology are also known in the art.

As used herein, sequence homology is preferably determined using the BLAST algorithm. BLAST preferably stands for for Basic Local Alignment Search Tool and is an algorithm for comparing primary biological sequence information, such as the amino-acid sequences of different proteins or the nucleotides of DNA sequences. A BLAST search enables a researcher to compare a query sequence with a library or database of sequences, and identify library sequences that resemble the query sequence above a certain threshold. The BLAST algorithm and the computer program that implements it were developed by Stephen Altschul, Warren Gish, and David Lipman at the U.S. National Center for Biotechnology Information (NCBI), Webb Miller at the Pennsylvania State University, and Gene Myers at the University of Arizona. It is available on the web on the NCBI website. Alternative implementations include AB-BLAST (formerly known as WU-BLAST), FSA-BLAST (last updated in 2006), and ScalaBLAST.

Different types of BLASTs are available according to the query sequences. For example, following the discovery of a previously unknown gene in the mouse, a scientist will typically perform a BLAST search of the human genome to see if humans carry a similar gene; BLAST will identify sequences in the human genome that resemble the mouse gene based on similarity of sequence. The BLAST algorithm and program were designed by Stephen Altschul, Warren Gish, Webb Miller, Eugene Myers, and David J. Lipman at the NIH and was published in the Journal of Molecular Biology in 1990.

In the context of the present invention, the sequence homology of the proteins described herein is preferably determined on the basis of the longest local alignments generated using BLASTp.

In the context of the present invention, subjects and especially human subjects are preferably also referred to as patients.

As used herein, the term "about" with respect to numbers, amounts, dosings, hours, times, timings, durations, and the like, is preferably understood to mean "approximately" with respect to said numbers, amounts, dosings, hours, times, timings, durations, and the like. More Preferably, the term "about" means +/−10%, more preferably +/−5% of the given specific value with respect to numbers, amounts, dosings, hours, times, timings, durations, and the like.

If not specified otherwise, amounts administered to a subject, human subject or patient given in "mg", such as in 500 mg, 1000 mg, or the like, are preferably intended to mean the respective amounts to be administered "flat", i.e.

as a fixed dose that is not adjusted to the bodyweight and/or body surface of the respective subject, human subject or patient.

If not explicitly indicated otherweise, the term "one or more" as used herein, e.g. with respect to the number of compounds, agents, cancer cotherapeutic agents, cancer chemotherapeutic agents and the like, preferably means "one or more than one" and thus preferably includes "two or more" (or "two or more than two"), "three or more" (or "three or more than three") and/or "four more" (or "more or more than four"). Accordingly, the term "one or more" as used herein preferably includes the numbers one, two, three, four, five, six and/or higher numbers. With respect to the number of agents, cancer cotherapeutic agents, cancer chemotherapeutic agents, it especially preferably includes the numbers one, two, three, four and/or five, even more preferably the numbers one, two, three and/or four and especially the numbers one, two and/or three.

Preferably, especially preferred subjects of the instant invention relate to aspects, subjects, uses, methods and/or embodiments, wherein one or more features of two or more of the herein described aspects, subjects, uses, methods and/or embodiments are combined in one subject.

The invention is explained in greater detail below by means of examples. The invention can be carried out throughout the range claimed and is not restricted to the examples given here.

The following examples are given in order to assist the skilled artisan to better understand the present invention by way of exemplification. The examples are not intended to limit the scope of protection conferred by the claims. The features, properties and advantages exemplified for the compounds and uses defined in the examples may be assigned to other compounds and uses not specifically described and/or defined in the examples, but falling under the scope of what is defined in the claims.

EXPERIMENTAL SECTION

Example 1

PERSEUS Phase II Clinical Study
  c) Leuproreline, Leuproreline acetate and/or pharmaceutically acceptable derivatives and/or salts thereof,
  in combination with
  Zoledronic acid and/or pharmaceutically acceptable derivatives and/or salts thereof
    PERSEUS Phase II clinical trial
    In this randomized, double-blind, placebo-controlled, international phase II trial, a total of 180 patients were randomized 1:1:1 to receive
      a) Standard of Care (SoC), e.g. continuous treatment with a luteinizing hormone-releasing hormone agonist, preferably Leuproreline, Leuproreline acetate and/or pharmaceutically acceptable derivatives and/or salts thereof, and bisphosphonate treatment, preferably Zoledronic acid and/or pharmaceutically acceptable derivatives and/or salts thereof, plus placebo,
      b) abituzumab 750 mg plus SoC, or
      c) abituzumab 1,500 mg plus SoC.
Pharmacokinetic Analysis
    Equal numbers of patients per arm were included in the pharmacokinetic analysis subgroup.
    Blood sampling for pharmacokinetic assessments was scheduled at various timepoints during cycles 1, 3, 4, 5, 6, and 7 of therapy.
    Pharmacokinetic parameters were calculated according to standard non-compartmental methods using the program KINETICATM v4.1.1 (Innaphase).
Immunogenicity
    Blood sampling for immunogenicity was scheduled pre-dose in cycles 1, 3, 5 and 6, and at the end-of-treatment visit and safety follow-up visits.
    Generation of antibodies directed against abituzumab was evaluated centrally using a validated ELISA method.
Biomarker Analyses
    Archived tumor blocks or punch biopsy materials were collected to explore tumor expression of integrins and their ligands as well as proteins related to angiogenesis and the underlying disease, and their potential relationship to clinical outcomes.
        Availability of samples had to be confirmed at patient screening
        Analyses were performed using immunohistochemistry.
    Blood sampling for plasma protein analyses was scheduled pre-treatment.
    Plasma protein analyses (based on highly protein-specific aptamers [SomaLogic system]) were performed on samples taken from 150 patients prior to treatment in cycle 1
        The original set of simultaneously determined 1,129 plasma protein levels was restricted to 888 proteins on the data level to avoid potential bias due to cell lysis or platelet activation during plasma preparation
        Nine global biomarker search analyses were carried out using different normalization procedure, data sets and biomarker dichotomization thresholds, with the aim of filtering biomarker proteins based on data robustness independent of biological annotations. The search process comprised a set of criteria ensuring that identified proteins are significantly ($p<0.05$) associated with outcome (here exemplary radiologic PFS) for either the patients with low or high levels. These tests comprise, among others, logrank tests for differences in survival (here PFS) for Abituzumab-treated/untreated patients in the biomarker-low and biomarker-high groups according to the median threshold, tests for an interaction effect on outcome (here PFS) between continuous marker levels and treatment based on Cox regression models.
        This process identified 15 biomarker plasma proteins:
        DCN (Somamer ID: SL004081; UniProt ID: P07585),
    F5 (Somamer ID: SL000622; UniProt ID: P12259),
    ICAM3 (Somamer ID: SL003178; UniProt ID: P32942),
    PIGR (Somamer ID: SL005797; UniProt ID: P01833),
    STK17B (Somamer ID: SL016566; UniProt ID: O94768),
    STX1A (Somamer ID: SL004304; UniProt ID: Q16623),
    TEK (Somamer ID: SL003200; UniProt ID: Q02763),
    ANG (Somamer ID: SL000003; UniProt ID: P03950),
    IL1B (Somamer ID: SL001795; UniProt ID: P01584),
    LEPR (Somamer ID: SL003184; UniProt ID: P48357),
    MAP2K2 (Somamer ID: SL010501; UniProt ID: P36507),
    MAPK11 (Somamer ID: SL007453; UniProt ID: Q15759),
    RGMB (Somamer ID: SL010468; UniProt ID: Q6NW40), and
    TNFRSF17 (Somamer ID: SL004672; UniProt ID: Q02223)

Results
Biomarker Analyses
IHC analysis of tumor samples has not identified any relevant biomarkers to date.

Figure 2:
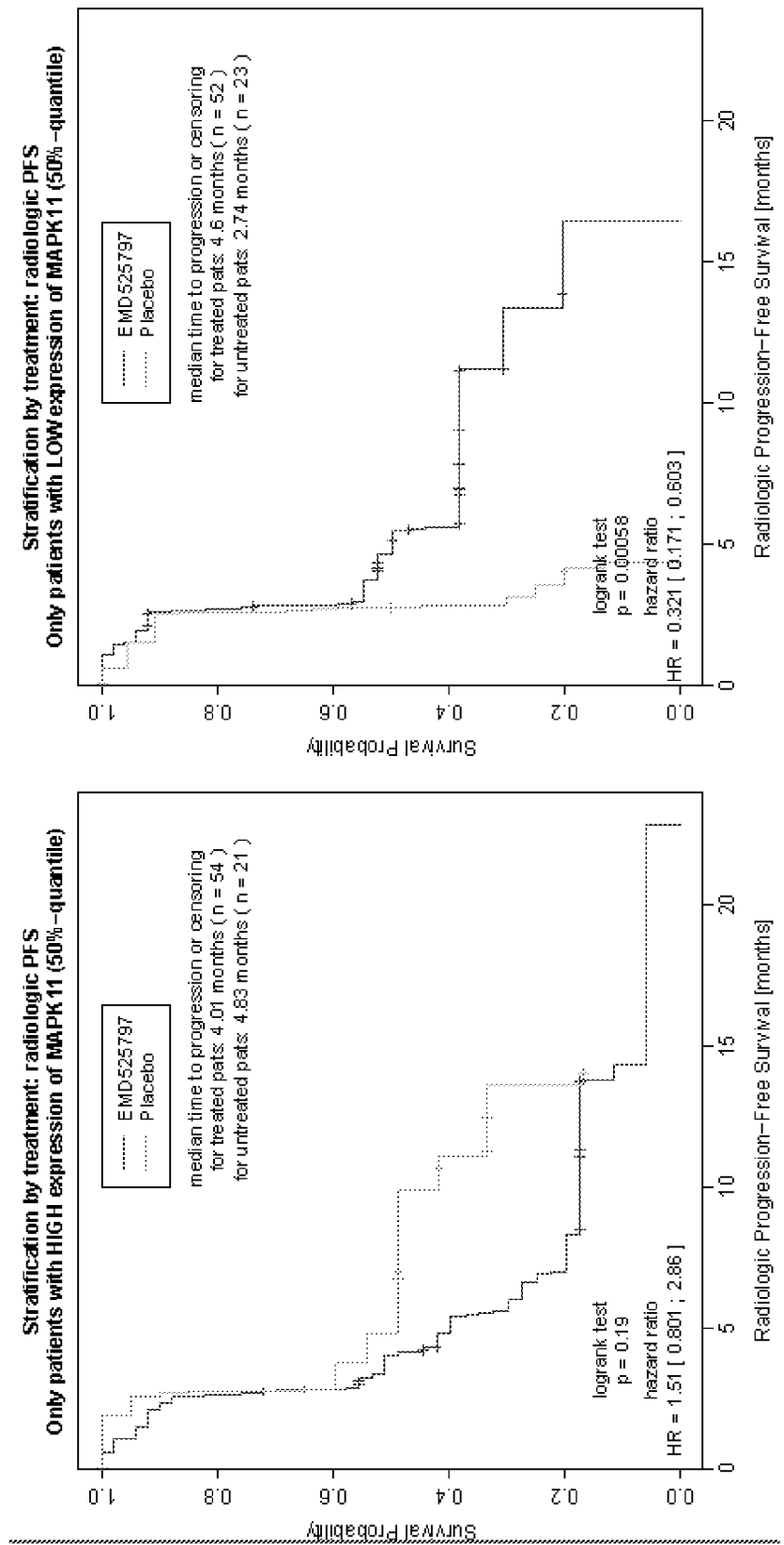
FIG. 2 displays rPFS of EMD 525797-treated patients and placebo-treated patients for high and low expressions of MAPK11.
Figure 3:
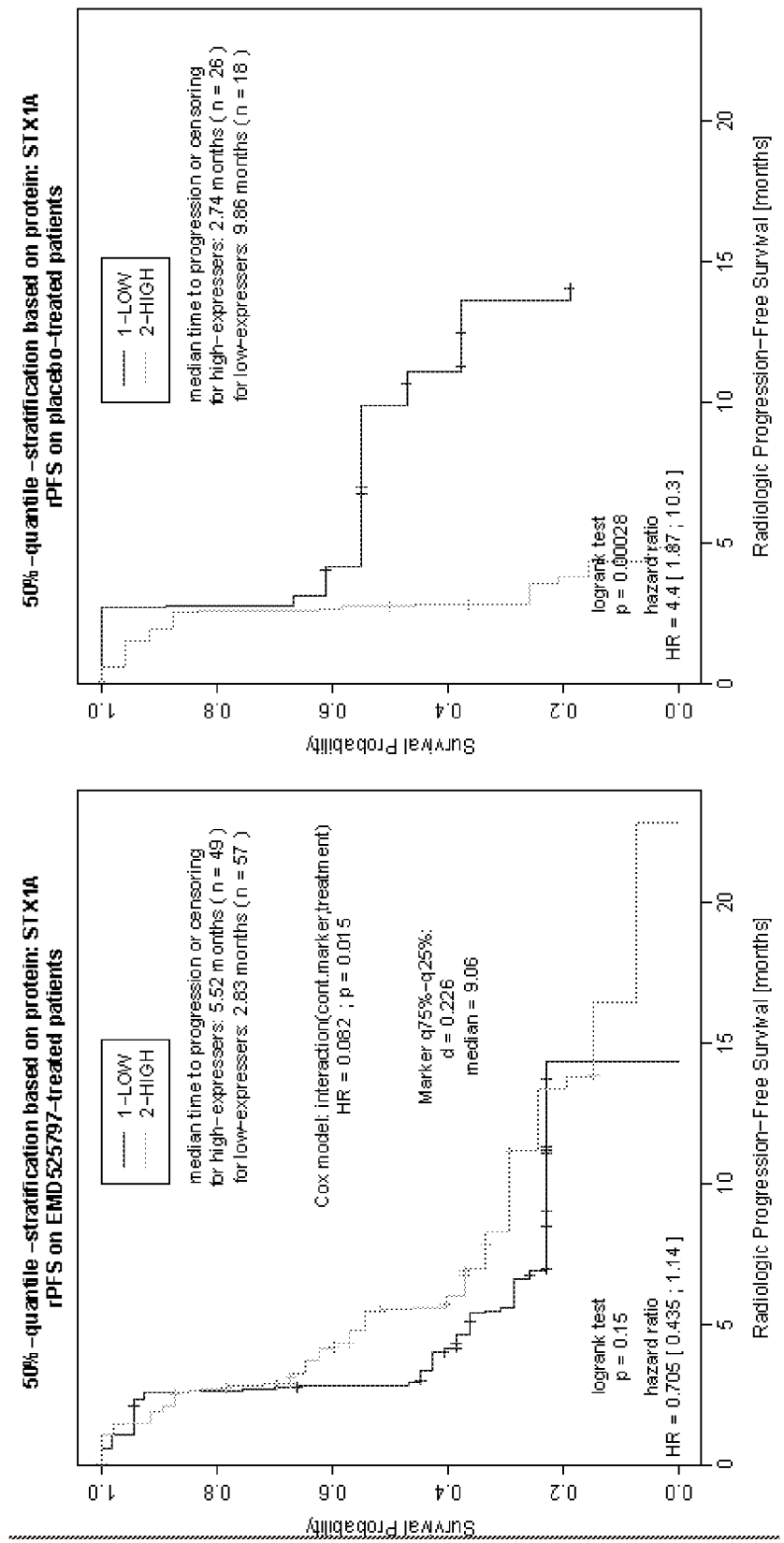
FIG. 3 displays rPFS of patients with high and low expressions of STX1A for EMD 525797-treated patients and placebo-treated patients.
Figure 4:
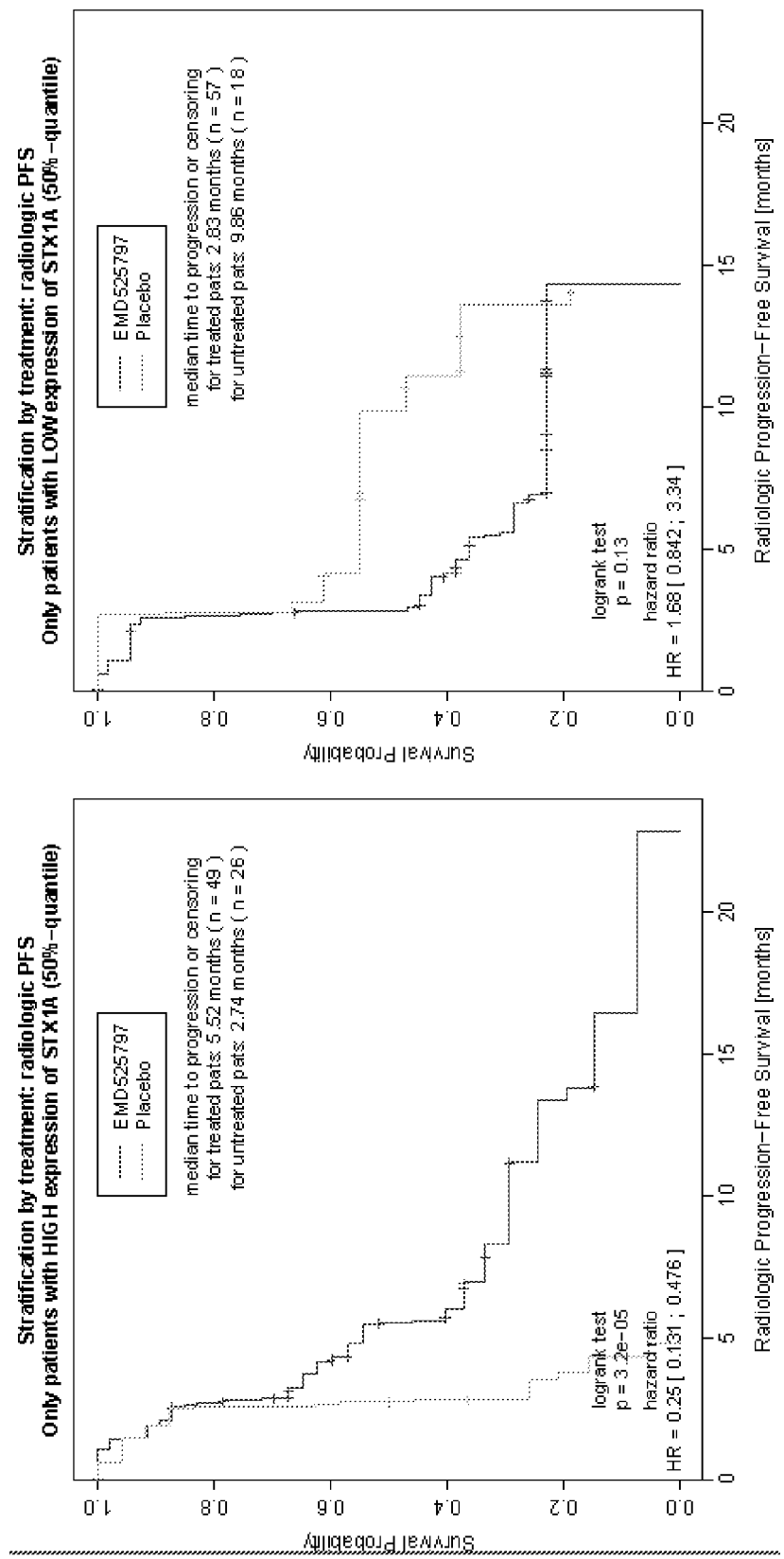
FIG. 4 displays rPFS of EMD 525797-treated patients and placebo-treated patients for high and low expressions of STX1A.
Figure 5:
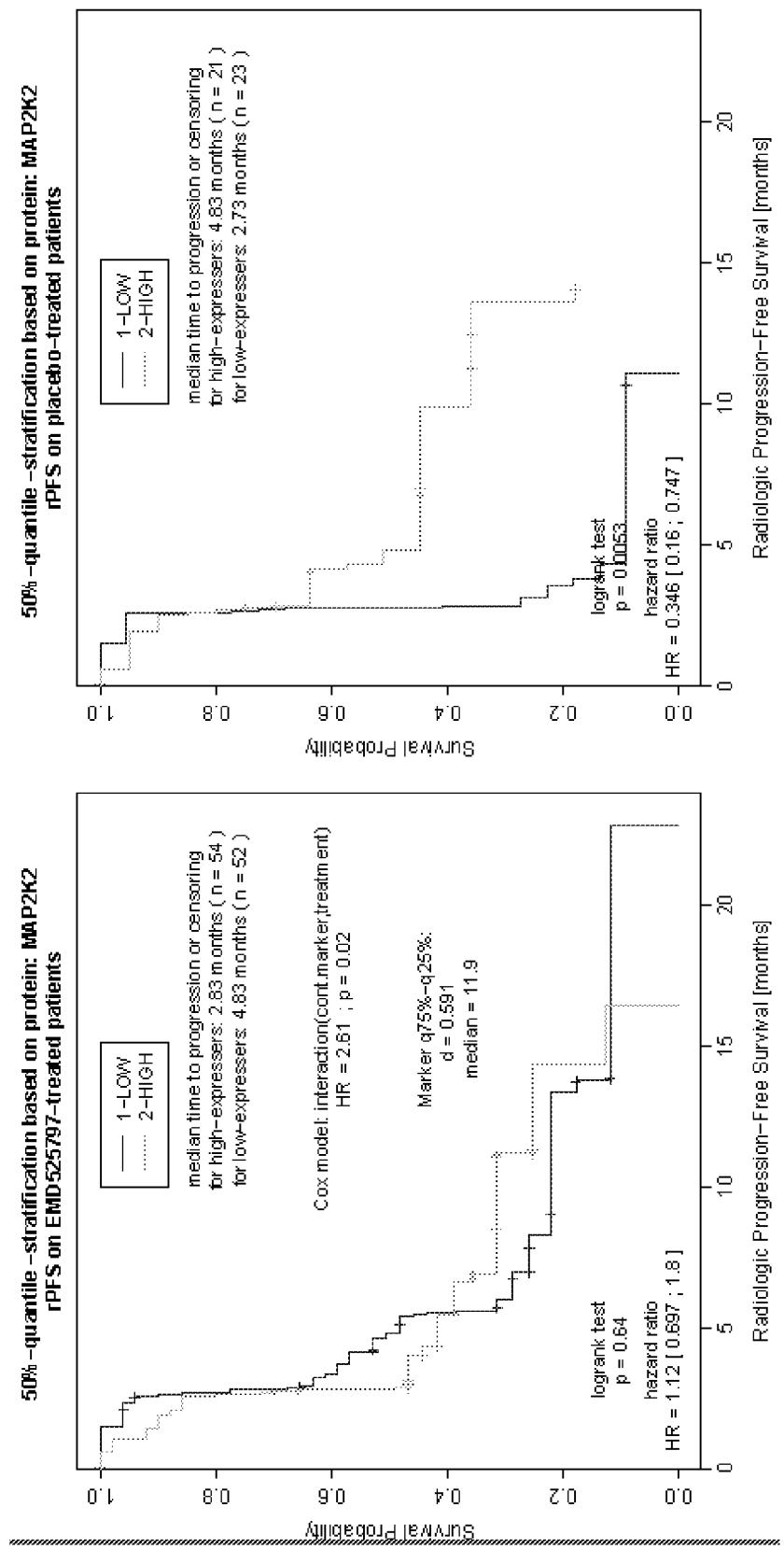
FIG. 5 displays rPFS of patients with high and low expressions of MAP2K2 for EMD 525797-treated patients and placebo-treated patients.
Figure 6:
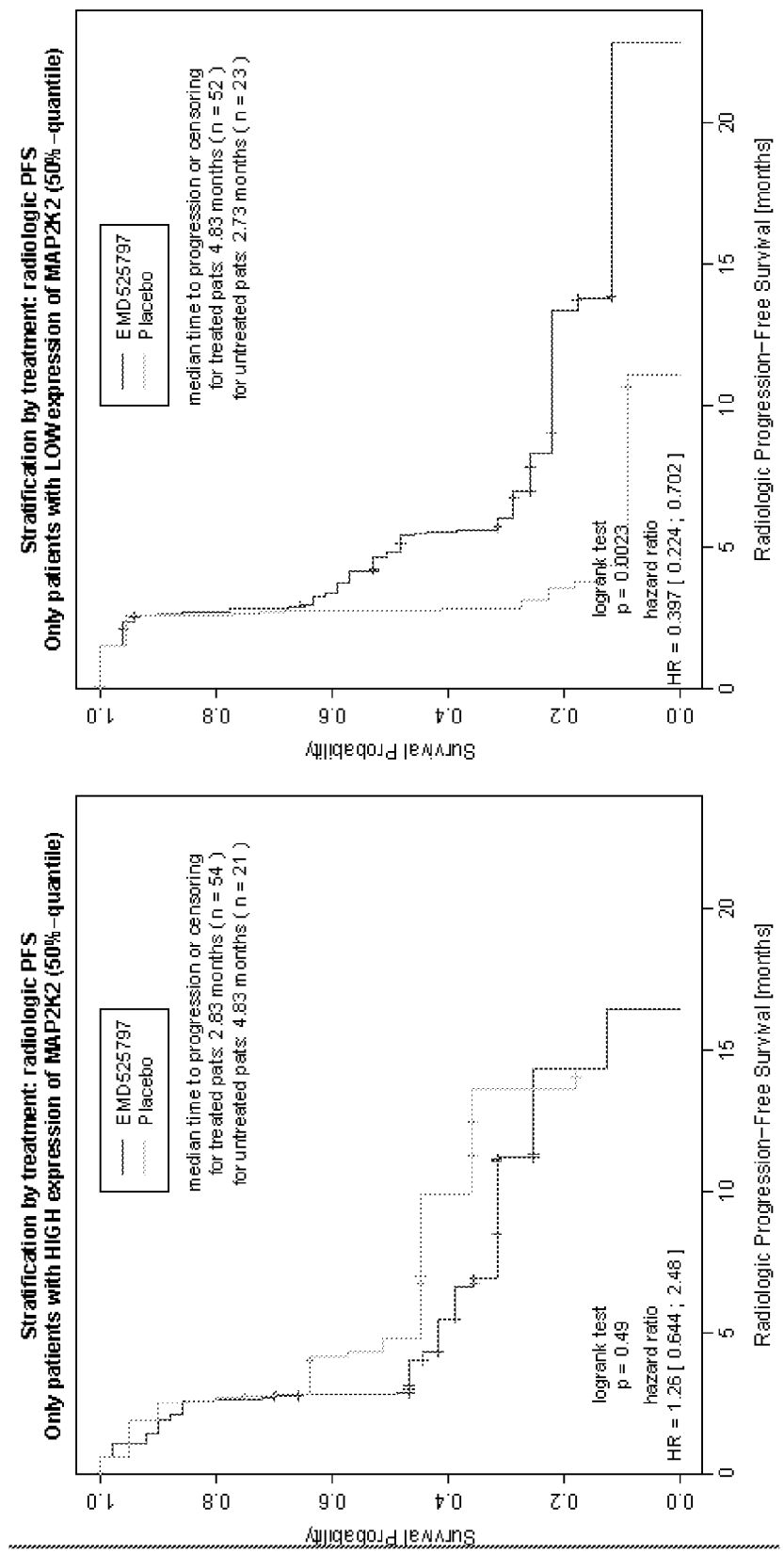
FIG. 6 displays rPFS of EMD 525797-treated patients and placebo-treated patients for high and low expressions of MAPK2K2.
Figure 7:
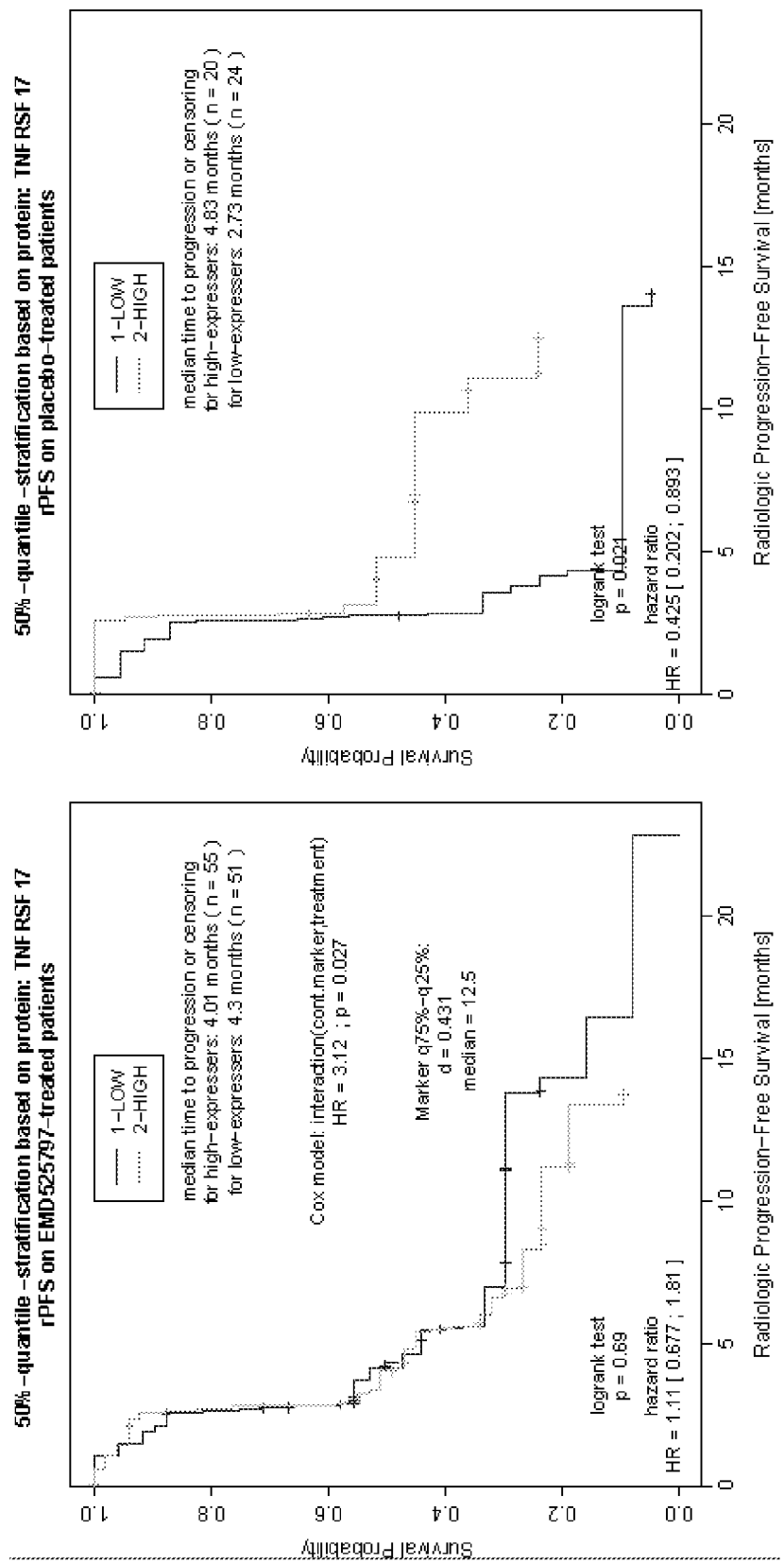
FIG. 7 displays rPFS of patients with high and low expressions of TNFRSF17 for EMD 525797-treated patients and placebo-treated patients.
Figure 8:
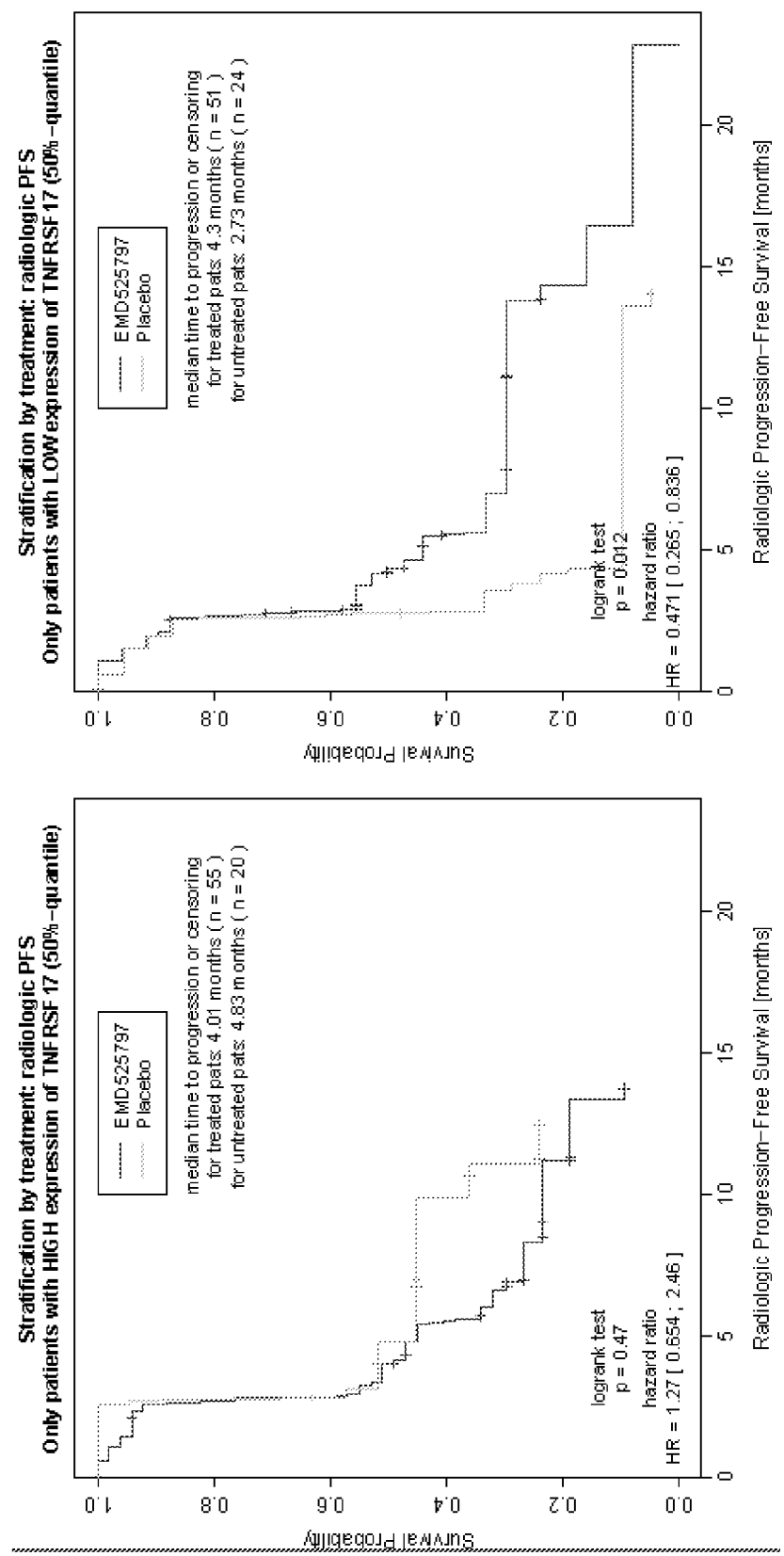
FIG. 8 displays rPFS of EMD 525797-treated patients and placebo-treated patients for high and low expressions of TNFRSF17.
Figure 9:
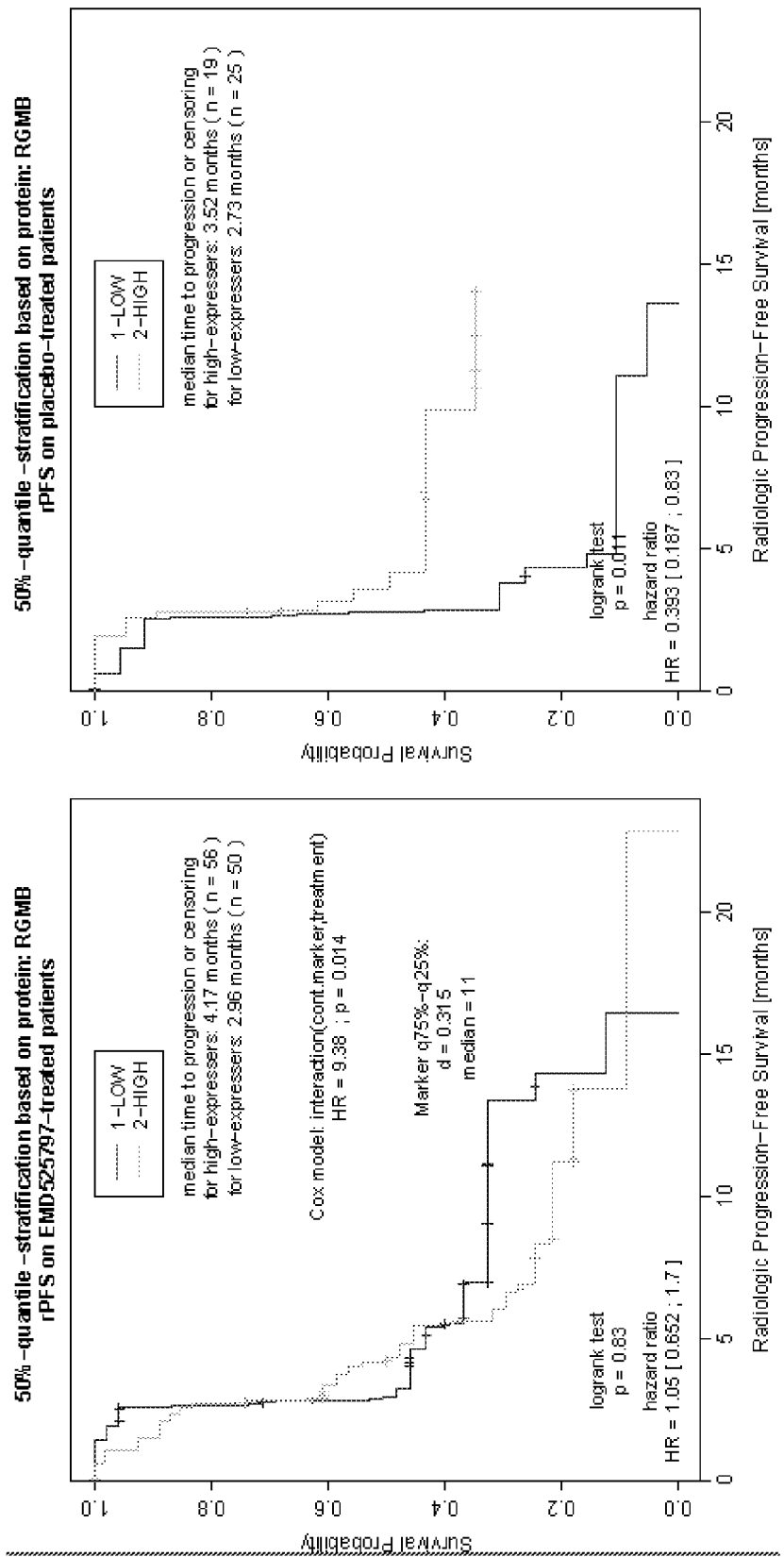
FIG. 9 displays rPFS of patients with high and low expressions of RGMB for EMD 525797-treated patients and placebo-treated patients.
Figure 10:
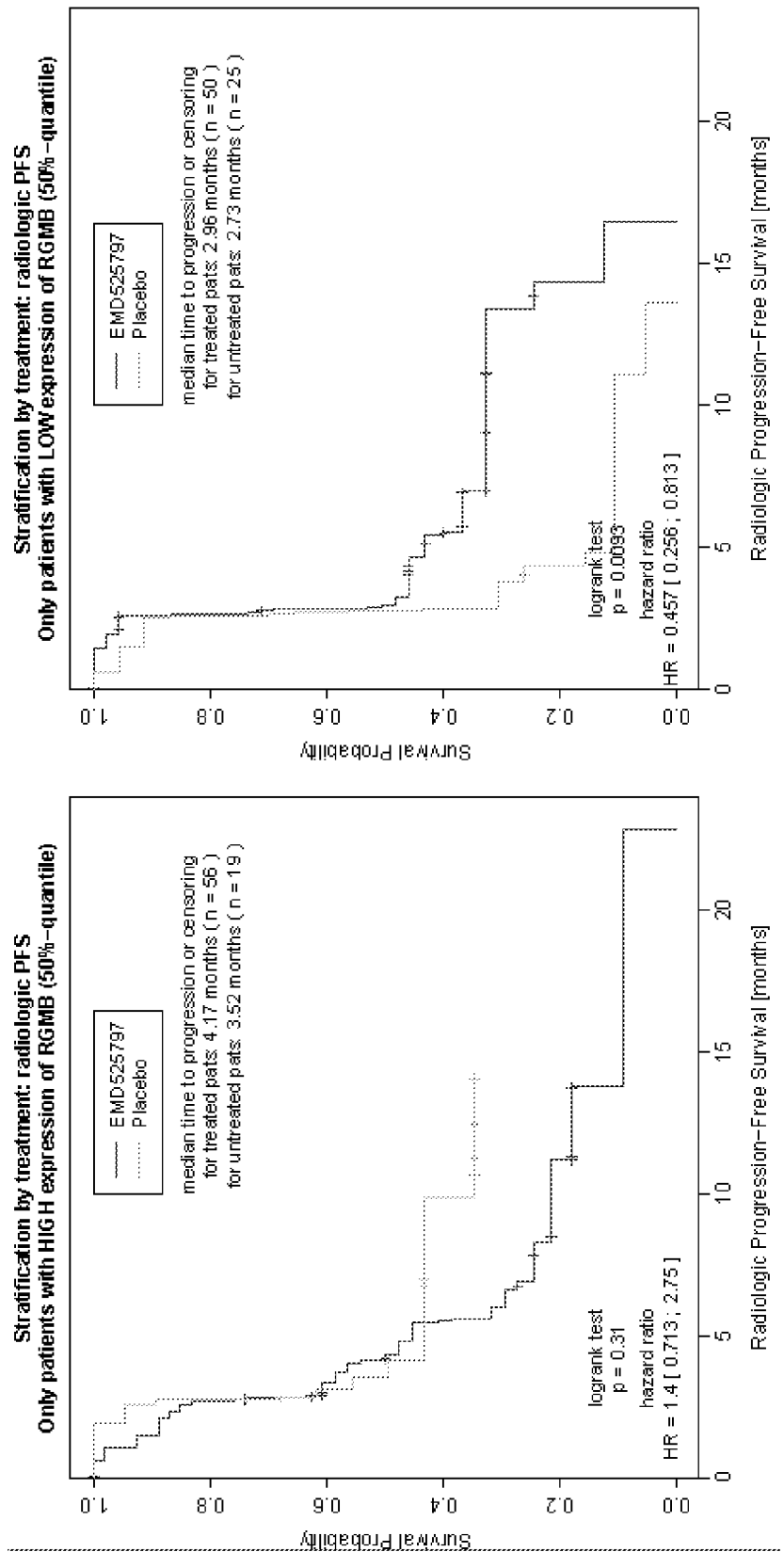
FIG. 10 displays rPFS of EMD 525797-treated patients and placebo-treated patients for high and low expressions of RGMB.
Figure 11:
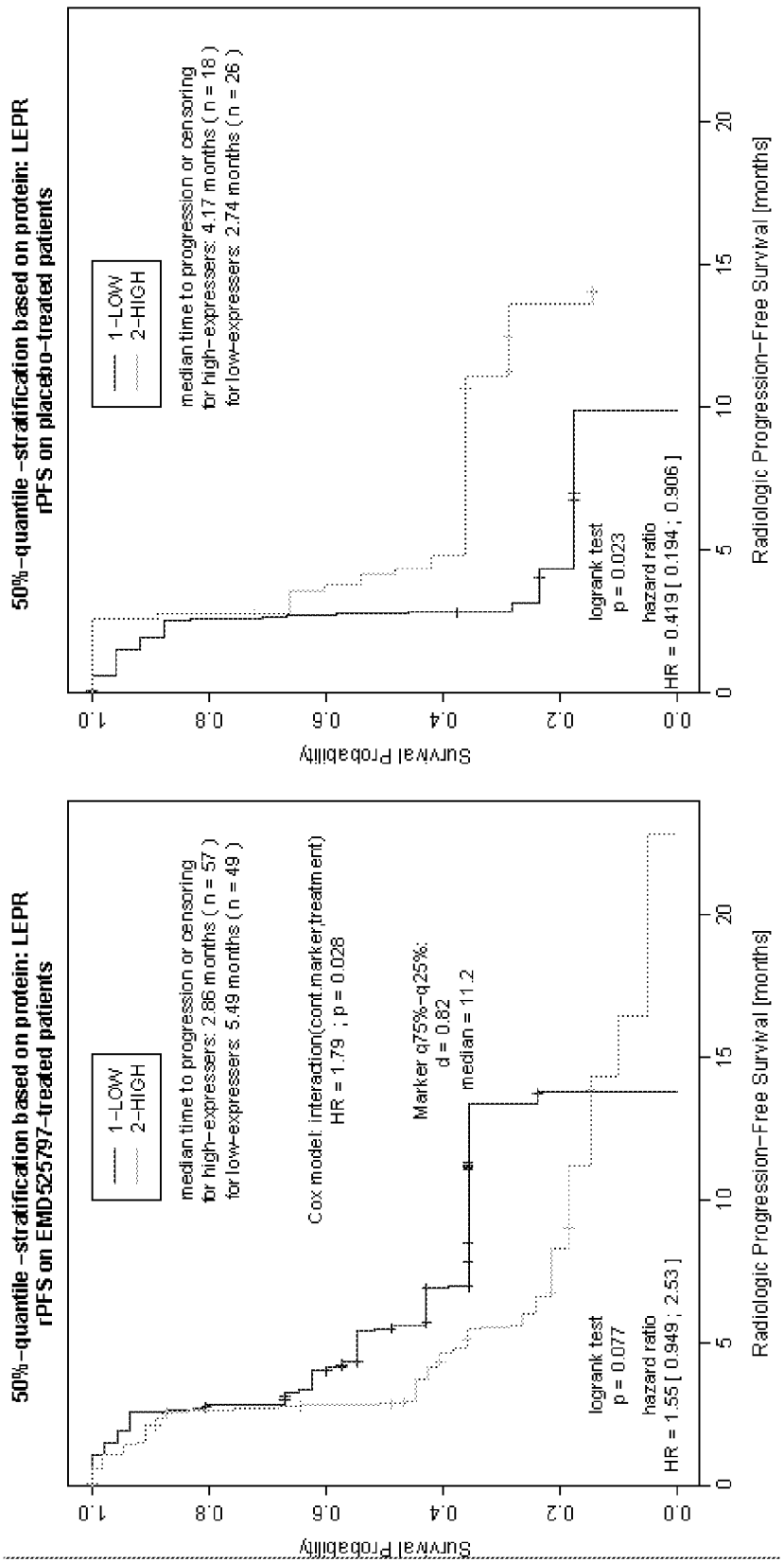
FIG. 11 displays rPFS of patients with high and low expressions of LEPR for EMD 525797-treated patients and placebo-treated patients.
Figure 12:
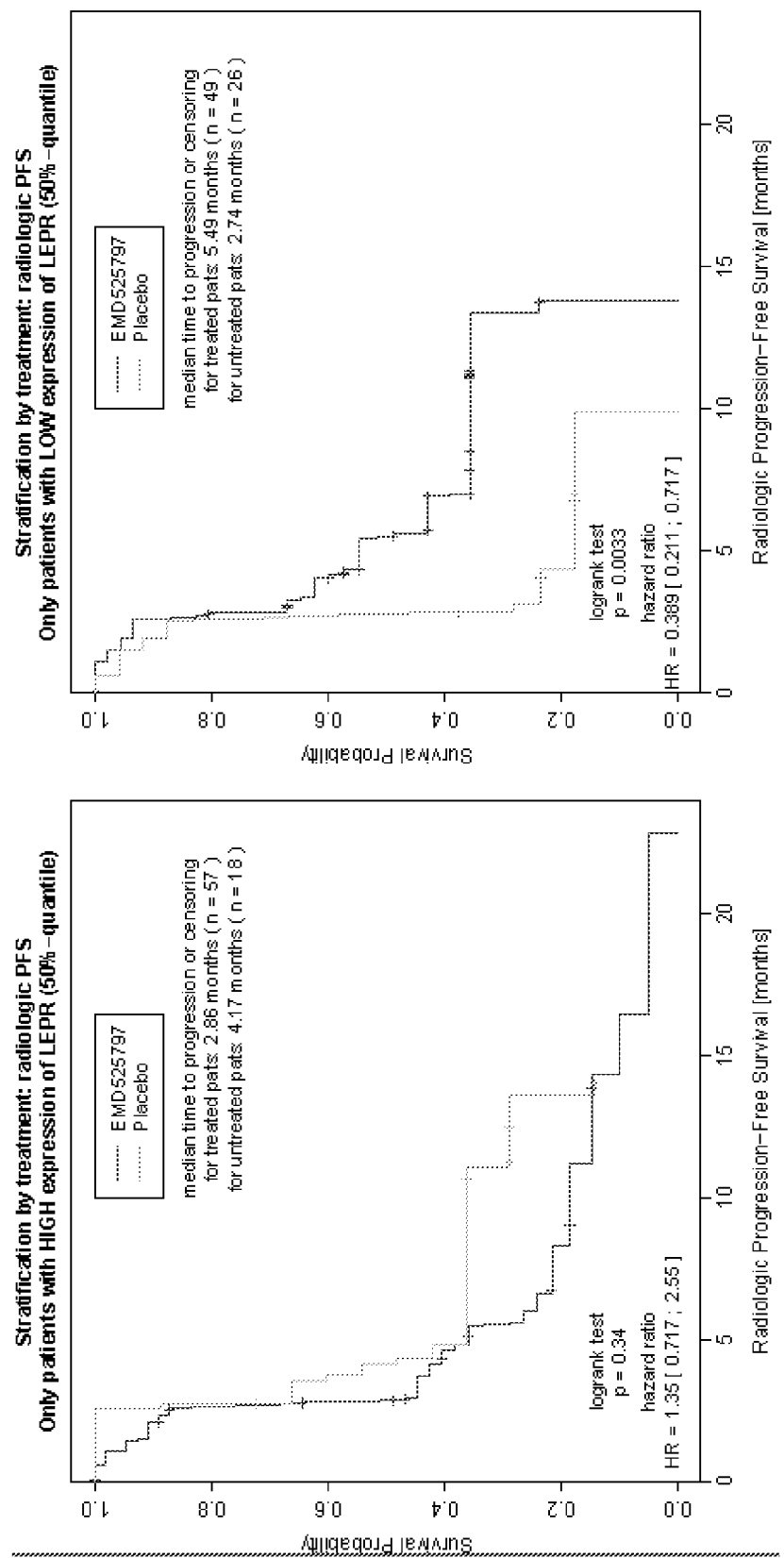
FIG. 12 displays rPFS of EMD 525797-treated patients and placebo-treated patients for high and low expressions of LEPR.
Figure 13:
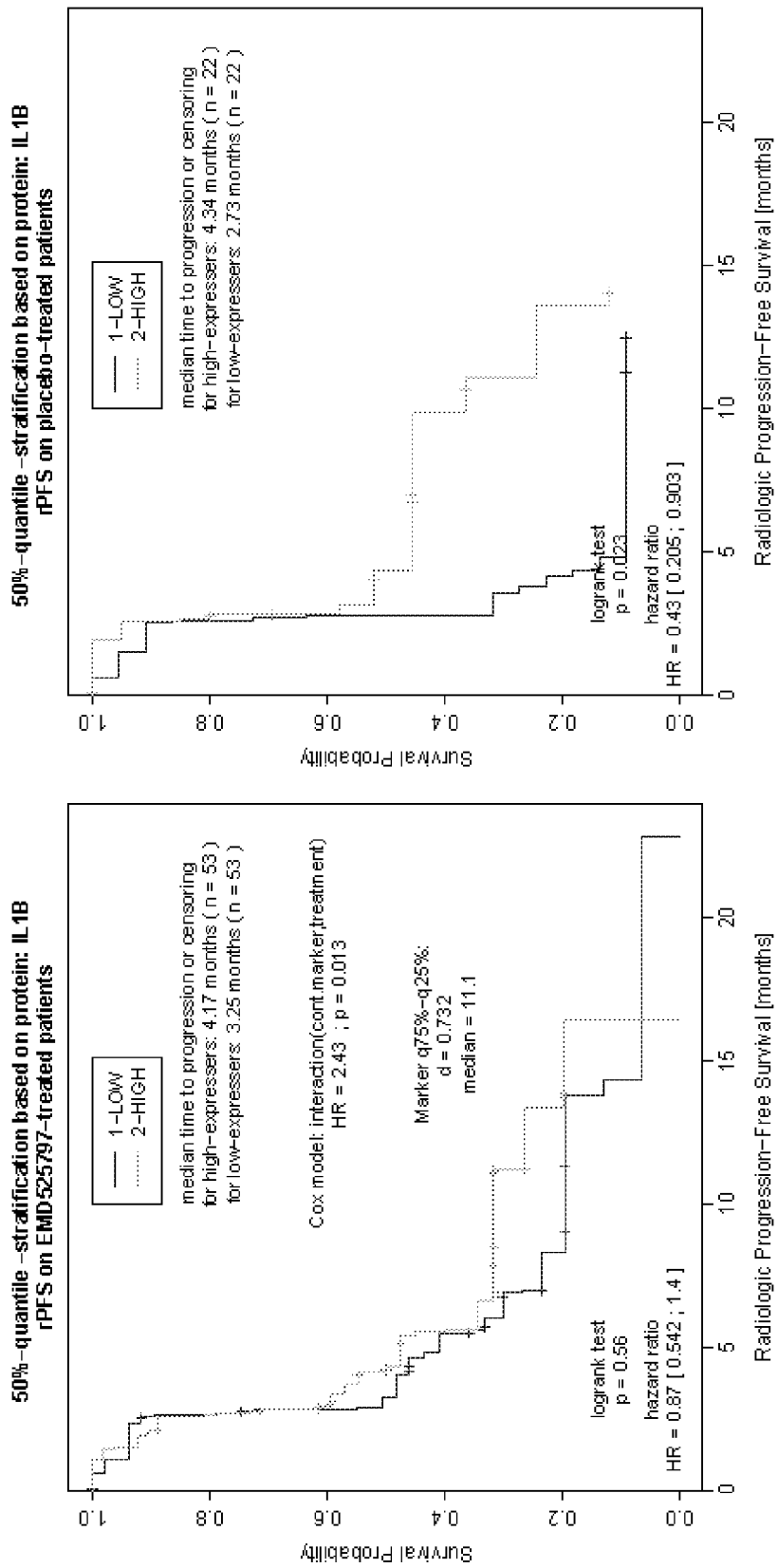
FIG. 13 displays rPFS of patients with high and low expressions of IL1B for EMD 525797-treated patients and placebo-treated patients.
Figure 14:
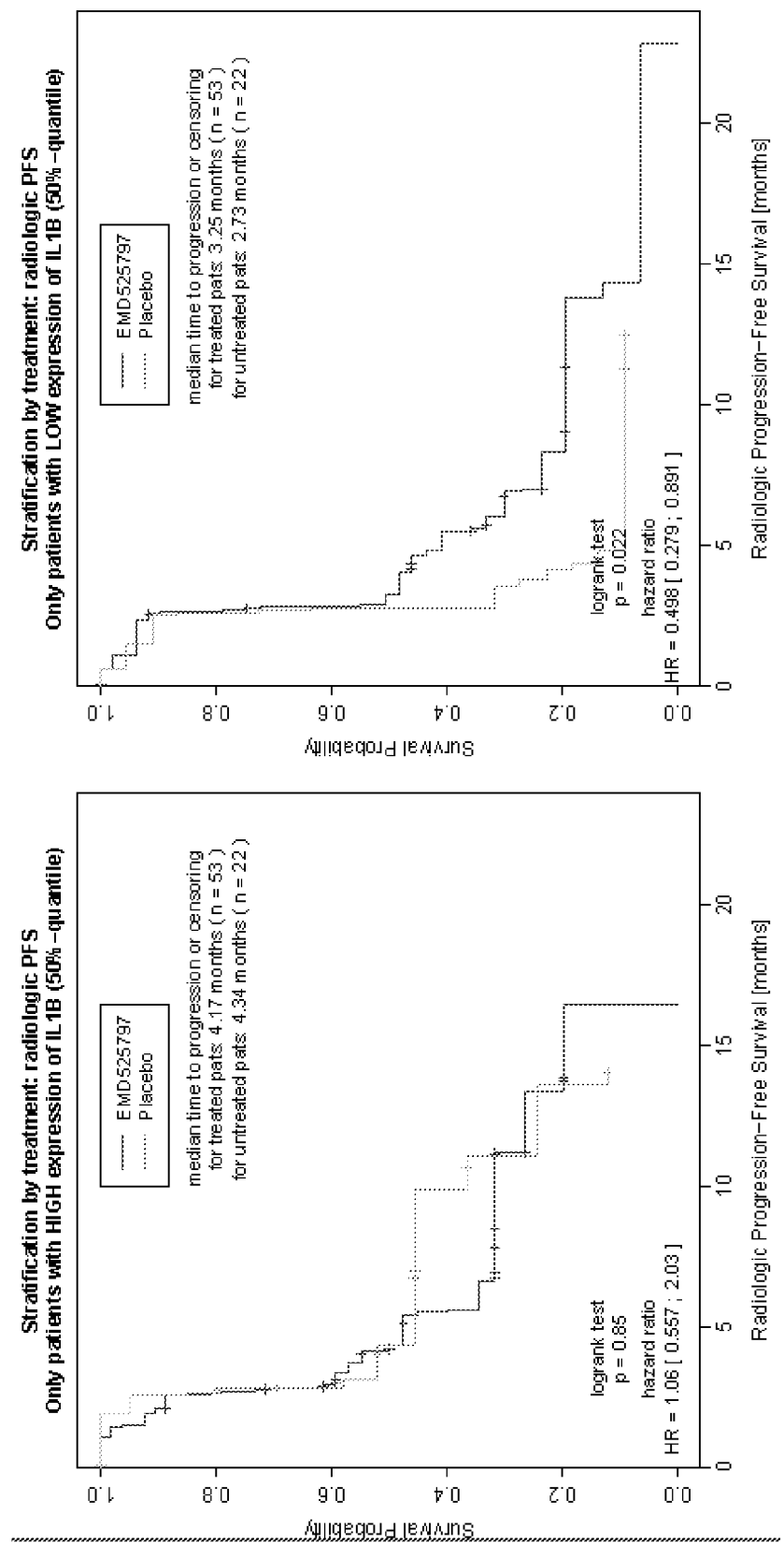
FIG. 14 displays rPFS of EMD 525797-treated patients and placebo-treated patients for high and low expressions of IL1B.
Figure 15:
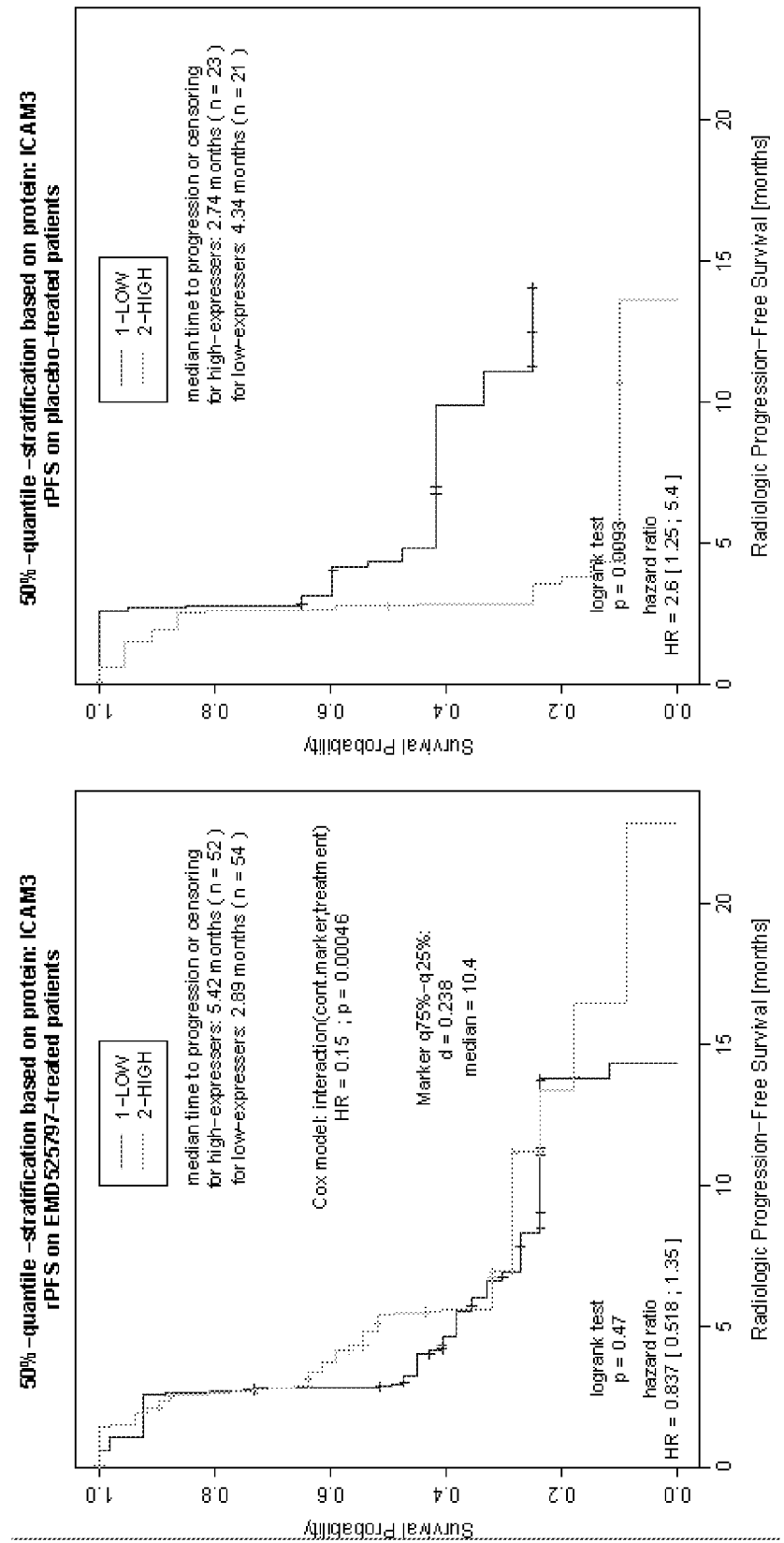
FIG. 15 displays rPFS of patients with high and low expressions of ICAM3 for EMD 525797-treated patients and placebo-treated patients.
Figure 16:
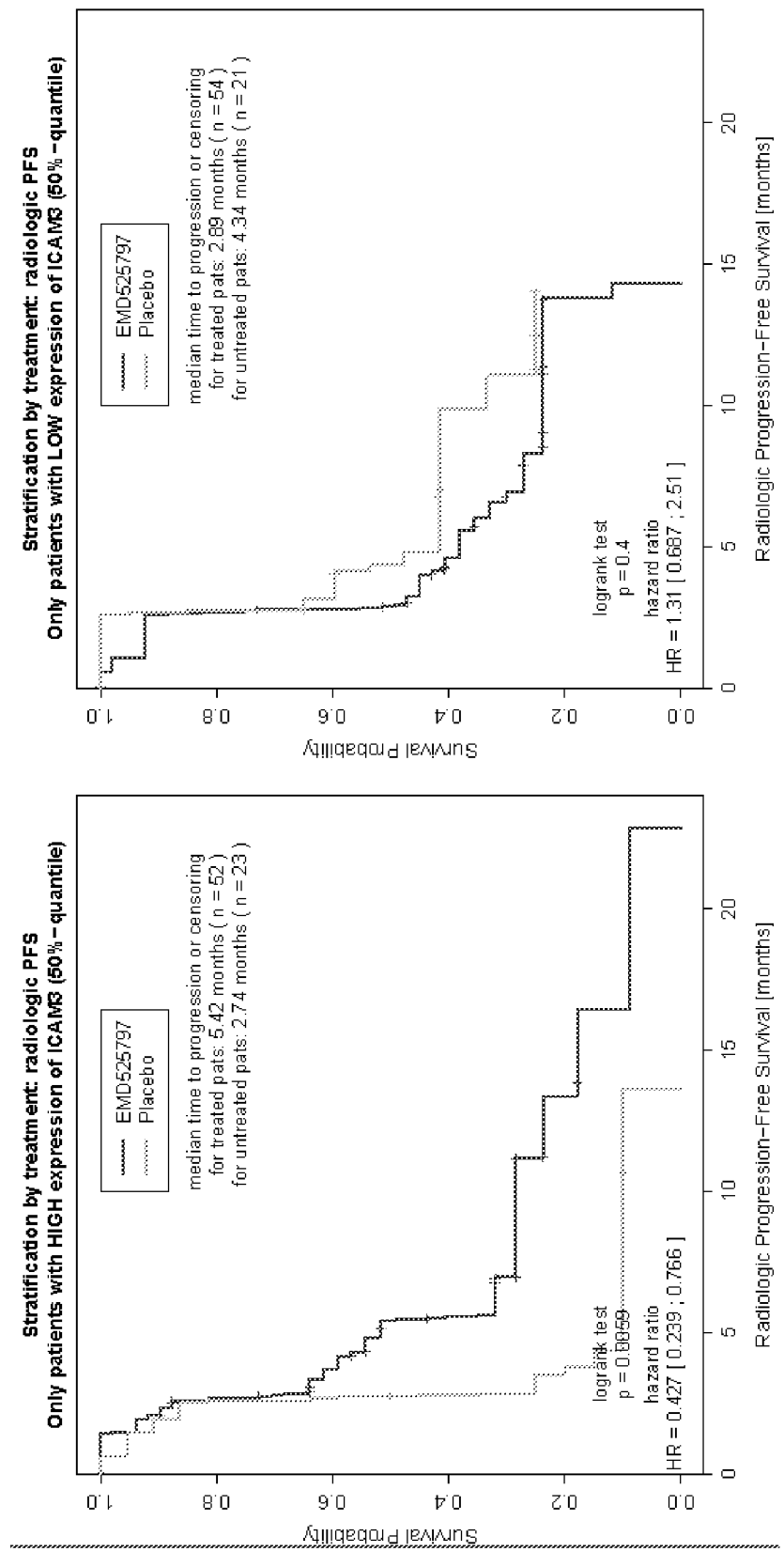
FIG. 16 displays rPFS of EMD 525797-treated patients and placebo-treated patients for high and low expressions of ICAM3.
Figure 17:
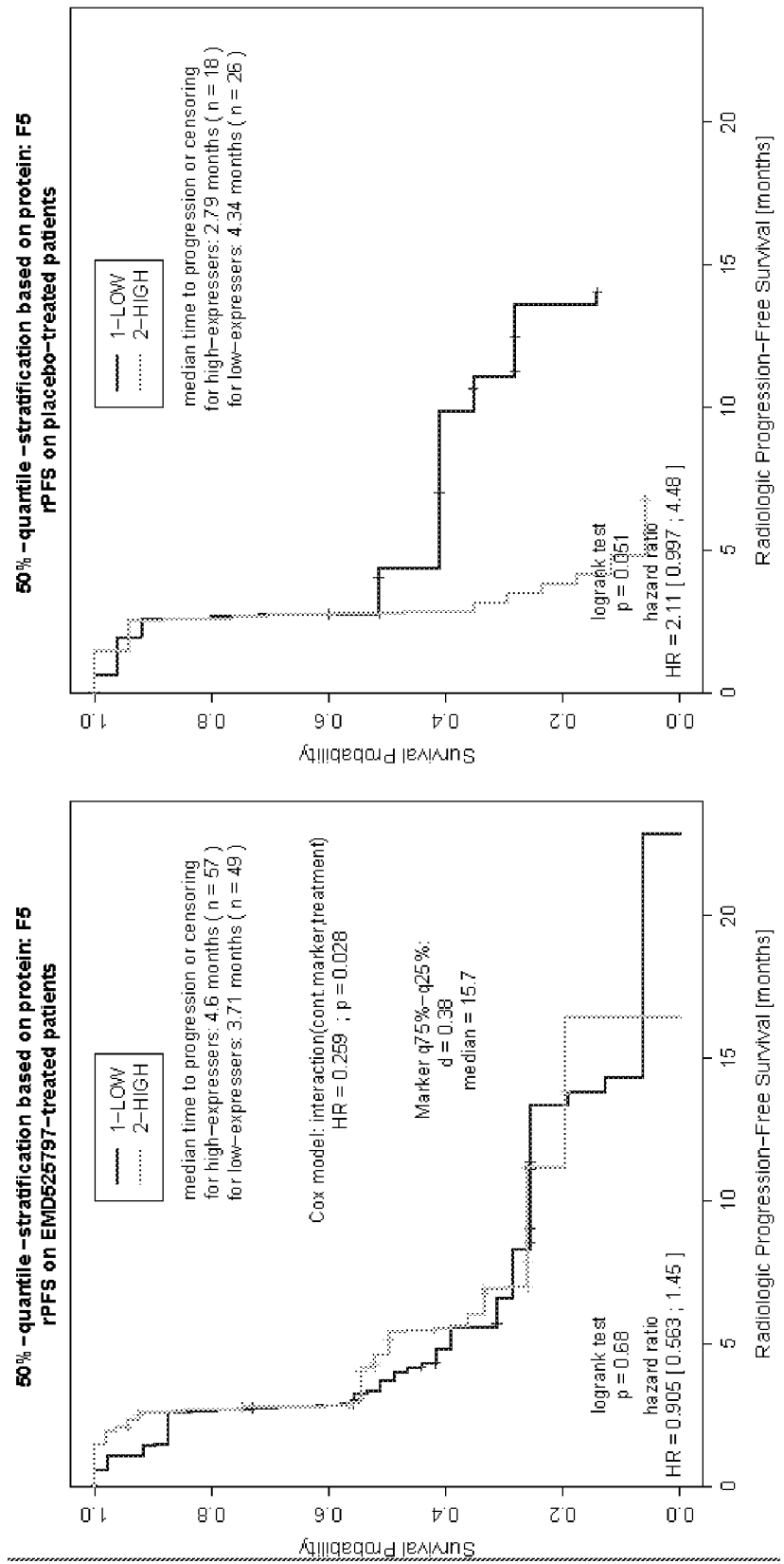
FIG. 17 displays rPFS of patients with high and low expressions of F5 for EMD 525797-treated patients and placebo-treated patients.
Figure 18:
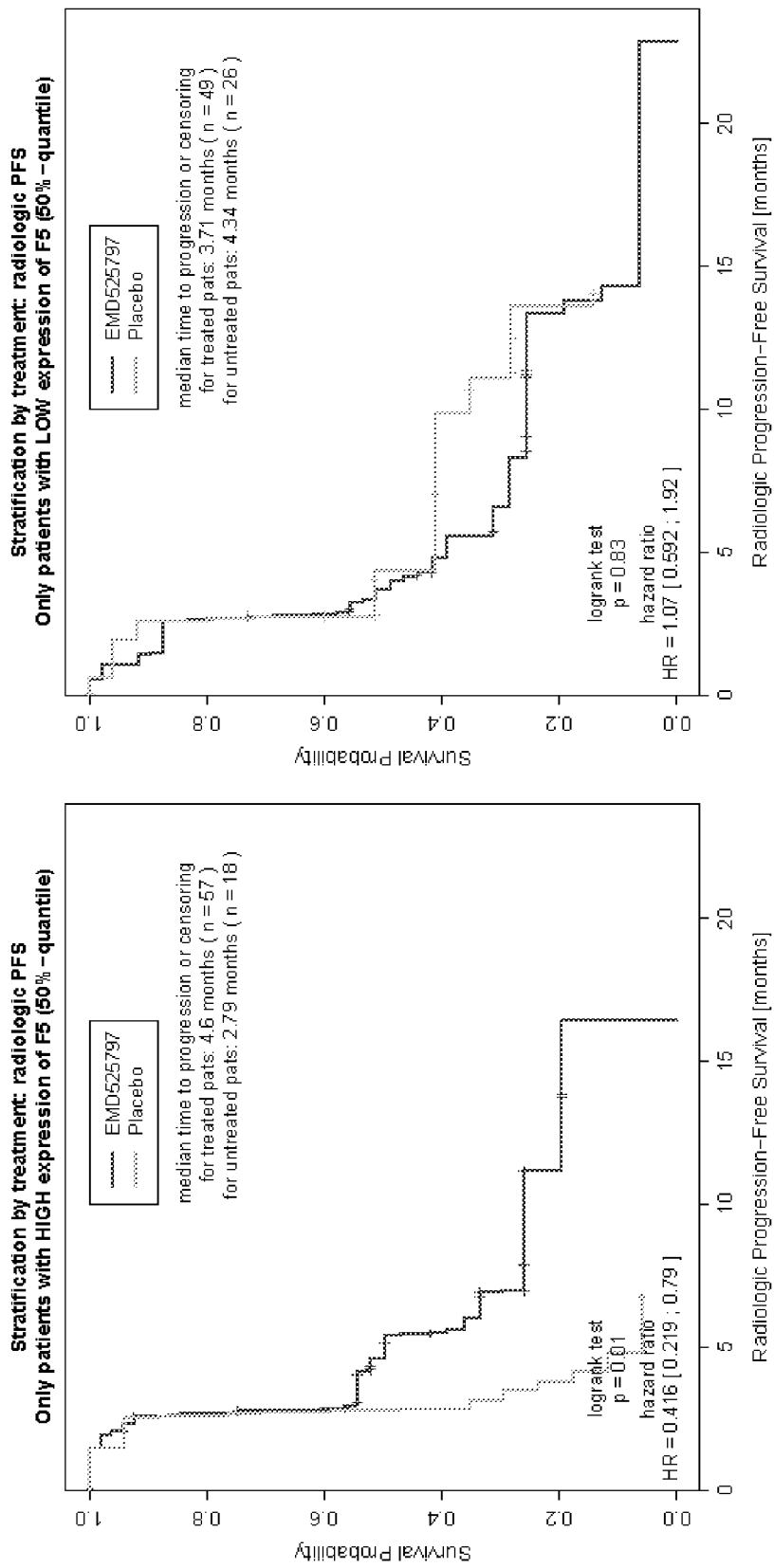
FIG. 18 displays rPFS of EMD 525797-treated patients and placebo-treated patients for high and low expressions of F5.
Figure 19:
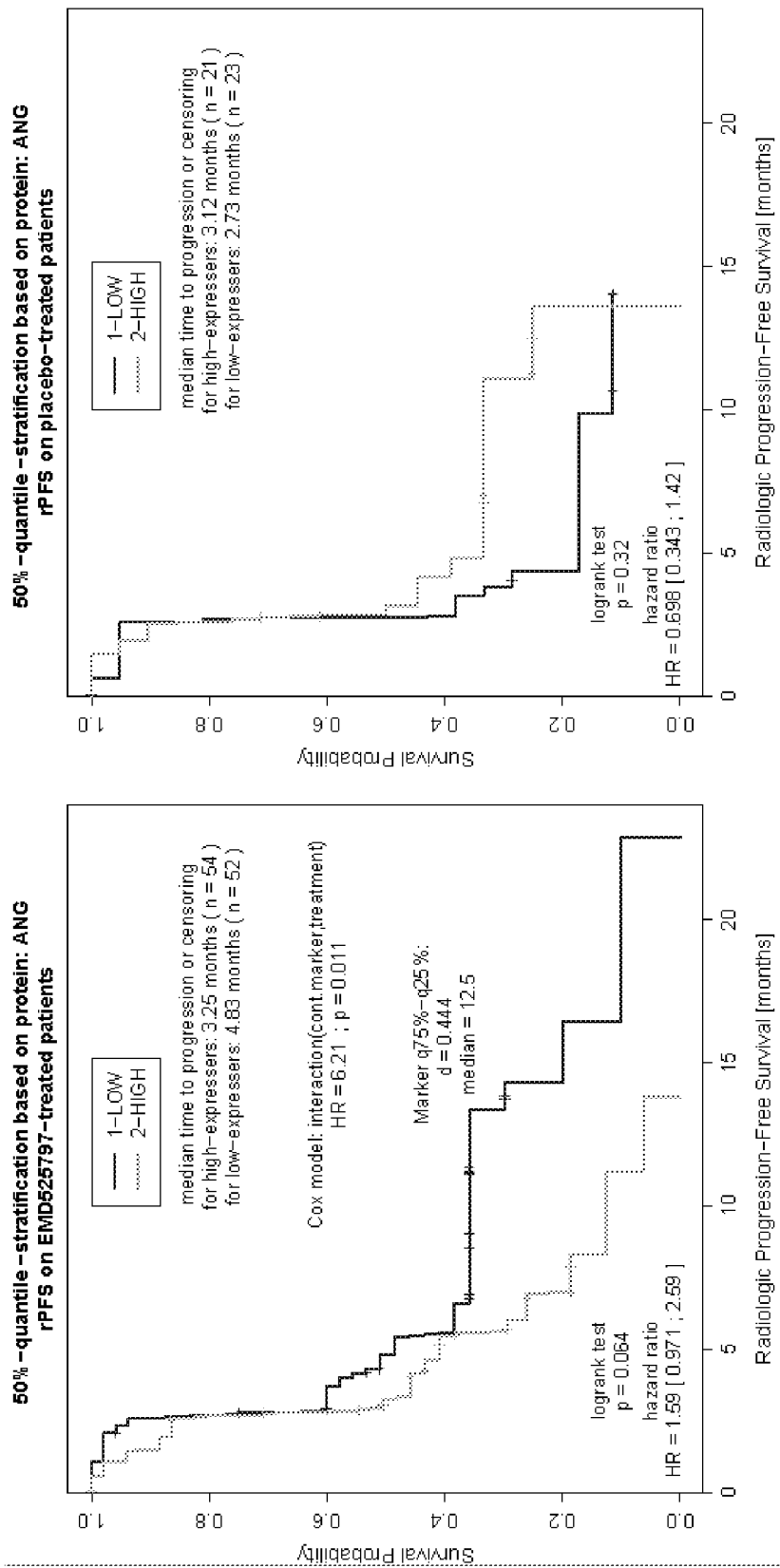
FIG. 19 displays rPFS of patients with high and low expressions of ANG for EMD 525797-treated patients and placebo-treated patients.
Figure 20:
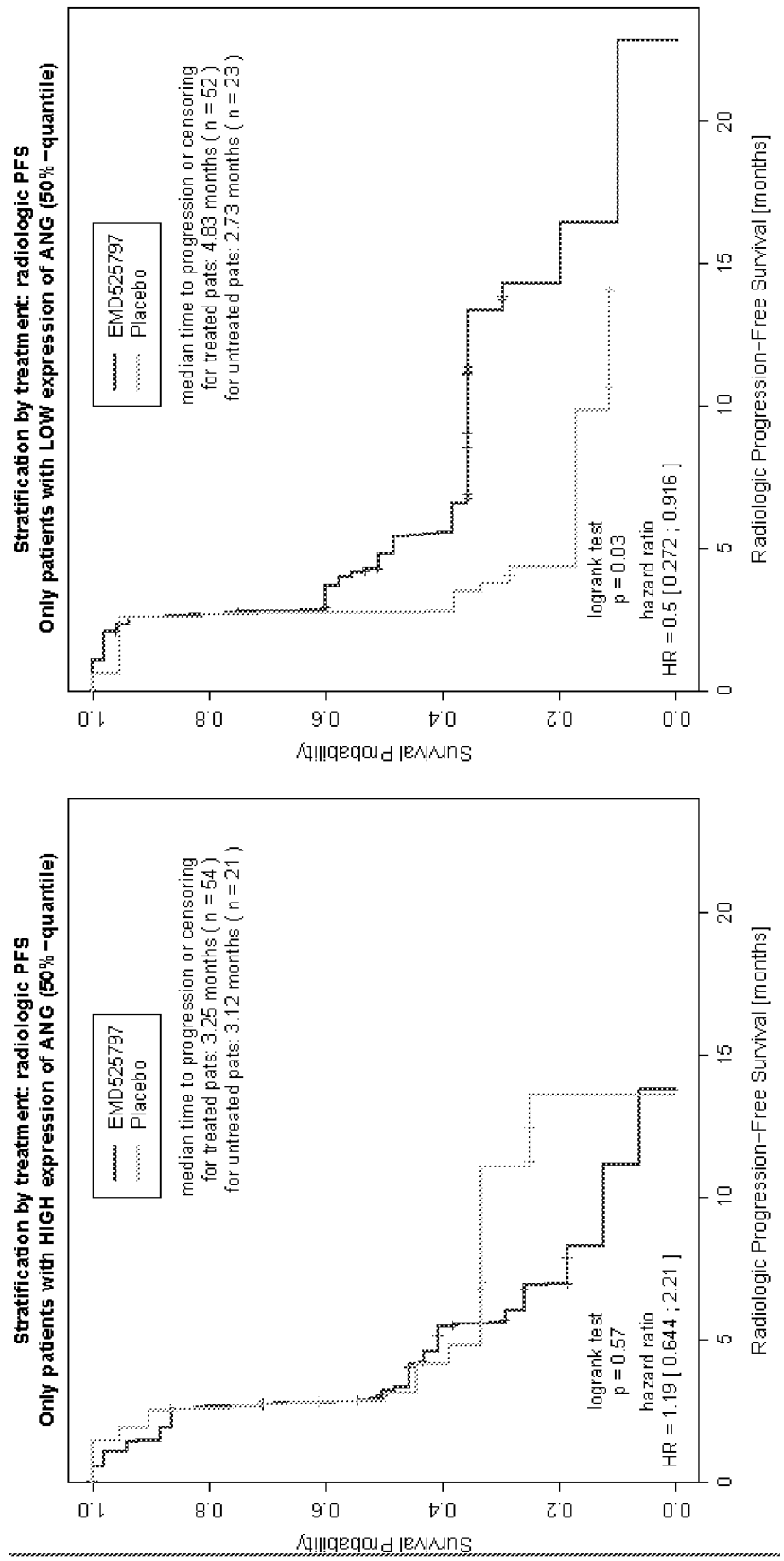
FIG. 20 displays rPFS of EMD 525797-treated patients and placebo-treated patients for high and low expressions of ANG.
Figure 21:
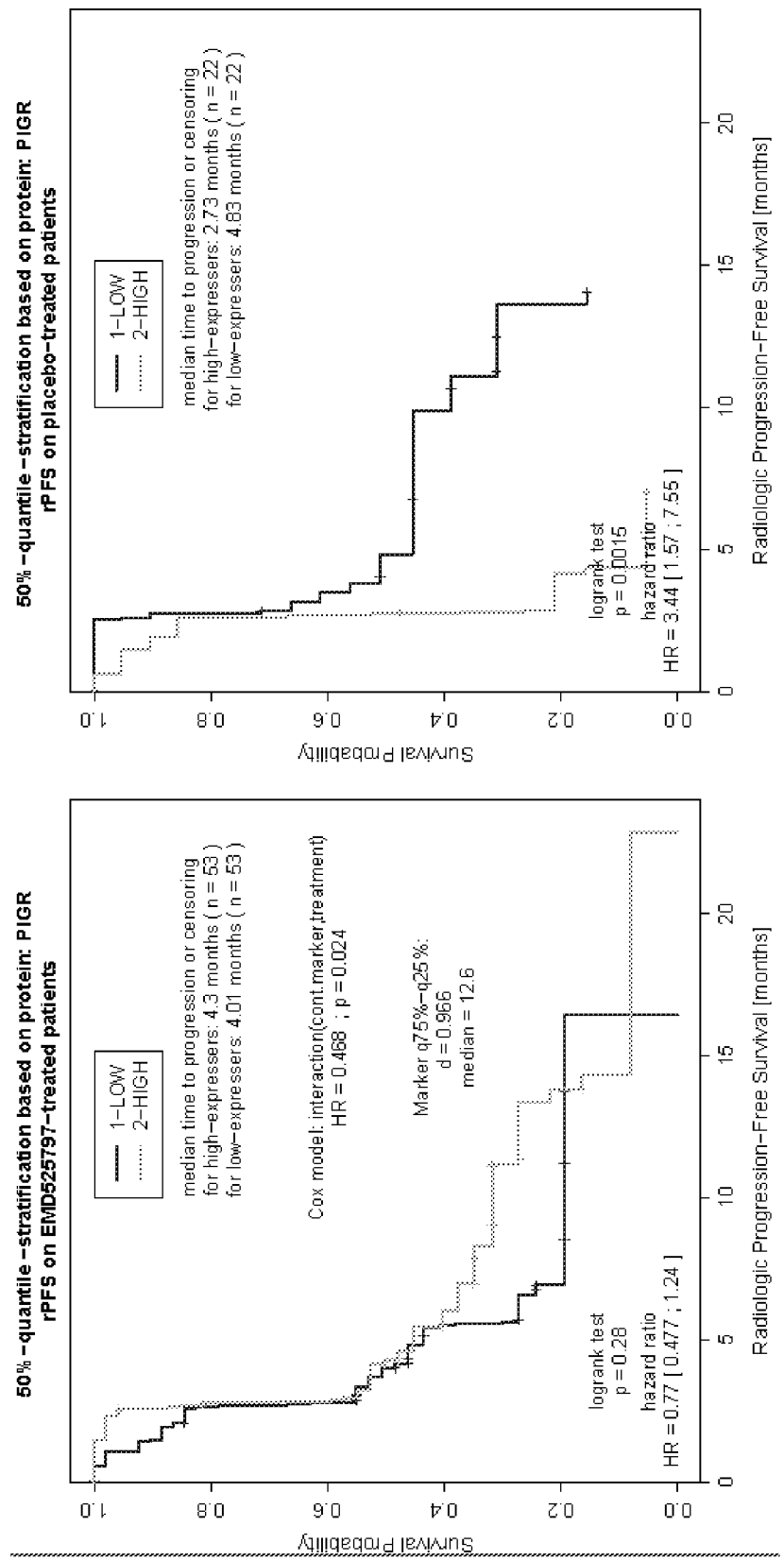
FIG. 21 displays rPFS of patients with high and low expressions of PIGR for EMD 525797-treated patients and placebo-treated patients.
Figure 22:
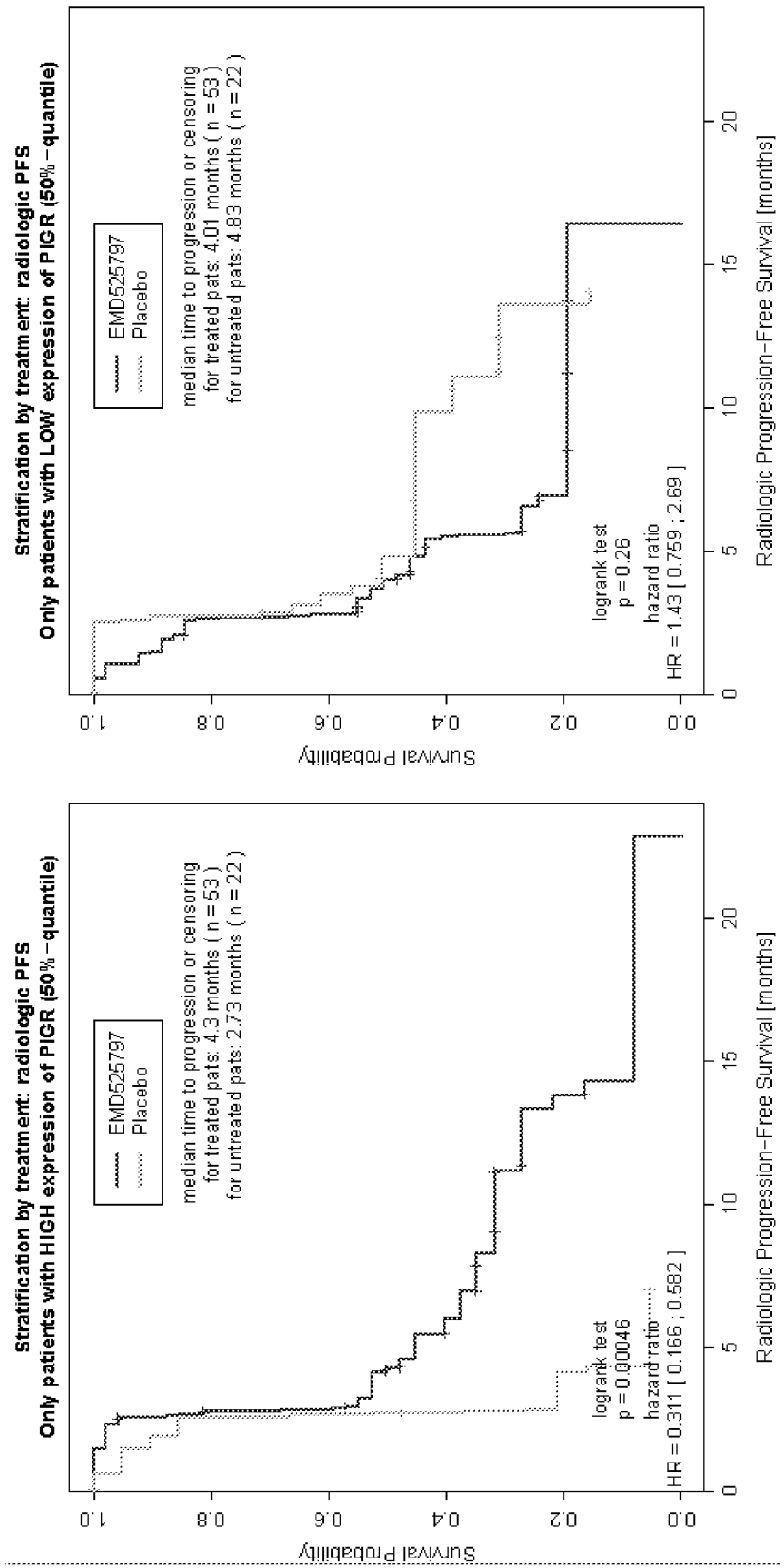
FIG. 22 displays rPFS of EMD 525797-treated patients and placebo-treated patients for high and low expressions of PIGR.
Figure 23:
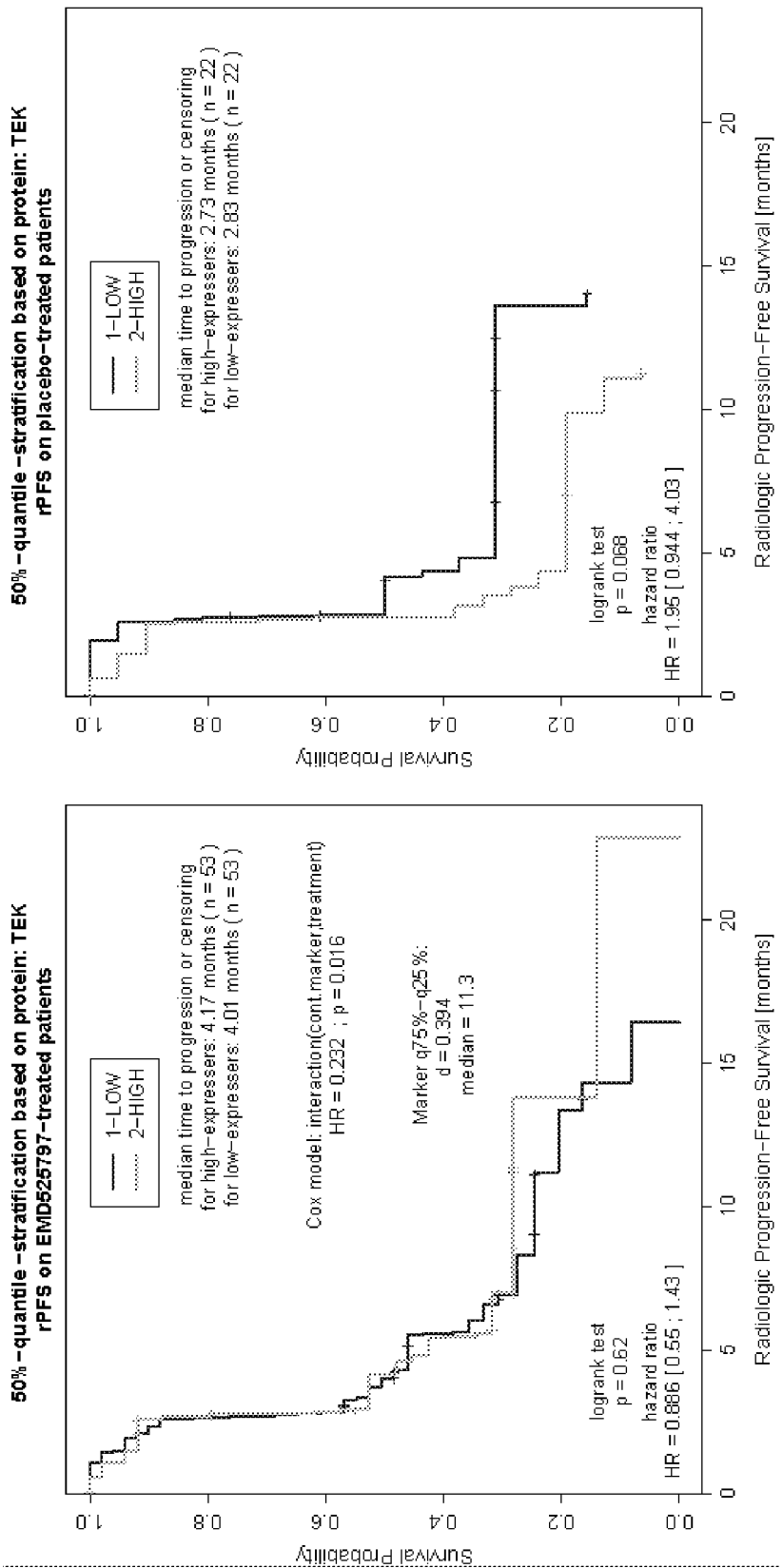
FIG. 23 displays rPFS of patients with high and low expressions of TEK for EMD 525797-treated patients and placebo-treated patients.
Figure 24:
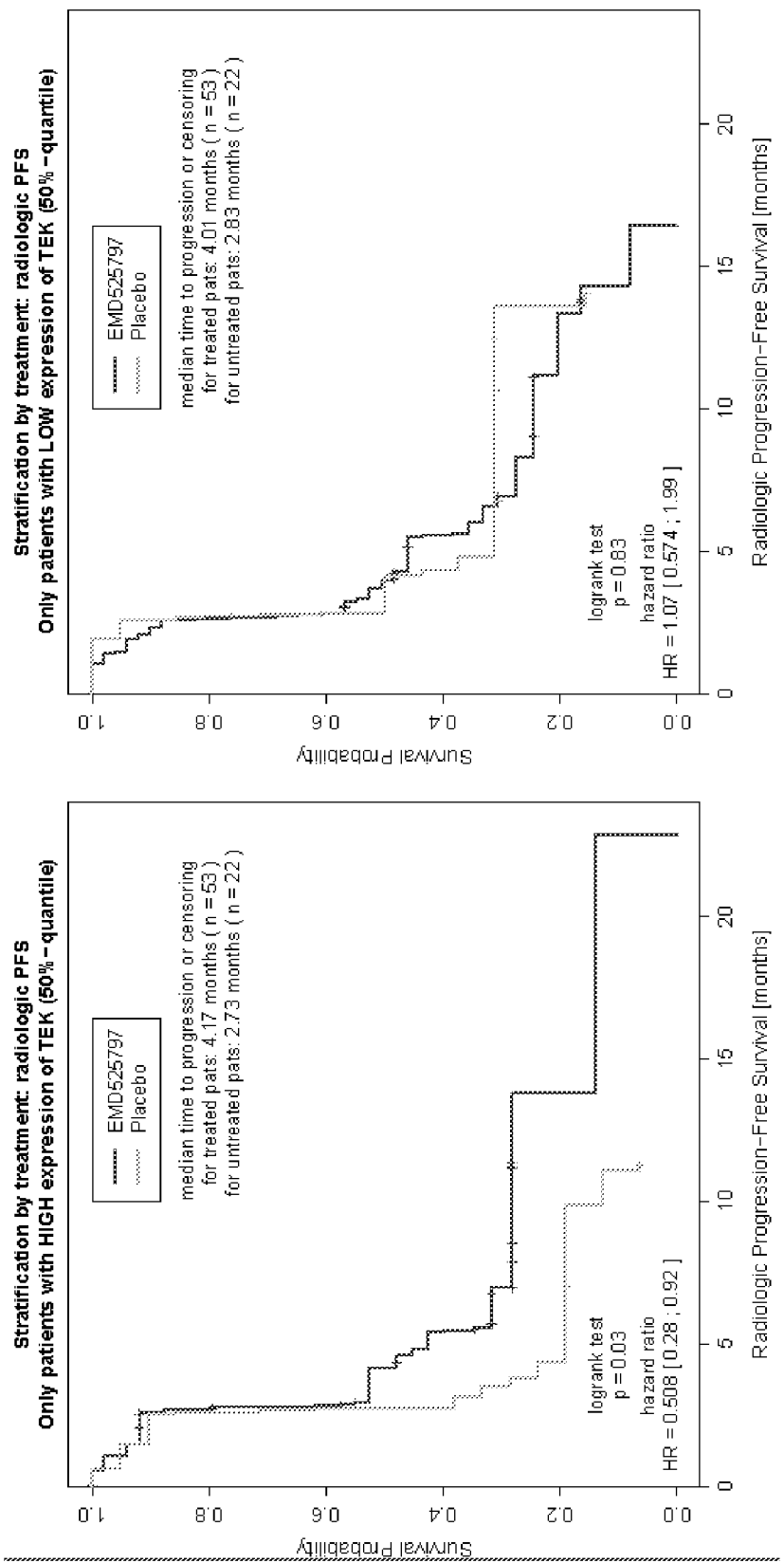
FIG. 24 displays rPFS of EMD 525797-treated patients and placebo-treated patients for high and low expressions of TEK.

The details documenting why the 14 biomarker plasma proteins identified are judged as active and whether levels above or below the median are judged as predictive are shown in Table 1, Table 2 and/or one or more of FIGS. 1 to 24.

The biomarker proteins include decorin (DCN), a protein known to have a role in TGF-β biology, as do some of the αv integrins inhibited by abituzumab Furthermore, analysis of the biological context of other markers indicated that markers related to known molecular interactions of abituzumab (bone metabolism modulation and angiogenesis) appeared to predict OS with abituzumab therapy.

Plasma levels of some of the identified 14 biomarker plasma proteins were prognostic under SoC of either good or poor survival and all 14 predicted increased survival with abituzumab compared to SoC alone. Table 1, Table 2 and/or one or more of FIGS. 1 to 24 show the prognostic and predictive value of the identified 14 predictive marker proteins, as for example TEK, for PFS.

Example 2

Proteomic Affinity Assay Method

All steps of the proteomic affinity assay are performed at room temperature unless otherwise indicated.

Sample thawing and plating.

Aliquots of 100% serum or EDTA- plasma, stored at −80° C., are thawed by incubating in a 25° C. water bath for ten minutes. After thawing the samples are stored on ice during mixing and prior to sample dilution. Samples are mixed by gentle vortexing (setting # 4 on Vortex Genie, Scientific Industries) for 8 seconds. A 20% sample solution is prepared by transferring 16 µL of thawed sample into 96-well plates (Hybaid Omnitube 0.3 mL, Thermo Fisher Scientific) containing 64 µL per well of the appropriate sample diluent at 4° C. Sample diluent for serum is 0.8× SB17 with 0.6 mM $MgCl_2$, 2 mM EGTA, 2 µM Z-Block_2, 0.05% Tween and for EDTA-plasma is 0.8× SB18 with 0.8 mM $MgCl_2$, 2 mM EGTA, 2 µM Z-Block_2, 0.05% Tween. This plate is stored on ice until the next sample dilution steps are initiated.

Preparation of 10%, 1% and 0.03% SOMAmer Solutions. SOMAmers are grouped into three unique mixes. The placing of a SOMAmer within a mix is empirically determined by assaying a dilution series of serum or plasma with each SOMAmer and identifying the sample dilution that gave the largest linear range of signal. The segregation of SOMAmers and mixing with different dilutions of sample (10%, 1% or 0.03%) allow the assay to span a $10^7$-fold range of protein concentration. The composition of the custom SOMAmer mixes is slightly different between plasma and serum as expected due to variation in protein composition of these two media. The custom stock SOMAmer solutions for 10%, 1% and 0.03% serum and plasma are prepared and stored at 8× concentration in SB17T. For each assay run, the three 8× SOMAmer solutions are diluted separately 1:4 into SB17T to achieve 2× concentration. Each diluted SOMAmer master mix is heated to 95° C. for five minutes and then to 37° C. for 15 minutes. 55 µL of each 2× SOMAmer mix is manually pipetted into a 96-well plate resulting in three plates with 10%, 1% or 0.03% SOMAmer mixes. After mixing with sample, the final individual SOMAmer concentration ranged from 0.25-4 nM for serum, 0.5 nM for plasma.

Equilibration. A 2% sample plate is prepared by diluting the 20% sample 1:10 into SB17T using the Beckman Coulter Biomek $Fx^P$ (Beckman Coulter). A 0.06% sample plate is prepared by diluting the 2% sample plate 1:31 into SB17T. The three sample dilutions are then transferred to their respective SOMAmer solutions by adding 55 µL of the sample to 55 µL of the appropriate 2× SOMAmer mix. The plates are sealed with a foil seal (Microseal 'F' Foil, Bio-Rad) and incubated at 37° C. for 3.5 hours.

Preparation of Catch-1 Bead Plates. 133.3 µL of a 7.5% Streptavidin-agarose bead slurry in SB17T is added to each well of three pre-washed 0.45 um filter plates. Each well of beads is washed once with 200 µL SB17T using vacuum filtration to remove the wash and then resuspended in 200 µL SB17T.

Catch-1 Bead Capture. All subsequent steps are performed by the Beckman Coulter Biomek $Fx^P$ robot unless otherwise noted. After the 3.5 hour equilibration, 100 µL of the 10%, 1% and 0.03% equilibration binding reactions is transferred to their respective Catch-1 Streptavidin agarose filter plates and incubated with shaking for ten minutes. Unbound solution is removed via vacuum filtration. Each set of Catch-1 beads is washed with 190 µL of 100 µM biotin in SB17T and then 190 mL of SB17T using vacuum filtration to remove the wash. 190 µL SB17T is added to each well in the Catch-1 plates and incubated with shaking for ten minutes at 25° C. The wash is removed via vacuum filtration and the bottom of the filter plates blotted to remove droplets using the on-deck blot station.

Biotinylation of Proteins. An aliquot of 100 mM NHS-PEO4-biotin in DMSO is thawed at 37° C. for six minutes and diluted to 1 mM with SB17T at pH 7.25. 100 µL of the NHSPEO4-biotin is added to each well of each Catch-1 filter plate and incubated with shaking for five minutes. Each biotinylation reaction is quenched by adding 150 µL of 20 mM glycine in SB17T to the Catch-1 plates with the NHS-PEO4-biotin. Plates are incubated for one minute with shaking, vacuum filtrated, and 190 µL 20 mM glycine SB17T is added to each well in the plate. The plates are incubated for one minute, shaking before removal by vacuum filtration. 190 µL of SB17T is added to each well and removed by vacuum filtration. The wells of the Catch-1 plates are subsequently washed three times by adding 190 µL SB17T, incubating for one minute with shaking followed by vacuum filtration. After the last wash the plates are centrifuged at 1000 rpm for one minute over a 1 mL deep-well plate to remove extraneous volume before elution. Centrifugation is performed off deck.

Kinetic Challenge and Photo-Cleavage. 85 µL of 10 mM dextran sulfate in SB17T is added to each well of the filter plates. The filter plates are placed onto a Thermal Shaker (Eppendorf) under a BlackRay light source and irradiated for ten minutes with shaking. The photo-cleaved solutions are sequentially eluted from each Catch-1 plate into a common deep well plate by centrifugation at 1000 rpm for one minute each.

Catch-2 Bead Capture. In bulk, MyOne-Streptavidin C1 beads are washed two times for 5 minutes each with equal volume of 20 mM NaOH and three times with an equal volume of SB17T. Beads are resuspended in SB17T to a concentration of 10 mg/mL. After resuspension, 50 µL of this solution is manually pipetted into each well of a 96-well plate and stored at 4° C. until Catch-2. During Catch-2, the wash supernatant is removed via magnetic separation. All of the photo-cleaved eluate is pipetted onto the MyOne magnetic beads and incubated with shaking at 25° C. for five minutes. The supernatant is removed from the MyOne beads via magnetic separation and 75 µL of SB17T is transferred to each well. The plate is mixed for one minute at 37° C. with shaking and then 75 µL of 60% glycerol (in SB17T) at 37° C. is transferred to each well. The plate is mixed for another minute at 37° C. with shaking. The wash is removed via magnetic separation. These washes are repeated two more times. After removal of the third glycerol wash from the MyOne beads, 150 µL of SB17T is added to each well and the plates incubated at 37° C. with shaking for one minute before removal by magnetic separation. The MyOne beads are washed a final time using 150 µL SB19T with incubation for one minute, prior to magnetic separation.

Catch-2 Bead Elution and Neutralization.

SOMAmers are eluted from MyOne beads by incubating each well of beads with 105 µL of 100 mM CAPSO pH 10, 1 M NaCl, 0.05% Tween with shaking for five minutes. 90 µL of each eluate is transferred during magnetic separation to a new 96-well plate containing 10 µL of 500 mM HCl, 500 mM HEPES, 0.05% Tween-20, pH 7.5.

Hybridization. 20 µL of each neutralized Catch-2 eluate is transferred to a new 96-well plate and 5 µL of 10× Agilent Block (Oligo aCGH/ChIP-on-chip Hybridization Kit, Large Volume, Agilent Technologies 5188-5380), containing a 10× spike of hybridization controls (10 Cy3 SOMAmers) is added to each well. After removing the plate from the robot, 25 µL of 2× Agilent Hybridization buffer (Oligo aCGH/ChIP-on-chip Hybridization Kit, Agilent Technologies) is manually pipetted to the each well of the plate containing the neutralized samples and blocking buffer. 40 µL of this solution is manually pipetted into each "well" of the hybridization gasket slide (Hybridization Gasket Slide—8 microarrays per slide format, Agilent Technologies). Custom Agilent microarray slides containing 10 probes per array complementary to 40 nucleotide selected region of each SOMAmer with a 20× dT linker are placed onto the gasket slides according to the manufacturer's protocol. Each assembly (Hybridization Chamber Kit—SureHyb enabled, Agilent Technologies) is tightly clamped and loaded into a hybridization oven for 19 hours at 60° C. rotating at 20 rpm.

Post-Hybridization Washing. Approximately 400 mL Wash Buffer 1 (Oligo aCGH/ChIP-on-chip Wash Buffer 1, Agilent Technologies) is placed into each of two separate glass staining dishes. Six of the twelve slide/gasket assemblies are sequentially disassembled into the first staining dish containing Wash Buffer 1.

Once disassembled, the slide is quickly transferred into a slide rack in a second staining dish containing Wash Buffer 1. The slides are incubated for five minutes in Wash Buffer 1 with mixing via magnetic stir bar. The slide rack is then transferred to the 37° C. Wash Buffer 2 (Oligo aCGH/ChIP-onchip Wash Buffer 2, Agilent Technologies) and allowed to incubate for five minutes with stirring. The slide rack is transferred to a fourth staining dish containing acetonitrile and incubated for five minutes with stirring.

Microarray Imaging. The microarray slides are imaged with a microarray scanner (Agilent G2565CA Microarray Scanner System, Agilent Technologies) in the Cy3-channel at 5 µm resolution at 100% PMT setting and the XRD option enabled at 0.05. The resulting tiff images are processed using Agilent feature extraction software version 10.5.1.1 with the GE1_105_Dec08 protocol.

---

SEQUENCE LISTING

<160> NUMBER OF SEQ ID NOS: 25

<210> SEQ ID NO 1
<211> LENGTH: 214
<212> TYPE: PRT
<213> ORGANISM: Artificial Sequence
<220> FEATURE:
<223> OTHER INFORMATION: DI17E6 light chain

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: DI17E6 heavy chain

<400> SEQUENCE: 2

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
                20                  25                  30

Trp Met His Trp Val Arg Gln Ala Pro Gly Gln Gly Leu Glu Trp Ile
            35                  40                  45

Gly Tyr Ile Asn Pro Arg Ser Gly Tyr Thr Glu Tyr Asn Glu Ile Phe
        50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Ser Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

```
Thr Lys Pro Arg Glu Glu Gln Ala Gln Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 3
<211> LENGTH: 15
<212> TYPE: PRT
<213> ORGANISM: Artificial Sequence
<220> FEATURE:
<223> OTHER INFORMATION: modified IgG1 hinge region

<400> SEQUENCE: 3

Glu Pro Lys Ser Ser Asp Lys Thr His Thr Cys Pro Pro Cys Pro
1               5                   10                  15

<210> SEQ ID NO 4
<211> LENGTH: 30
<212> TYPE: PRT
<213> ORGANISM: Artificial Sequence
<220> FEATURE:
<223> OTHER INFORMATION: heavy chain framework region

<400> SEQUENCE: 4

Gln Val Gln Leu Gln Gln Ser Gly Ala Glu Leu Ala Glu Pro Gly Ala
1               5                   10                  15

Ser Val Lys Met Ser Cys Lys Ala Ser Gly Tyr Thr Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: heavy chain framework region

<400> SEQUENCE: 5

Trp Val Lys Gln Arg Pro Gly Gln Gly Leu Glu Trp Ile Gly
1               5                   10

<210> SEQ ID NO 6
<211> LENGTH: 32
<212> TYPE: PRT
<213> ORGANISM: Artificial Sequence
<220> FEATURE:
<223> OTHER INFORMATION: heavy chain framework region
```

```
<400> SEQUENCE: 6

Lys Ala Thr Met Thr Ala Asp Thr Ser Ser Thr Ala Tyr Met Gln
1               5                   10                  15

Leu Ser Gly Leu Thr Ser Glu Asp Ser Ala Val Tyr Tyr Cys Ala Ser
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: heavy chain framework region

<400> SEQUENCE: 7

Trp Gly Gln Gly Thr Ser Val Thr Val Ser Ser
1               5                   10

<210> SEQ ID NO 8
<211> LENGTH: 119
<212> TYPE: PRT
<213> ORGANISM: Artificial Sequence
<220> FEATURE:
<223> OTHER INFORMATION: Sequence 7 from patent US 7550142

<400> SEQUENCE: 8

Gln Val Gln Leu Val Glu Ser Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 9
<211> LENGTH: 108
<212> TYPE: PRT
<213> ORGANISM: Artificial Sequence
<220> FEATURE:
<223> OTHER INFORMATION: Sequence 8 from patent US 7550142

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: Sequence 7 from patent US 7163681

<400> SEQUENCE: 10

Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 11
<211> LENGTH: 108
<212> TYPE: PRT
<213> ORGANISM: Artificial Sequence
<220> FEATURE:
<223> OTHER INFORMATION: Sequence 8 from patent US 7163681

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 12
<211> LENGTH: 147
<212> TYPE: PRT
<213> ORGANISM: Homo sapiens
```

```
<400> SEQUENCE: 12

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
                35                  40                  45

Tyr Cys Glu Ser Ile Met Arg Arg Gly Leu Thr Ser Pro Cys Lys
 50                  55                  60

Asp Ile Asn Thr Phe Ile His Gly Asn Lys Arg Ser Ile Lys Ala Ile
 65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
                115                 120                 125

Val Ala Cys Glu Asn Gly Leu Pro Val His Leu Asp Gln Ser Ile Phe
130                 135                 140

Arg Arg Pro
145

<210> SEQ ID NO 13
<211> LENGTH: 359
<212> TYPE: PRT
<213> ORGANISM: Homo sapiens

<400> SEQUENCE: 13

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
                35                  40                  45

Ser Leu Gly Pro Val Cys Pro Phe Arg Cys Gln Cys His Leu Arg Val
 50                  55                  60

Val Gln Cys Ser Asp Leu Gly Leu Asp Lys Val Pro Lys Asp Leu Pro
 65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
                100                 105                 110

Val Asn Asn Lys Ile Ser Lys Val Ser Pro Gly Ala Phe Thr Pro Leu
                115                 120                 125

Val Lys Leu Glu Arg Leu Tyr Leu Ser Lys Asn Gln Leu Lys Glu Leu
130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
                180                 185                 190

Asn Gly Ala Phe Gln Gly Met Lys Lys Leu Ser Tyr Ile Arg Ile Ala
                195                 200                 205
```

```
Asp Thr Asn Ile Thr Ser Ile Pro Gln Gly Leu Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
                260                 265                 270

Glu Leu His Leu Asp Asn Asn Lys Leu Thr Arg Val Pro Gly Gly Leu
                275                 280                 285

Ala Glu His Lys Tyr Ile Gln Val Val Tyr Leu His Asn Asn Asn Ile
290                 295                 300

Ser Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
                340                 345                 350

Ile Gln Leu Gly Asn Tyr Lys
            355

<210> SEQ ID NO 14
<211> LENGTH: 2224
<212> TYPE: PRT
<213> ORGANISM: Homo sapiens

<400> SEQUENCE: 14

Met Phe Pro Gly Cys Pro Arg Leu Trp Val Leu Val Val Leu Gly Thr
1               5                   10                  15

Ser Trp Val Gly Trp Gly Ser Gln Gly Thr Glu Ala Ala Gln Leu Arg
                20                  25                  30

Gln Phe Tyr Val Ala Ala Gln Gly Ile Ser Trp Ser Tyr Arg Pro Glu
            35                  40                  45

Pro Thr Asn Ser Ser Leu Asn Leu Ser Val Thr Ser Phe Lys Lys Ile
        50                  55                  60

Val Tyr Arg Glu Tyr Glu Pro Tyr Phe Lys Lys Glu Lys Pro Gln Ser
65                  70                  75                  80

Thr Ile Ser Gly Leu Leu Gly Pro Thr Leu Tyr Ala Glu Val Gly Asp
                85                  90                  95

Ile Ile Lys Val His Phe Lys Asn Lys Ala Asp Lys Pro Leu Ser Ile
                100                 105                 110

His Pro Gln Gly Ile Arg Tyr Ser Lys Leu Ser Glu Gly Ala Ser Tyr
            115                 120                 125

Leu Asp His Thr Phe Pro Ala Glu Lys Met Asp Asp Ala Val Ala Pro
130                 135                 140

Gly Arg Glu Tyr Thr Tyr Glu Trp Ser Ile Ser Glu Asp Ser Gly Pro
145                 150                 155                 160

Thr His Asp Asp Pro Pro Cys Leu Thr His Ile Tyr Tyr Ser His Glu
                165                 170                 175

Asn Leu Ile Glu Asp Phe Asn Ser Gly Leu Ile Gly Pro Leu Leu Ile
            180                 185                 190

Cys Lys Lys Gly Thr Leu Thr Glu Gly Gly Thr Gln Lys Thr Phe Asp
        195                 200                 205

Lys Gln Ile Val Leu Leu Phe Ala Val Phe Asp Glu Ser Lys Ser Trp
210                 215                 220
```

```
Ser Gln Ser Ser Ser Leu Met Tyr Thr Val Asn Gly Tyr Val Asn Gly
225                 230                 235                 240
Thr Met Pro Asp Ile Thr Val Cys Ala His Asp His Ile Ser Trp His
            245                 250                 255
Leu Leu Gly Met Ser Ser Gly Pro Glu Leu Phe Ser Ile His Phe Asn
            260                 265                 270
Gly Gln Val Leu Glu Gln Asn His His Lys Val Ser Ala Ile Thr Leu
        275                 280                 285
Val Ser Ala Thr Ser Thr Thr Ala Asn Met Thr Val Gly Pro Glu Gly
        290                 295                 300
Lys Trp Ile Ile Ser Ser Leu Thr Pro Lys His Leu Gln Ala Gly Met
305                 310                 315                 320
Gln Ala Tyr Ile Asp Ile Lys Asn Cys Pro Lys Lys Thr Arg Asn Leu
            325                 330                 335
Lys Lys Ile Thr Arg Glu Gln Arg Arg His Met Lys Arg Trp Glu Tyr
            340                 345                 350
Phe Ile Ala Ala Glu Glu Val Ile Trp Asp Tyr Ala Pro Val Ile Pro
            355                 360                 365
Ala Asn Met Asp Lys Lys Tyr Arg Ser Gln His Leu Asp Asn Phe Ser
370                 375                 380
Asn Gln Ile Gly Lys His Tyr Lys Lys Val Met Tyr Thr Gln Tyr Glu
385                 390                 395                 400
Asp Glu Ser Phe Thr Lys His Thr Val Asn Pro Asn Met Lys Glu Asp
            405                 410                 415
Gly Ile Leu Gly Pro Ile Ile Arg Ala Gln Val Arg Asp Thr Leu Lys
            420                 425                 430
Ile Val Phe Lys Asn Met Ala Ser Arg Pro Tyr Ser Ile Tyr Pro His
            435                 440                 445
Gly Val Thr Phe Ser Pro Tyr Glu Asp Glu Val Asn Ser Ser Phe Thr
            450                 455                 460
Ser Gly Arg Asn Asn Thr Met Ile Arg Ala Val Gln Pro Gly Glu Thr
465                 470                 475                 480
Tyr Thr Tyr Lys Trp Asn Ile Leu Glu Phe Asp Glu Pro Thr Glu Asn
            485                 490                 495
Asp Ala Gln Cys Leu Thr Arg Pro Tyr Tyr Ser Asp Val Asp Ile Met
            500                 505                 510
Arg Asp Ile Ala Ser Gly Leu Ile Gly Leu Leu Leu Ile Cys Lys Ser
            515                 520                 525
Arg Ser Leu Asp Arg Arg Gly Ile Gln Arg Ala Ala Asp Ile Glu Gln
        530                 535                 540
Gln Ala Val Phe Ala Val Phe Asp Glu Asn Lys Ser Trp Tyr Leu Glu
545                 550                 555                 560
Asp Asn Ile Asn Lys Phe Cys Glu Asn Pro Asp Glu Val Lys Arg Asp
            565                 570                 575
Asp Pro Lys Phe Tyr Glu Ser Asn Ile Met Ser Thr Ile Asn Gly Tyr
            580                 585                 590
Val Pro Glu Ser Ile Thr Thr Leu Gly Phe Cys Phe Asp Asp Thr Val
            595                 600                 605
Gln Trp His Phe Cys Ser Val Gly Thr Gln Asn Glu Ile Leu Thr Ile
            610                 615                 620
His Phe Thr Gly His Ser Phe Ile Tyr Gly Lys Arg His Glu Asp Thr
625                 630                 635                 640
```

-continued

```
Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Gly Ser Thr Val Met
    690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Glu Phe Asn
            740                 745                 750

Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
    770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815

Asn Ser Val Leu Asn Ser Ser Thr Ala Glu His Ser Ser Pro Tyr Ser
            820                 825                 830

Glu Asp Pro Ile Glu Asp Pro Leu Gln Pro Asp Val Thr Gly Ile Arg
        835                 840                 845

Leu Leu Ser Leu Gly Ala Gly Glu Phe Lys Ser Gln Glu His Ala Lys
    850                 855                 860

His Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Lys Asp Pro Pro
        915                 920                 925

Ser Asp Leu Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
            980                 985                 990

Gly Lys Gln Ser Gly His Pro Lys Phe Pro Arg Val Arg His Lys Ser
        995                 1000                1005

Leu Gln Val Arg Gln Asp Gly Gly Lys Ser Arg Leu Lys Lys Ser
        1010                1015                1020

Gln Phe Leu Ile Lys Thr Arg Lys Lys Lys Lys Glu Lys His Thr
        1025                1030                1035

His His Ala Pro Leu Ser Pro Arg Thr Phe His Pro Leu Arg Ser
        1040                1045                1050
```

-continued

```
Glu Ala Tyr Asn Thr Phe Ser Glu Arg Arg Leu Lys His Ser Leu
1055                    1060                1065

Val Leu His Lys Ser Asn Glu Thr Ser Leu Pro Thr Asp Leu Asn
1070                    1075                1080

Gln Thr Leu Pro Ser Met Asp Phe Gly Trp Ile Ala Ser Leu Pro
1085                    1090                1095

Asp His Asn Gln Asn Ser Ser Asn Asp Thr Gly Gln Ala Ser Cys
1100                    1105                1110

Pro Pro Gly Leu Tyr Gln Thr Val Pro Pro Glu Glu His Tyr Gln
1115                    1120                1125

Thr Phe Pro Ile Gln Asp Pro Asp Gln Met His Ser Thr Ser Asp
1130                    1135                1140

Pro Ser His Arg Ser Ser Ser Pro Glu Leu Ser Glu Met Leu Glu
1145                    1150                1155

Tyr Asp Arg Ser His Lys Ser Phe Pro Thr Asp Ile Ser Gln Met
1160                    1165                1170

Ser Pro Ser Ser Glu His Glu Val Trp Gln Thr Val Ile Ser Pro
1175                    1180                1185

Asp Leu Ser Gln Val Thr Leu Ser Pro Glu Leu Ser Gln Thr Asn
1190                    1195                1200

Leu Ser Pro Asp Leu Ser His Thr Thr Leu Ser Pro Glu Leu Ile
1205                    1210                1215

Gln Arg Asn Leu Ser Pro Ala Leu Gly Gln Met Pro Ile Ser Pro
1220                    1225                1230

Asp Leu Ser His Thr Thr Leu Ser Pro Asp Leu Ser His Thr Thr
1235                    1240                1245

Leu Ser Leu Asp Leu Ser Gln Thr Asn Leu Ser Pro Glu Leu Ser
1250                    1255                1260

Gln Thr Asn Leu Ser Pro Ala Leu Gly Gln Met Pro Leu Ser Pro
1265                    1270                1275

Asp Leu Ser His Thr Thr Leu Ser Leu Asp Phe Ser Gln Thr Asn
1280                    1285                1290

Leu Ser Pro Glu Leu Ser His Met Thr Leu Ser Pro Glu Leu Ser
1295                    1300                1305

Gln Thr Asn Leu Ser Pro Ala Leu Gly Gln Met Pro Ile Ser Pro
1310                    1315                1320

Asp Leu Ser His Thr Thr Leu Ser Leu Asp Phe Ser Gln Thr Asn
1325                    1330                1335

Leu Ser Pro Glu Leu Ser Gln Thr Asn Leu Ser Pro Ala Leu Gly
1340                    1345                1350

Gln Met Pro Leu Ser Pro Asp Pro Ser His Thr Thr Leu Ser Leu
1355                    1360                1365

Asp Leu Ser Gln Thr Asn Leu Ser Pro Glu Leu Ser Gln Thr Asn
1370                    1375                1380

Leu Ser Pro Asp Leu Ser Glu Met Pro Leu Phe Ala Asp Leu Ser
1385                    1390                1395

Gln Ile Pro Leu Thr Pro Asp Leu Asp Gln Met Thr Leu Ser Pro
1400                    1405                1410

Asp Leu Gly Glu Thr Asp Leu Ser Pro Asn Phe Gly Gln Met Ser
1415                    1420                1425

Leu Ser Pro Asp Leu Ser Gln Val Thr Leu Ser Pro Asp Ile Ser
1430                    1435                1440
```

```
Asp Thr Thr Leu Leu Pro Asp Leu Ser Gln Ile Ser Pro Pro Pro
    1445                1450                1455

Asp Leu Asp Gln Ile Phe Tyr Pro Ser Glu Ser Ser Gln Ser Leu
    1460                1465                1470

Leu Leu Gln Glu Phe Asn Glu Ser Phe Pro Tyr Pro Asp Leu Gly
    1475                1480                1485

Gln Met Pro Ser Pro Ser Ser Pro Thr Leu Asn Asp Thr Phe Leu
    1490                1495                1500

Ser Lys Glu Phe Asn Pro Leu Val Ile Val Gly Leu Ser Lys Asp
    1505                1510                1515

Gly Thr Asp Tyr Ile Glu Ile Ile Pro Lys Glu Glu Val Gln Ser
    1520                1525                1530

Ser Glu Asp Asp Tyr Ala Glu Ile Asp Tyr Val Pro Tyr Asp Asp
    1535                1540                1545

Pro Tyr Lys Thr Asp Val Arg Thr Asn Ile Asn Ser Ser Arg Asp
    1550                1555                1560

Pro Asp Asn Ile Ala Ala Trp Tyr Leu Arg Ser Asn Asn Gly Asn
    1565                1570                1575

Arg Arg Asn Tyr Tyr Ile Ala Ala Glu Glu Ile Ser Trp Asp Tyr
    1580                1585                1590

Ser Glu Phe Val Gln Arg Glu Thr Asp Ile Glu Asp Ser Asp Asp
    1595                1600                1605

Ile Pro Glu Asp Thr Thr Tyr Lys Lys Val Val Phe Arg Lys Tyr
    1610                1615                1620

Leu Asp Ser Thr Phe Thr Lys Arg Asp Pro Arg Gly Glu Tyr Glu
    1625                1630                1635

Glu His Leu Gly Ile Leu Gly Pro Ile Ile Arg Ala Glu Val Asp
    1640                1645                1650

Asp Val Ile Gln Val Arg Phe Lys Asn Leu Ala Ser Arg Pro Tyr
    1655                1660                1665

Ser Leu His Ala His Gly Leu Ser Tyr Glu Lys Ser Ser Glu Gly
    1670                1675                1680

Lys Thr Tyr Glu Asp Asp Ser Pro Glu Trp Phe Lys Glu Asp Asn
    1685                1690                1695

Ala Val Gln Pro Asn Ser Ser Tyr Thr Tyr Val Trp His Ala Thr
    1700                1705                1710

Glu Arg Ser Gly Pro Glu Ser Pro Gly Ser Ala Cys Arg Ala Trp
    1715                1720                1725

Ala Tyr Tyr Ser Ala Val Asn Pro Glu Lys Asp Ile His Ser Gly
    1730                1735                1740

Leu Ile Gly Pro Leu Leu Ile Cys Gln Lys Gly Ile Leu His Lys
    1745                1750                1755

Asp Ser Asn Met Pro Met Asp Met Arg Glu Phe Val Leu Leu Phe
    1760                1765                1770

Met Thr Phe Asp Glu Lys Lys Ser Trp Tyr Tyr Glu Lys Lys Ser
    1775                1780                1785

Arg Ser Ser Trp Arg Leu Thr Ser Ser Glu Met Lys Lys Ser His
    1790                1795                1800

Glu Phe His Ala Ile Asn Gly Met Ile Tyr Ser Leu Pro Gly Leu
    1805                1810                1815

Lys Met Tyr Glu Gln Glu Trp Val Arg Leu His Leu Leu Asn Ile
    1820                1825                1830
```

Gly Gly Ser Gln Asp Ile His Val Val His Phe His Gly Gln Thr
1835                1840                1845

Leu Leu Glu Asn Gly Asn Lys Gln His Gln Leu Gly Val Trp Pro
1850                1855                1860

Leu Leu Pro Gly Ser Phe Lys Thr Leu Glu Met Lys Ala Ser Lys
1865                1870                1875

Pro Gly Trp Trp Leu Leu Asn Thr Glu Val Gly Glu Asn Gln Arg
1880                1885                1890

Ala Gly Met Gln Thr Pro Phe Leu Ile Met Asp Arg Asp Cys Arg
1895                1900                1905

Met Pro Met Gly Leu Ser Thr Gly Ile Ile Ser Asp Ser Gln Ile
1910                1915                1920

Lys Ala Ser Glu Phe Leu Gly Tyr Trp Glu Pro Arg Leu Ala Arg
1925                1930                1935

Leu Asn Asn Gly Gly Ser Tyr Asn Ala Trp Ser Val Glu Lys Leu
1940                1945                1950

Ala Ala Glu Phe Ala Ser Lys Pro Trp Ile Gln Val Asp Met Gln
1955                1960                1965

Lys Glu Val Ile Ile Thr Gly Ile Gln Thr Gln Gly Ala Lys His
1970                1975                1980

Tyr Leu Lys Ser Cys Tyr Thr Thr Glu Phe Tyr Val Ala Tyr Ser
1985                1990                1995

Ser Asn Gln Ile Asn Trp Gln Ile Phe Lys Gly Asn Ser Thr Arg
2000                2005                2010

Asn Val Met Tyr Phe Asn Gly Asn Ser Asp Ala Ser Thr Ile Lys
2015                2020                2025

Glu Asn Gln Phe Asp Pro Pro Ile Val Ala Arg Tyr Ile Arg Ile
2030                2035                2040

Ser Pro Thr Arg Ala Tyr Asn Arg Pro Thr Leu Arg Leu Glu Leu
2045                2050                2055

Gln Gly Cys Glu Val Asn Gly Cys Ser Thr Pro Leu Gly Met Glu
2060                2065                2070

Asn Gly Lys Ile Glu Asn Lys Gln Ile Thr Ala Ser Ser Phe Lys
2075                2080                2085

Lys Ser Trp Trp Gly Asp Tyr Trp Glu Pro Phe Arg Ala Arg Leu
2090                2095                2100

Asn Ala Gln Gly Arg Val Asn Ala Trp Gln Ala Lys Ala Asn Asn
2105                2110                2115

Asn Lys Gln Trp Leu Glu Ile Asp Leu Leu Lys Ile Lys Lys Ile
2120                2125                2130

Thr Ala Ile Ile Thr Gln Gly Cys Lys Ser Leu Ser Ser Glu Met
2135                2140                2145

Tyr Val Lys Ser Tyr Thr Ile His Tyr Ser Glu Gln Gly Val Glu
2150                2155                2160

Trp Lys Pro Tyr Arg Leu Lys Ser Ser Met Val Asp Lys Ile Phe
2165                2170                2175

Glu Gly Asn Thr Asn Thr Lys Gly His Val Lys Asn Phe Phe Asn
2180                2185                2190

Pro Pro Ile Ile Ser Arg Phe Ile Arg Val Ile Pro Lys Thr Trp
2195                2200                2205

Asn Gln Ser Ile Ala Leu Arg Leu Glu Leu Phe Gly Cys Asp Ile
2210                2215                2220

Tyr

```
<210> SEQ ID NO 15
<211> LENGTH: 269
<212> TYPE: PRT
<213> ORGANISM: Homo sapiens

<400> SEQUENCE: 15

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 16
<211> LENGTH: 1165
<212> TYPE: PRT
<213> ORGANISM: Homo sapiens

<400> SEQUENCE: 16

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60
```

-continued

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

```
Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Thr Cys
            515                 520                 525

Val Leu Pro Asp Ser Val Val Lys Pro Leu Pro Pro Ser Ser Val Lys
            530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
            595                 600                 605

Val Gln Val Arg Cys Lys Arg Leu Asp Gly Leu Gly Tyr Trp Ser Asn
            610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
            690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
            770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
            835                 840                 845

Ile Ile Ser Ser Ser Ile Leu Leu Leu Gly Thr Leu Leu Ile Ser His
            850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895
```

-continued

His Leu Phe Ile Lys His Thr Ala Ser Val Thr Cys Gly Pro Leu Leu
                900                 905                 910

Leu Glu Pro Glu Thr Ile Ser Glu Asp Ile Ser Val Asp Thr Ser Trp
            915                 920                 925

Lys Asn Lys Asp Glu Met Met Pro Thr Thr Val Val Ser Leu Leu Ser
        930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
        995                 1000                1005

Val Thr Lys Cys Phe Ser Ser Lys Asn Ser Pro Leu Lys Asp Ser
    1010                1015                1020

Phe Ser Asn Ser Ser Trp Glu Ile Glu Ala Gln Ala Phe Phe Ile
    1025                1030                1035

Leu Ser Asp Gln His Pro Asn Ile Ile Ser Pro His Leu Thr Phe
    1040                1045                1050

Ser Glu Gly Leu Asp Glu Leu Leu Lys Leu Glu Gly Asn Phe Pro
    1055                1060                1065

Glu Glu Asn Asn Asp Lys Lys Ser Ile Tyr Tyr Leu Gly Val Thr
    1070                1075                1080

Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 17
<211> LENGTH: 400
<212> TYPE: PRT
<213> ORGANISM: Homo sapiens

<400> SEQUENCE: 17

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
    130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400

<210> SEQ ID NO 18
<211> LENGTH: 364
<212> TYPE: PRT
<213> ORGANISM: Homo sapiens

<400> SEQUENCE: 18

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80

-continued

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
            115                 120                 125

Phe Leu Val Tyr Gln Leu Leu Arg Gly Leu Lys Tyr Ile His Ser Ala
        130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Gln Gly Lys Ala Leu Phe Pro
    210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
            260                 265                 270

Ile Phe Arg Gly Ala Asn Pro Leu Ala Ile Asp Leu Leu Gly Arg Met
        275                 280                 285

Leu Val Leu Asp Ser Asp Gln Arg Val Ser Ala Ala Glu Ala Leu Ala
    290                 295                 300

His Ala Tyr Phe Ser Gln Tyr His Asp Pro Glu Asp Glu Pro Glu Ala
305                 310                 315                 320

Glu Pro Tyr Asp Glu Ser Val Glu Ala Lys Glu Arg Thr Leu Glu Glu
                325                 330                 335

Trp Lys Glu Leu Thr Tyr Gln Glu Val Leu Ser Phe Lys Pro Pro Glu
            340                 345                 350

Pro Pro Lys Pro Pro Gly Ser Leu Glu Ile Glu Gln
        355                 360

<210> SEQ ID NO 19
<211> LENGTH: 764
<212> TYPE: PRT
<213> ORGANISM: Homo sapiens

<400> SEQUENCE: 19

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

```
Ile Ala Gln Leu Ser Gln Asp Asp Ser Gly Arg Tyr Lys Cys Gly Leu
                100                 105                 110
Gly Ile Asn Ser Arg Gly Leu Ser Phe Asp Val Ser Leu Glu Val Ser
            115                 120                 125
Gln Gly Pro Gly Leu Leu Asn Asp Thr Lys Val Tyr Thr Val Asp Leu
        130                 135                 140
Gly Arg Thr Val Thr Ile Asn Cys Pro Phe Lys Thr Glu Asn Ala Gln
145                 150                 155                 160
Lys Arg Lys Ser Leu Tyr Lys Gln Ile Gly Leu Tyr Pro Val Leu Val
                165                 170                 175
Ile Asp Ser Ser Gly Tyr Val Asn Pro Asn Tyr Thr Gly Arg Ile Arg
            180                 185                 190
Leu Asp Ile Gln Gly Thr Gly Gln Leu Leu Phe Ser Val Val Ile Asn
        195                 200                 205
Gln Leu Arg Leu Ser Asp Ala Gly Gln Tyr Leu Cys Gln Ala Gly Asp
210                 215                 220
Asp Ser Asn Ser Asn Lys Lys Asn Ala Asp Leu Gln Val Leu Lys Pro
225                 230                 235                 240
Glu Pro Glu Leu Val Tyr Glu Asp Leu Arg Gly Ser Val Thr Phe His
                245                 250                 255
Cys Ala Leu Gly Pro Glu Val Ala Asn Val Ala Lys Phe Leu Cys Arg
            260                 265                 270
Gln Ser Ser Gly Glu Asn Cys Asp Val Val Val Asn Thr Leu Gly Lys
        275                 280                 285
Arg Ala Pro Ala Phe Glu Gly Arg Ile Leu Leu Asn Pro Gln Asp Lys
290                 295                 300
Asp Gly Ser Phe Ser Val Val Ile Thr Gly Leu Arg Lys Glu Asp Ala
305                 310                 315                 320
Gly Arg Tyr Leu Cys Gly Ala His Ser Asp Gly Gln Leu Gln Glu Gly
                325                 330                 335
Ser Pro Ile Gln Ala Trp Gln Leu Phe Val Asn Glu Glu Ser Thr Ile
            340                 345                 350
Pro Arg Ser Pro Thr Val Val Lys Gly Val Ala Gly Gly Ser Val Ala
        355                 360                 365
Val Leu Cys Pro Tyr Asn Arg Lys Glu Ser Lys Ser Ile Lys Tyr Trp
370                 375                 380
Cys Leu Trp Glu Gly Ala Gln Asn Gly Arg Cys Pro Leu Leu Val Asp
385                 390                 395                 400
Ser Glu Gly Trp Val Lys Ala Gln Tyr Glu Gly Arg Leu Ser Leu Leu
                405                 410                 415
Glu Glu Pro Gly Asn Gly Thr Phe Thr Val Ile Leu Asn Gln Leu Thr
            420                 425                 430
Ser Arg Asp Ala Gly Phe Tyr Trp Cys Leu Thr Asn Gly Asp Thr Leu
        435                 440                 445
Trp Arg Thr Thr Val Glu Ile Lys Ile Ile Glu Gly Glu Pro Asn Leu
450                 455                 460
Lys Val Pro Gly Asn Val Thr Ala Val Leu Gly Glu Thr Leu Lys Val
465                 470                 475                 480
Pro Cys His Phe Pro Cys Lys Phe Ser Ser Tyr Glu Lys Tyr Trp Cys
                485                 490                 495
Lys Trp Asn Asn Thr Gly Cys Gln Ala Leu Pro Ser Gln Asp Glu Gly
            500                 505                 510
```

-continued

Pro Ser Lys Ala Phe Val Asn Cys Asp Glu Asn Ser Arg Leu Val Ser
    515                 520                 525

Leu Thr Leu Asn Leu Val Thr Arg Ala Asp Glu Gly Trp Tyr Trp Cys
530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
                580                 585                 590

Glu Ile Glu Asn Lys Ala Ile Gln Asp Pro Arg Leu Phe Ala Glu Glu
            595                 600                 605

Lys Ala Val Ala Asp Thr Arg Asp Gln Ala Asp Gly Ser Arg Ala Ser
        610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760

<210> SEQ ID NO 20
<211> LENGTH: 437
<212> TYPE: PRT
<213> ORGANISM: Homo sapiens

<400> SEQUENCE: 20

Met Gly Leu Arg Ala Ala Pro Ser Ser Ala Ala Ala Ala Ala Ala Glu
1               5                   10                  15

Val Glu Gln Arg Arg Ser Pro Gly Leu Cys Pro Pro Leu Glu Leu
            20                  25                  30

Leu Leu Leu Leu Leu Phe Ser Leu Gly Leu Leu His Ala Gly Asp Cys
        35                  40                  45

Gln Gln Pro Ala Gln Cys Arg Ile Gln Lys Cys Thr Thr Asp Phe Val
    50                  55                  60

Ser Leu Thr Ser His Leu Asn Ser Ala Val Asp Gly Phe Asp Ser Glu
65                  70                  75                  80

Phe Cys Lys Ala Leu Arg Ala Tyr Ala Gly Cys Thr Gln Arg Thr Ser
                85                  90                  95

Lys Ala Cys Arg Gly Asn Leu Val Tyr His Ser Ala Val Leu Gly Ile
            100                 105                 110

Ser Asp Leu Met Ser Gln Arg Asn Cys Ser Lys Asp Gly Pro Thr Ser
        115                 120                 125

-continued

```
Ser Thr Asn Pro Glu Val Thr His Asp Pro Cys Asn Tyr His Ser His
    130                 135                 140

Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
            180                 185                 190

Asn Tyr Leu Ser Val Gln Val Thr Asn Val Pro Val Pro Gly Ser
        195                 200                 205

Ser Ala Thr Ala Thr Asn Lys Ile Thr Ile Ile Phe Lys Ala His His
    210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
            260                 265                 270

Ala Arg Tyr Ile Gly Thr Thr Val Phe Val Arg Gln Val Gly Arg Tyr
        275                 280                 285

Leu Thr Leu Ala Ile Arg Met Pro Glu Asp Leu Ala Met Ser Tyr Glu
    290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
            340                 345                 350

Thr Ala Asn Thr Gln Cys His Glu Lys Met Pro Val Lys Asp Ile Tyr
        355                 360                 365

Phe Gln Ser Cys Val Phe Asp Leu Leu Thr Thr Gly Asp Ala Asn Phe
    370                 375                 380

Thr Ala Ala His Ser Ala Leu Glu Asp Val Glu Ala Leu His Pro
385                 390                 395                 400

Arg Lys Glu Arg Trp His Ile Phe Pro Ser Ser Gly Asn Gly Thr Pro
                405                 410                 415

Arg Gly Gly Ser Asp Leu Ser Val Ser Leu Gly Leu Thr Cys Leu Ile
            420                 425                 430

Leu Ile Val Phe Leu
        435

<210> SEQ ID NO 21
<211> LENGTH: 372
<212> TYPE: PRT
<213> ORGANISM: Homo sapiens

<400> SEQUENCE: 21

Met Ser Arg Arg Arg Phe Asp Cys Arg Ser Ile Ser Gly Leu Leu Thr
1               5                   10                  15

Thr Thr Pro Gln Ile Pro Ile Lys Met Glu Asn Phe Asn Asn Phe Tyr
            20                  25                  30

Ile Leu Thr Ser Lys Glu Leu Gly Arg Gly Lys Phe Ala Val Val Arg
        35                  40                  45

Gln Cys Ile Ser Lys Ser Thr Gly Gln Glu Tyr Ala Ala Lys Phe Leu
    50                  55                  60
```

```
Lys Lys Arg Arg Arg Gly Gln Asp Cys Arg Ala Glu Ile Leu His Glu
 65                  70                  75                  80

Ile Ala Val Leu Glu Leu Ala Lys Ser Cys Pro Arg Val Ile Asn Leu
             85                  90                  95

His Glu Val Tyr Glu Asn Thr Ser Glu Ile Ile Leu Ile Leu Glu Tyr
            100                 105                 110

Ala Ala Gly Gly Glu Ile Phe Ser Leu Cys Leu Pro Glu Leu Ala Glu
        115                 120                 125

Met Val Ser Glu Asn Asp Val Ile Arg Leu Ile Lys Gln Ile Leu Glu
    130                 135                 140

Gly Val Tyr Tyr Leu His Gln Asn Asn Ile Val His Leu Asp Leu Lys
145                 150                 155                 160

Pro Gln Asn Ile Leu Leu Ser Ser Ile Tyr Pro Leu Gly Asp Ile Lys
                165                 170                 175

Ile Val Asp Phe Gly Met Ser Arg Lys Ile Gly His Ala Cys Glu Leu
            180                 185                 190

Arg Glu Ile Met Gly Thr Pro Glu Tyr Leu Ala Pro Glu Ile Leu Asn
        195                 200                 205

Tyr Asp Pro Ile Thr Thr Ala Thr Asp Met Trp Asn Ile Gly Ile Ile
210                 215                 220

Ala Tyr Met Leu Leu Thr His Thr Ser Pro Phe Val Gly Glu Asp Asn
225                 230                 235                 240

Gln Glu Thr Tyr Leu Asn Ile Ser Gln Val Asn Val Asp Tyr Ser Glu
                245                 250                 255

Glu Thr Phe Ser Ser Val Ser Gln Leu Ala Thr Asp Phe Ile Gln Ser
            260                 265                 270

Leu Leu Val Lys Asn Pro Glu Lys Arg Pro Thr Ala Glu Ile Cys Leu
        275                 280                 285

Ser His Ser Trp Leu Gln Gln Trp Asp Phe Glu Asn Leu Phe His Pro
    290                 295                 300

Glu Glu Thr Ser Ser Ser Ser Gln Thr Gln Asp His Ser Val Arg Ser
305                 310                 315                 320

Ser Glu Asp Lys Thr Ser Lys Ser Ser Cys Asn Gly Thr Cys Gly Asp
                325                 330                 335

Arg Glu Asp Lys Glu Asn Ile Pro Glu Asp Ser Ser Met Val Ser Lys
            340                 345                 350

Arg Phe Arg Phe Asp Asp Ser Leu Pro Asn Pro His Glu Leu Val Ser
        355                 360                 365

Asp Leu Leu Cys
    370

<210> SEQ ID NO 22
<211> LENGTH: 288
<212> TYPE: PRT
<213> ORGANISM: Homo sapiens

<400> SEQUENCE: 22

Met Lys Asp Arg Thr Gln Glu Leu Arg Thr Ala Lys Asp Ser Asp Asp
  1               5                  10                  15

Asp Asp Asp Val Ala Val Thr Val Asp Arg Asp Arg Phe Met Asp Glu
             20                  25                  30

Phe Phe Glu Gln Val Glu Glu Ile Arg Gly Phe Ile Asp Lys Ile Ala
         35                  40                  45

Glu Asn Val Glu Glu Val Lys Arg Lys His Ser Ala Ile Leu Ala Ser
 50                  55                  60
```

```
Pro Asn Pro Asp Glu Lys Thr Lys Glu Glu Leu Glu Leu Met Ser
 65                  70                  75                  80

Asp Ile Lys Lys Thr Ala Asn Lys Val Arg Ser Lys Leu Lys Ser Ile
                 85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Cys Cys
            260                 265                 270

Val Ile Leu Gly Ile Val Ile Ala Ser Thr Val Gly Gly Ile Phe Ala
    275                 280                 285

<210> SEQ ID NO 23
<211> LENGTH: 1124
<212> TYPE: PRT
<213> ORGANISM: Homo sapiens

<400> SEQUENCE: 23

Met Asp Ser Leu Ala Ser Leu Val Leu Cys Gly Val Ser Leu Leu Leu
 1               5                  10                  15

Ser Gly Thr Val Glu Gly Ala Met Asp Leu Ile Leu Ile Asn Ser Leu
                 20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160
```

```
Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
            245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
            325                 330                 335

Gly Leu Gln Cys Glu Arg Glu Gly Ile Gln Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
            405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
            485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
            565                 570                 575
```

-continued

```
Glu Val Glu Arg Arg Ser Val Gln Lys Ser Asp Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
            610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
            645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
            675                 680                 685

Ile Lys Asn Ala Thr Ile Thr Gln Tyr Gln Leu Lys Gly Leu Glu Pro
            690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
            770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
            930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
            965                 970                 975

Val Ala Lys Ile Ala Asp Phe Gly Leu Ser Arg Gly Gln Glu Val Tyr
            980                 985                 990
```

```
Val Lys Lys Thr Met Gly Arg Leu Pro Val Arg Trp Met Ala Ile Glu
            995                 1000                1005

Ser Leu Asn Tyr Ser Val Tyr Thr Thr Asn Ser Asp Val Trp Ser
        1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Thr Leu Tyr Glu Lys Phe Thr Tyr
    1100                1105                1110

Ala Gly Ile Asp Cys Ser Ala Glu Glu Ala Ala
    1115                1120
```

<210> SEQ ID NO 24
<211> LENGTH: 184
<212> TYPE: PRT
<213> ORGANISM: Homo sapiens
<400> SEQUENCE: 24

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 25
<211> LENGTH: 1124
<212> TYPE: PRT
<213> ORGANISM: Homo sapiens

<400> SEQUENCE: 25

```
Met Asp Ser Leu Ala Ser Leu Val Leu Cys Gly Val Ser Leu Leu Leu
1               5                   10                  15
Ser Gly Thr Val Glu Gly Ala Met Asp Leu Ile Leu Ile Asn Ser Leu
            20                  25                  30
Pro Leu Val Ser Asp Ala Glu Thr Ser Leu Thr Cys Ile Ala Ser Gly
        35                  40                  45
Trp Arg Pro His Glu Pro Ile Thr Ile Gly Arg Asp Phe Glu Ala Leu
    50                  55                  60
Met Asn Gln His Gln Asp Pro Leu Glu Val Thr Gln Asp Val Thr Arg
65                  70                  75                  80
Glu Trp Ala Lys Lys Val Val Trp Lys Arg Glu Lys Ala Ser Lys Ile
                85                  90                  95
Asn Gly Ala Tyr Phe Cys Glu Gly Arg Val Arg Gly Glu Ala Ile Arg
            100                 105                 110
Ile Arg Thr Met Lys Met Arg Gln Gln Ala Ser Phe Leu Pro Ala Thr
        115                 120                 125
Leu Thr Met Thr Val Asp Lys Gly Asp Asn Val Asn Ile Ser Phe Lys
130                 135                 140
Lys Val Leu Ile Lys Glu Glu Asp Ala Val Ile Tyr Lys Asn Gly Ser
145                 150                 155                 160
Phe Ile His Ser Val Pro Arg His Glu Val Pro Asp Ile Leu Glu Val
                165                 170                 175
His Leu Pro His Ala Gln Pro Gln Asp Ala Gly Val Tyr Ser Ala Arg
            180                 185                 190
Tyr Ile Gly Gly Asn Leu Phe Thr Ser Ala Phe Thr Arg Leu Ile Val
        195                 200                 205
Arg Arg Cys Glu Ala Gln Lys Trp Gly Pro Glu Cys Asn His Leu Cys
210                 215                 220
Thr Ala Cys Met Asn Asn Gly Val Cys His Glu Asp Thr Gly Glu Cys
225                 230                 235                 240
Ile Cys Pro Pro Gly Phe Met Gly Arg Thr Cys Glu Lys Ala Cys Glu
                245                 250                 255
Leu His Thr Phe Gly Arg Thr Cys Lys Glu Arg Cys Ser Gly Gln Glu
            260                 265                 270
Gly Cys Lys Ser Tyr Val Phe Cys Leu Pro Asp Pro Tyr Gly Cys Ser
        275                 280                 285
Cys Ala Thr Gly Trp Lys Gly Leu Gln Cys Asn Glu Ala Cys His Pro
290                 295                 300
Gly Phe Tyr Gly Pro Asp Cys Lys Leu Arg Cys Ser Cys Asn Asn Gly
305                 310                 315                 320
Glu Met Cys Asp Arg Phe Gln Gly Cys Leu Cys Ser Pro Gly Trp Gln
                325                 330                 335
Gly Leu Gln Cys Glu Arg Glu Gly Ile Gln Arg Met Thr Pro Lys Ile
            340                 345                 350
Val Asp Leu Pro Asp His Ile Glu Val Asn Ser Gly Lys Phe Asn Pro
        355                 360                 365
Ile Cys Lys Ala Ser Gly Trp Pro Leu Pro Thr Asn Glu Glu Met Thr
370                 375                 380
Leu Val Lys Pro Asp Gly Thr Val Leu His Pro Lys Asp Phe Asn His
385                 390                 395                 400
Thr Asp His Phe Ser Val Ala Ile Phe Thr Ile His Arg Ile Leu Pro
                405                 410                 415
```

```
Pro Asp Ser Gly Val Trp Val Cys Ser Val Asn Thr Val Ala Gly Met
            420                 425                 430
Val Glu Lys Pro Phe Asn Ile Ser Val Lys Val Leu Pro Lys Pro Leu
    435                 440                 445
Asn Ala Pro Asn Val Ile Asp Thr Gly His Asn Phe Ala Val Ile Asn
450                 455                 460
Ile Ser Ser Glu Pro Tyr Phe Gly Asp Gly Pro Ile Lys Ser Lys Lys
465                 470                 475                 480
Leu Leu Tyr Lys Pro Val Asn His Tyr Glu Ala Trp Gln His Ile Gln
                485                 490                 495
Val Thr Asn Glu Ile Val Thr Leu Asn Tyr Leu Glu Pro Arg Thr Glu
            500                 505                 510
Tyr Glu Leu Cys Val Gln Leu Val Arg Arg Gly Glu Gly Gly Glu Gly
        515                 520                 525
His Pro Gly Pro Val Arg Arg Phe Thr Thr Ala Ser Ile Gly Leu Pro
    530                 535                 540
Pro Pro Arg Gly Leu Asn Leu Leu Pro Lys Ser Gln Thr Thr Leu Asn
545                 550                 555                 560
Leu Thr Trp Gln Pro Ile Phe Pro Ser Ser Glu Asp Asp Phe Tyr Val
                565                 570                 575
Glu Val Glu Arg Arg Ser Val Gln Lys Ser Asp Gln Asn Ile Lys
            580                 585                 590
Val Pro Gly Asn Leu Thr Ser Val Leu Leu Asn Asn Leu His Pro Arg
        595                 600                 605
Glu Gln Tyr Val Val Arg Ala Arg Val Asn Thr Lys Ala Gln Gly Glu
    610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                645                 650                 655
Ile Ser Trp Thr Ile Leu Asp Gly Tyr Ser Ile Ser Ser Ile Thr Ile
            660                 665                 670
Arg Tyr Lys Val Gln Gly Lys Asn Glu Asp Gln His Val Asp Val Lys
        675                 680                 685
Ile Lys Asn Ala Thr Ile Thr Gln Tyr Gln Leu Lys Gly Leu Glu Pro
    690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Gly Lys Met Leu Leu Ile Ala Ile Leu
            740                 745                 750
Gly Ser Ala Gly Met Thr Cys Leu Thr Val Leu Leu Ala Phe Leu Ile
        755                 760                 765
Ile Leu Gln Leu Lys Arg Ala Asn Val Gln Arg Arg Met Ala Gln Ala
    770                 775                 780
Phe Gln Asn Val Arg Glu Glu Pro Ala Val Gln Phe Asn Ser Gly Thr
785                 790                 795                 800
Leu Ala Leu Asn Arg Lys Val Lys Asn Asn Pro Asp Pro Thr Ile Tyr
                805                 810                 815
Pro Val Leu Asp Trp Asn Asp Ile Lys Phe Gln Asp Val Ile Gly Glu
            820                 825                 830
```

```
Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                    885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
                980                 985                 990

Val Lys Lys Thr Met Gly Arg Leu Pro Val Arg Trp Met Ala Ile Glu
            995                1000                1005

Ser Leu Asn Tyr Ser Val Tyr Thr Thr Asn Ser Asp Val Trp Ser
            1010                1015                1020

Tyr Gly Val Leu Leu Trp Glu Ile Val Ser Leu Gly Gly Thr Pro
            1025                1030                1035

Tyr Cys Gly Met Thr Cys Ala Glu Leu Tyr Glu Lys Leu Pro Gln
            1040                1045                1050

Gly Tyr Arg Leu Glu Lys Pro Leu Asn Cys Asp Asp Glu Val Tyr
            1055                1060                1065

Asp Leu Met Arg Gln Cys Trp Arg Glu Lys Pro Tyr Glu Arg Pro
            1070                1075                1080

Ser Phe Ala Gln Ile Leu Val Ser Leu Asn Arg Met Leu Glu Glu
            1085                1090                1095

Arg Lys Thr Tyr Val Asn Thr Thr Leu Tyr Glu Lys Phe Thr Tyr
            1100                1105                1110

Ala Gly Ile Asp Cys Ser Ala Glu Glu Ala Ala
            1115                1120
```

The invention claimed is:

1. A method for identifying a tumour in a subject likely to benefit from treatment with pan αv integrin inhibitor Abituzumab, said method comprising:

determining the levels of two or more proteins selected from the group consisting of DCN, F5, ICAM3, STK17B, STX1A, TEK, ANG, LEPR, MAP2K2, MAPK11, RGMB, and TNFRSF17 in at least one body fluid of said subject, wherein:

a) a high level of one or more proteins selected from the group consisting of:
DCN,
F5,
ICAM3,
PIGR,
STK17B,
STX1A, and
TEK,
and/or b) low levels of one or more proteins in at last one body fluid of said subject, wherein said one or more proteins are selected from the group consisting of:
ANG,
LEPR,
MAP2K2,
MAPK11,
RGMB, and
TNFRSF17; and identify a tumour likely to benefit from the treatment with the pan αv integrin inhibitor Abituzumab; and treating said subject with Abituzumab.

2. A method for identifying a tumour in a subject likely to benefit from treatment with the pan αv integrin inhibitor Abituzumab, said method comprising:
determining a level of a STX1A protein in one or more body fluids of said subject, wherein a high level thereof identifies a tumour likely to benefit from the treatment with the pan αv integrin inhibitor Abituzumab; and
treating said subject with Abituzumab.

3. The method according to claim 1, wherein the level of a respective protein in said at least one body fluid is
a) classified as high, if the respective protein level in said at least one body fluid is at least 5% higher than a median threshold determined for the respective protein, and/or
b) classified as low, if the respective protein level in said at least one body fluid is at least 5% lower than said median threshold determined for the respective protein.

4. The method according to claim 1, wherein the at least one body fluid comprises blood plasma or consist of blood plasma.

5. A method for identifying a subject responsive to treatment with pan αv integrin inhibitor Abituzumab, said method comprising:
determining the levels of two or more proteins selected from the group consisting of DCN, F5, ICAM3, PIGR, STK17B, STX1A TEK, ANG, LEPR, MAP2K2, MAPK11, RGMB, and TNFRSF17 in at least one body fluid of said subject, wherein:
a) a high level of one or more proteins selected from the group consisting of:
DCN,
F5,
ICAM3,
PIGR,
STK17B,
STX1A, and
TEK,
and/or
b) low levels of one or more proteins in at last one body fluid of said subject, wherein said one or more proteins are selected from the group consisting of:
ANG,
LEPR,
MAP2K2,
MAPK11,
RGMB, and
TNFRSF17;
identify a subject responsive to treatment with the pan αv integrin inhibitor Abituzumab; and
treating said subject with Abituzumab.

6. The method according to claim 1, wherein said at least one body fluid is blood plasma.

7. The method according to claim 1, wherein the Abituzumab is administered to said subject every week, every second week or every fourth week.

8. The method according to claim 2, wherein the level of said STX1A protein in at least one body fluid sample of said subject is
classified as high if the respective specific protein level in the one or more body fluid is at least 5% higher than a median threshold determined for STX1A protein.

9. The method according to claim 3, wherein said median threshold is determined in a subject population having bone metastasis disease.

10. The method according to claim 1, wherein said subject is characterized by a high level of the protein: STX1A and/or a protein having at least 90% sequence homology to said STX1A protein.

11. The method according to claim 1, wherein said subject is characterized by the respective levels of one or more proteins having at least 90% sequence homology to said two or more proteins.

12. The method according to claim 1, wherein said at least one body fluid is selected from the group consisting of blood plasma, blood serum and whole blood.

13. The method according to claim 3, wherein high levels and/or low levels of said two or more proteins are present and/or determined prior to administering said pan αv integrin inhibitor Abituzumab.

14. The method according to claim 3, wherein high levels and/or low levels of said two or more proteins are present and/or determined during or after administering said pan αv integrin inhibitor Abituzumab.

15. The method according to claim 9, wherein the bone metastasis disease is cancer or is derived from cancer.

16. The method according to claim 9, wherein the bone metastasis disease is derived from prostate cancer, breast cancer and/or lung cancer.

17. The method according to claim 9, wherein said median threshold for the respective specific protein is determined from body fluid of a plurality of subjects being part of a diseased subject population suffering from the respective bone metastasis disease.

18. The method according to claim 1, wherein said Abituzumab is administered to said subject in an amount of 100 mg to 3000 mg per month.

19. The method according to claim 1, wherein the Abituzumab is administered to said subject in an amount of 500 to 2000 mg every week, every second week every or every fourth week.

20. The method according to claim 1, wherein the Abituzumab is administered to said subject in an amount of about 500 mg per week, about 750 mg per week, about 1000 mg per week or about 1500 mg per week.

21. The method according to claim 1, wherein said pan αv integrin inhibitor Abituzumab is administered in combination with one or more agents or chemotherapeutic agents:
a) selected from the group consisting of Leuproreline, Leuproreline acetate, bicalutamide, nilutamide, triptoreline, gosereline, flutamide, cyproterone, busereline and degarelix,
b) selected from the group consisting of Zoledronic acid, Pamidronic acid, Clodronate disodium, Alendronic acid and Ibandronic acid,
and/or
c) selected from the group consisting of Abiraterone, Abiraterone acetate, Prednisone, Enzalutamide, Radium Ra 223 dichloride, Docetaxel, Sipuleucel-T, Cabazitaxel and Mitoxantrone;
and/or the pharmaceutically acceptable derivatives and/or salts thereof.

22. The method according to claim 1, wherein said pan αv integrin inhibitor Abituzumab is administered in combination with 1, 2 or 3 agents or chemotherapeutic agents, selected from the group consisting of:
a) Leuproreline, Leuproreline acetate, bicalutamid, nilutamide, triptoreline, gosereline, flutamide, cyproterone, busereline and degarelix, and/or the pharmaceutically acceptable derivatives and/or salts thereof;
and/or
b) Zoledronic acid, Pamidronic acid, Clodronate disodium, Alendronic acid and Ibandronic acid, and/or the pharmaceutically acceptable derivatives and/or salts thereof.

23. The method according to claim 5, wherein the level of protein in said at least one body fluid is a) classified as high, if the respective protein level in said at least one body fluid is at least 5% higher than a median threshold determined for the respective protein, and/or
b) classified as low, if the respective protein level in said at least one body fluid is at least 5% lower than said median threshold determined for the respective protein.

* * * * *